United States Patent
Crosignani et al.

(10) Patent No.: US 9,126,984 B2
(45) Date of Patent: Sep. 8, 2015

(54) 4-(INDOL-3-YL)-PYRAZOLE DERIVATIVES, PHARMACEUTICAL COMPOSITIONS AND METHODS FOR USE

(71) Applicant: ITEOS THERAPEUTICS, Charleroi (BE)

(72) Inventors: Stefano Crosignani, Nivelles (BE); Sandra Cauwenberghs, Halle (BE); Frederik Deroose, Destelbergen (BE)

(*) Notice: Subject to any disclaimer, the term of this patent is extended or adjusted under 35 U.S.C. 154(b) by 0 days.

(21) Appl. No.: 14/076,016

(22) Filed: Nov. 8, 2013

(65) Prior Publication Data

US 2015/0133422 A1  May 14, 2015

(51) Int. Cl.
| | |
|---|---|
| C07D 403/14 | (2006.01) |
| C07D 401/14 | (2006.01) |
| C07D 405/14 | (2006.01) |
| C07D 409/14 | (2006.01) |
| C07D 403/04 | (2006.01) |

(52) U.S. Cl.
CPC .......... *C07D 409/14* (2013.01); *C07D 401/14* (2013.01); *C07D 403/04* (2013.01); *C07D 403/14* (2013.01); *C07D 405/14* (2013.01)

(58) Field of Classification Search
CPC .. C07D 403/14; C07D 401/14; C07D 405/14; C07D 409/14; C07D 403/04
See application file for complete search history.

(56) References Cited

U.S. PATENT DOCUMENTS

| | | |
|---|---|---|
| 2005/0165005 A1 | 7/2005 | Genevois et al. |
| 2011/0166143 A1 | 7/2011 | Bretschneider et al. |

FOREIGN PATENT DOCUMENTS

| | | |
|---|---|---|
| WO | 2010/008427 A1 | 1/2010 |
| WO | WO-2010/008427 A1 | 1/2010 |
| WO | WO-2010/136491 A1 | 12/2010 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
Vippagunta, et al. Advanced Drug Delivery Reviews 48 (2001) 3-26.*
Munn et al.,"Prevention of Allogeneic Fetal Rejection by Tryptophan Catabolism", Science, vol. 281, Aug. 1998, pp. 1191-1193.
Mellor et al., "Creating immune privilege: active local suppression that benefits friends, but protects foes", Nat. Rev. Immunol, vol. 8, Jan. 2008, pp. 74-80.
Munn et al., Inhibition of T Cell Proliferation by Macrophage Tryptophan Catabolism, J. Exp. Med., vol. 189, No. 9, May 1999, pp. 1363-1372.
Fallarino et al., "T cell apoptosis by Tryptophan catabolism", Cell Death Differ., vol. 9, 2002, pp. 1069-1077.
Opitz et al., "An endogenous tumour-promoting ligand of the human aryl hydrocarbon receptor", Nature, vol. 478, N° 7368, Oct. 2011, pp. 197-203.
Pilotte et al., "Reversal of tumoral immune resistance by inhibition of tryptophan 2,3-dioxygenase", PNAS, vol. 109, No. 7, Feb. 2012, pp. 2497-2502.
Uyttenhove et al., "Evidence for a tumoral immune resistance mechanism based on trytophan degradation by indoleamine 2,3-dioxygenase", Nat. Med., vol. 9, No. 10, Oct. 2003, pp. 1269-1274.
Muller A.J. et al. "Chronic inflammation that facilitates tumor progression creates local immune suppression by inducing indoleamine 2,3 dioxygenase", Proc. Natl. Acad. Sci. USA, vol. 105, No. 44, Nov. 2008, pp. 17073-17078.
Dolusic et al.,"Indoleamine 2,3-dioxygenase inhibitors: a patent review (2008-2012)", Expert Opin. Ther. Pat., vol. 23, No. 10, 2013, pp. 1367-1381.
Holmgaard et al., "Indoleamine 2,3-dioxygenase is a critical resistance mechanism in antitumor T cell immunotherapy targeting CTLA-4", J. Exp. Med., vol. 210, No. 7, Jun. 2013, pp. 1389-1402.

(Continued)

Primary Examiner — Shawquia Jackson
(74) Attorney, Agent, or Firm — Howson & Howson LLP; Cathy A. Kodroff; David A. Rubin

(57) ABSTRACT

The present invention embodiments relate to compound of Formula I

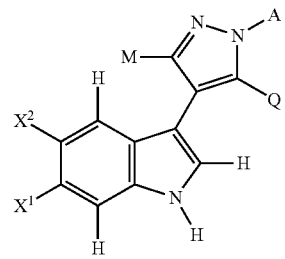

or pharmaceutically acceptable enantiomers, salts or solvates thereof. The invention further relates in certain embodiments to the use of the compounds of Formula I as TDO2 inhibitors. The invention also relates in certain embodiments to the use of the compounds of Formula I for the treatment and/or prevention of cancer, neurodegenerative disorders such as Parkinson's disease, Alzheimer's disease and Huntington's disease, chronic viral infections such as HCV and HIV, depression, and obesity. The invention also relates in certain embodiments to a process for manufacturing compounds of Formula I.

13 Claims, No Drawings

(56) References Cited

OTHER PUBLICATIONS

Jimenez et al., "4-(1-Phenyl-1H-pyrazol-4-yl)quinolines as novel, selective and brain penetrant metabotropic glutamate receptor 4 positive allosteric modulators", Bioorg. Med. Chem. Let., vol. 22, Mar. 2012, pp. 3235-3239.
Gupton et al., "Preparation of indole containing building blocks for the regiospecific construction of indole appended pyrazoles and pyrroles", Tetrahedron, vol. 69, May 2013, pp. 5829-5840.
Dolusic et al., "Tryptophan 2,3-Dioxygenase (TDO) Inhibitors. 3-(-2-(Pyridyl)ethenyl)indoles as Potential Anticancer Immunomodulators", J. Med. Chem., vol. 54, Jul. 2011, pp. 5320-5334.
Jakse et al., "Application of alkyl 3-dimethylamino-2-(1H-indol-3-yl)propenoates in the synthesis of 3-heteroarylindoles", Tetrahedron, vol. 60, Mar. 2004, pp. 4601-4608.
U.S. Appl. No. 14/179,440, filed Feb. 12, 2014 (ITEOS Therapeutics).
EP14154911.3, filed on Feb. 12, 2014 (ITEOS Therapeutics).
U.S. Appl. No. 14/218,296, filed Mar. 18, 2014 (ITEOS Therapeutics).
EP 14160578.2, filed on Mar. 18, 2014 (ITEOS Therapeutics).
European Search Report dated Feb. 19, 2014 from the corresponding patent application EP13192224.7.
Cavallo et al., 2011: The Immune Hallmarks of Cancer, Cancer Immunology Immunotherapy, vol. 60(3):319-326, Nov. 26, 2011.
Hanahan, D. and Weinberg, R.A., Hallmarks of Cancer: The Next Generation, Cell, vol. 144:646-674, Mar. 4, 2011.
Hanahan, D. and Weinberg, R.A., The Hallmarks of Cancer, Cell, vol. 100:57-70, Jan. 7, 2000.
Jimenez et al., 4-(1-Phenyl-1-pyrazol-4-ul) quinolones as novel, selective and brain penetrant metabotropic glutamate receptor 4 positive allosteric modulators, Bioorganic & Medicinal Chemistry Letters, Pergamon, vol. 22(9):3235-3239, Mar. 7, 2012.
Kyrgidia et al., Melanoma: Stem cells, sun exposure and hallmarks for carcinogenesis, molecular concepts and future clinical implications, Journal of Carcinogenesis, vol. 9(1):1-16, Feb. 16, 2010.

* cited by examiner

4-(INDOL-3-YL)-PYRAZOLE DERIVATIVES, PHARMACEUTICAL COMPOSITIONS AND METHODS FOR USE

BACKGROUND

1. Technical Field of Invention

The present invention embodiments relate to novel 4-(indol-3-yl)-pyrazole derivatives, including pharmaceutically acceptable enantiomers, salts and solvates thereof. Compounds of certain embodiments of the invention are inhibitors of TDO2 (tryptophan 2,3-dioxygenase) and are useful as therapeutic compounds, particularly in the treatment and/or reduction in the likelihood of occurrence of and/or prevention of cancers.

2. Description of the Related Art

Two decades after the importance of tryptophan catabolism for maintaining the immune privilege of the placenta was discovered (Munn, D. H. et al., *Science*, 1998, 281, 1191-1193), increasing evidence is extending its biological relevance beyond immune tolerance to non-self. According to the generally accepted concept, tryptophan, an essential amino acid, is catabolized in the local microenvironment of tumors, immune-privileged sites, or sites of inflammation (Mellor A L and Munn D H., *Nat Rev Immunol*, 2008, 8, 74-80). In these tissues, cancer cells, immune cells, or specialized epithelial cells (e.g., syncytiotrophoblasts in the placenta) create an immunosuppressive environment in tumors that shut down antitumor immune responses in tumors and in tumor-draining lymph nodes by inducing T-cell anergy and apoptosis through depletion of tryptophan and accumulation of immunosuppressive tryptophan catabolites (Munn D H et al., *J Exp. Med.*, 1999, 189, 1363-1372; Fallarino F et al., *Cell Death Differ.*, 2002, 9, 1069-1077).

It has now been discovered that a key enzyme in tryptophan catabolism, tryptophan 2,3-dioxygenase (TDO2), which is considered responsible for regulating systemic tryptophan levels in the liver, is constitutively expressed in some cancers. TDO2 expression in tumor cells prevents tumor surveillance by the immune system and thus prevents tumor rejection by locally degrading tryptophan (Opitz C A et al., *Nature*, 2011, 478(7368), 197-203). In addition, inhibition of TDO2 by a small molecule prevents tumor growth in animal models for immunotherapy (Pilotte L et al., *Proc Natl Acad Sci USA*, 2012, 109(7), 2497-502).

The tryptophan catabolism in some cancers might be also increased by the expression of indoleamine 2,3-dioxygenase (IDO) by tumor cells (Uyttenhove, C. et al., *Nat. Med.*, 2003, 9, 1269-1274).

Because tryptophan catabolism is induced by inflammatory mediators, notably IFN-gamma, it is thought to represent an endogenous mechanism that restricts excessive immune responses, thereby preventing immunopathology. In the context of cancer, this feedback loop may not be beneficial, as tryptophan catabolism has been implicated in inflammation-driven cancers such as colon cancer (Muller A J et al., *Proc Natl Acad Sci USA*, 2008, 105, 17073-8). There is strong evidence that suppression of antitumor immune responses in precancerous lesions and established cancers by tryptophan catabolism promotes tumor growth, which would make such catabolism an attractive target for therapeutic intervention (Dolugie E and Frederick R., *Expert Opin Ther Pat.*, 2013, 23(10), 1367-81). Hence, a considerable effort is being made to identify selective and efficient inhibitors of tryptophan catabolism to enhance the efficacy of conventional chemotherapy, immune checkpoints (Holmgaard R B et al., *J Exp Med.*, 2013, 210(7), 1389-402) or therapeutic vaccines.

Some TDO2 inhibitors were proposed in WO2010/008427 and by Dolusic, E. et al. (Dolusic et al., *J. Med. Chem.*, 2011, 54, 5320-5334), however either their affinity for the target is limited, or their pharmacokinetic properties are not suitable for development as a drug for human use.

Therefore, there is a need for new TDO2 inhibitors with improved efficacy for treating and/or reducing the likelihood of occurrence of cancer and/or for cancer prevention. The present invention provides according to certain herein disclosed embodiments new TDO2 inhibitors which may be administered to any patient diagnosed with cancer, or to any subject being at risk of developing a cancer.

BRIEF SUMMARY

The present invention provides, according to certain embodiments, a compound of Formula I:

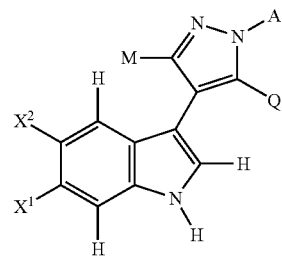

or a pharmaceutically acceptable enantiomer, salt or solvate thereof wherein:

$X^1$ and $X^2$ represent each independently H, halogen or haloalkyl, preferably H, F or $CF_3$, more preferably H or F; M and Q represent each independently H, halogen, hydroxyl, C1-C6 alkyl optionally substituted by one or more substituents selected from the group comprising halogen, hydroxyl, $CONR^1R^2$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

A represents:
- a hydrogen atom;
- aryl, optionally substituted with halogen, hydroxyl, nitro, amido, carboxy, amino, cyano, haloalkoxy, haloalkyl, alkyl;
- heteroaryl, optionally substituted with halogen, hydroxyl, nitro, amido, carboxy, amino, cyano, haloalkoxy, haloalkyl, alkyl; preferably substituted or unsubstituted pyridyl or pyridazine, more preferably substituted or unsubstituted pyridyl;
- C1-C10 alkyl, linear or branched, optionally substituted with up to three substituents selected from the group comprising halogen, hydroxyl, $COOR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group, optionally substituted, selected from C1-C6 alkyl, aryl, heteroaryl, amino;
- heterocyclyl, preferably saturated heteroaryl selected from azetidine, piperidine, morpholine, piperazine, tetrahydrofurane, tetrahydropyrane, tetrahydro-thiopyran-dioxide, dioxane, imidazolidinone, pyrrolidine, pyrrolidinone; optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$;

C1-C3 alkyl-heterocyclyl, preferably saturated heteroaryl selected from azetidine, piperidine, morpholine, piperazine, tetrahydrofurane, tetrahydropyrane, tetrahydrothiopyran-dioxide, dioxane, imidazolidinone, pyrrolidine, pyrrolidinone; wherein both the C1-C3 alkyl and the heterocyclyl are optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group, optionally substituted, selected from C1-C6 alkyl, cycloalkyl, alkene, aryl, heteroaryl and amino, optionally substituted by one or more groups selected from halogen, hydroxyl, alkoxy, COOH, amino, $SO_2Me$;

cycloalkyl, preferably cyclobutane or cyclohexyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$;

C1-C3 alkyl-cycloalkyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a group selected from C1-C6 alkyl, cycloalkyl, alkene, aryl, heteroaryl and amino, optionally substituted by one or more groups selected from halogen, hydroxyl, alkoxy, COOH, amino, $SO_2Me$.

In certain embodiments there is provided a compound of Formula I, having Formula Ia:

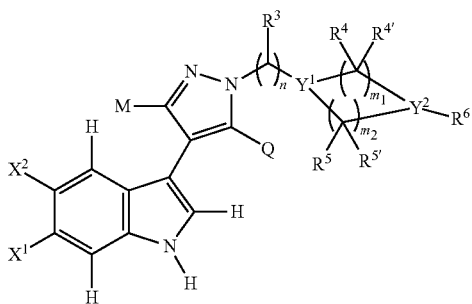

or a pharmaceutically acceptable enantiomer, salt or solvates thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted by one or more substituents selected from the group comprising halogen, hydroxyl, $CONR^1R^2$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

n represents an integer equal to 0, 1, 2 or 3;

$m_1$ and $m_2$ represent each independently an integer equal to 1 or 2;

$Y^1$ and $Y^2$ represent each independently $CR^7$, N, O, $SO_2$, wherein $R^7$ represents H or hydroxyl;

$R^3$ represents H, alkyl;

$R^4$, $R^{4'}$, $R^5$ and $R^{5'}$ represent each independently H, hydroxyl, alkyl, alkoxy, haloalkyl or $R^4$ and $R^{4'}$ form together an oxo moiety or $R^5$ and $R^{5'}$ form together an oxo moiety;

$R^6$ is absent or represents H, alkyl, the alkyl group being optionally substituted by one or more groups selected from halogen, hydroxyl or COOH; cycloalkyl, halogen, hydroxyl, oxo, $COR^1$, $COOR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$.

In certain further embodiments there is provided a compound having Formula Ia-1:

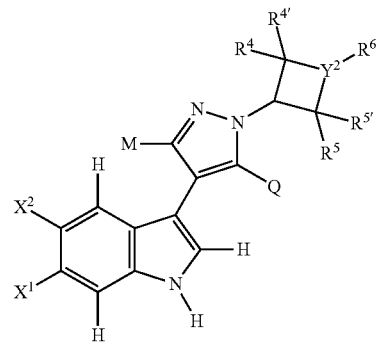

or a pharmaceutically acceptable enantiomer, salt or solvate thereof, wherein:

$X^1$ and $X^2$ represent each independently H or F;

M and Q represent each independently H, C1-C6 alkyl optionally substituted by one or more halogen;

$Y^2$ represents N or CH;

$R^4$, $R^{4'}$, $R^5$ and $R^{5'}$ represent each independently H, hydroxyl, alkyl, alkoxy, haloalkyl or $R^4$ and $R^{4'}$ form together an oxo moiety or $R^5$ and $R^{5'}$ form together an oxo moiety, preferably $R^4$, $R^{4'}$, $R^5$ and $R^{5'}$ represent H or oxo;

$R^6$ represents H, alkyl, the alkyl group being optionally substituted by one or more groups selected from halogen, hydroxyl or COOH; cycloalkyl, halogen, hydroxyl, oxo, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, SO₂Me; preferably R⁶ represents H, COOH, COMe, CONH₂, CONHMe.

In certain other further embodiments there is provided a compound having Formula Ia-2:

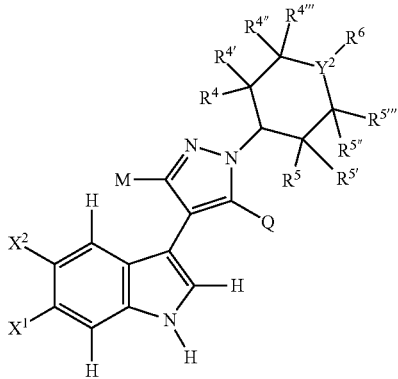

or a pharmaceutically acceptable enantiomer, salt or solvate thereof, wherein:

X¹ and X² represent each independently H or F;

M and Q represent each independently H, C1-C6 alkyl optionally substituted one or more alogen;

Y² represents N or CH; preferably Y is N;

R⁴, R⁴', R⁴'', R⁴''', R⁵, R⁵', R⁵'' and R⁵''' represent each independently H, hydroxyl, alkyl, alkoxy, haloalkyl or R⁴ and R⁴' form together an oxo moiety or R⁴'' and R⁴''' form together an oxo moiety or R⁵ and R⁵' form together an oxo moiety or R⁵'' and R⁵''' form together an oxo moiety, preferably R⁴, R⁴', R⁴'', R⁴''', R⁵, R⁵', R⁵'' and R⁵''' represent H or oxo;

R⁶ represents

H;

alkyl, the alkyl group being optionally substituted by one or more groups selected from halogen, hydroxyl or COOH; preferably methyl or —CH₂—CH₂—OH;

cycloalkyl;

halogen;

hydroxyl;

oxo;

COR¹, SO₂R¹, wherein R¹ represents a group selected from C1-C6 alkyl, preferably Me, Et, iPr, tBu; cycloalkyl, preferably cyclopropane; alkene, preferably ethylene; amino, preferably NMe₂; wherein R¹ groups are optionally substituted by one or more groups selected from halogen, preferably F; hydroxyl; alkoxy, preferably OMe; COOH; amino, preferably NMe₂ or NH₂; SO₂Me.

In certain other further embodiments there is provided a compound having Formula Ia-3:

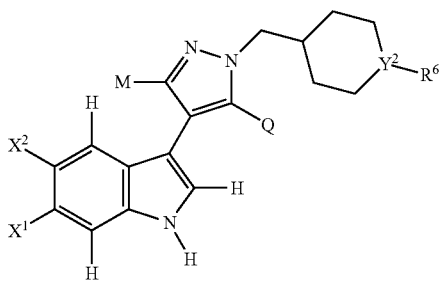

or a pharmaceutically acceptable enantiomer, salt and solvate thereof, wherein:

X¹ and X² represent each independently H or F;

M and Q represent each independently H, C1-C6 alkyl optionally substituted one or more halogen;

Y² represents N or CH; preferably Y is N;

R⁶ represents

H;

alkyl, the alkyl group being optionally substituted by one or more groups selected from halogen, hydroxyl or COOH;

cycloalkyl, preferably cyclopropane;

COR¹, SO₂R¹, wherein R¹ represents a group selected from C1-C6 alkyl, preferably methyl or ethyl; cycloalkyl; alkene; amino; wherein R¹ groups are optionally substituted by one or more groups selected from halogen; hydroxyl; alkoxy; COOH; amino; SO₂Me.

In certain embodiments there is provided a compound of Formula I, having Formula Ib:

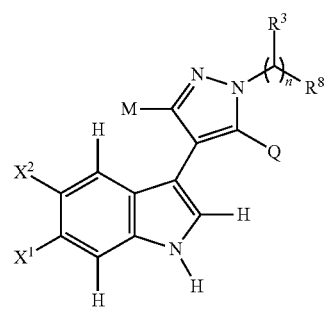

or a pharmaceutically acceptable enantiomer, salt or solvate thereof, wherein:

X¹ and X² represent each independently H, halogen or haloalkyl, preferably H, F or CF₃, more preferably H or F;

M and Q represent each independently H, halogen, hydroxyl, C1-C6 alkyl optionally substituted by one or more substituents selected from the group comprising halogen, hydroxyl, CONR¹R², NR¹COR² wherein R¹ and R² represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or CF₃, more preferably H or methyl;

n represents an integer equal to 1, 2 or 3, preferably 1 or 2;

R³ represents H, alkyl;

R⁸ represents H, alkyl, the alkyl group being optionally substituted by one or more groups selected from halogen, hydroxyl, COOH, CONH₂; cycloalkyl, halogen, hydroxyl, oxo, COR¹, COOR¹, CONR¹R², NR¹COR², NR¹R², SO₂R¹, SO₂NR¹R², NR¹SO₂R², SOR¹, wherein R¹ and R² represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, SO₂Me.

In certain embodiments there is provided a compound of Formula I, having having Formula Ic:

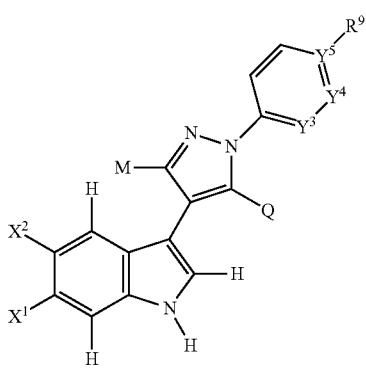

or pharmaceutically acceptable enantiomer, salt or solvate thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted one or more substituents selected from the group comprising halogen, hydroxyl, $CONR^1R^1$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

$Y^3$, $Y^4$, $Y^5$ represent each independently N or CH;

$R^9$ is absent or represents H; halogen, preferably Cl; amino, preferably $NH_2$.

In certain embodiments there is provided a compound of Formula I, selected from the group consisting of:

3-(4-(6-fluoro-1H-indol-3-yl)-1H-pyrazol-1-yl)azetidin-2-one,
3-(1-(azetidin-3-yl)-1H-pyrazol-4-yl)-6-fluoro-1H-indole,
1-(3-(4-(6-fluoro-1H-indol-3-yl)-1H-pyrazol-1-yl)azetidin-1-yl)ethanone,
3-(4-(6-fluoro-1H-indol-3-yl)-1H-pyrazol-1-yl)azetidine-1-carboxamide,
3-(4-(6-fluoro-1H-indol-3-yl)-1H-pyrazol-1-yl)-N-methylazetidine-1-carboxamide,
3-(1-(azetidin-3-ylmethyl)-1H-pyrazol-4-yl)-6-fluoro-1H-indole,
3-(4-(6-fluoro-1H-indol-3-yl)-1H-pyrazol-1-yl)propanamide,
3-(4-(5,6-difluoro-1H-indol-3-yl)-1H-pyrazol-1-yl)propanamide,
3-(4-(6-fluoro-1H-indol-3-yl)-3,5-dimethyl-1H-pyrazol-1-yl)propanamide,
3-(4-(6-fluoro-1H-indol-3-yl)-3-methyl-1H-pyrazol-1-yl)propanamide,
3-(4-(6-fluoro-1H-indol-3-yl)-5-methyl-1H-pyrazol-1-yl)propanamide,
3-(4-(1H-indol-3-yl)-5-(trifluoromethyl)-1H-pyrazol-1-yl)propanamide,
N-(2-(dimethylamino)ethyl)-3-(4-(6-fluoro-1H-indol-3-yl)-1H-pyrazol-1-yl)propanamide,
3-(4-(6-fluoro-1H-indol-3-yl)-1H-pyrazol-1-yl)-N-methylpropanamide,
3-(4-(6-fluoro-1H-indol-3-yl)-1H-pyrazol-1-yl)-N,N-dimethylpropanamide,
3-(4-(6-fluoro-1H-indol-3-yl)-1H-pyrazol-1-yl)propanoic acid,
3-(4-(5,6-difluoro-1H-indol-3-yl)-1H-pyrazol-1-yl)propanoic acid,
1-(2-(4-(6-fluoro-1H-indol-3-yl)-1H-pyrazol-1-yl)ethyl)imidazolidin-2-one,
6-fluoro-3-(1-(2-(4-methylpiperazin-1-yl)ethyl)-1H-pyrazol-4-yl)-1H-indole,
4-(2-(4-(6-fluoro-1H-indol-3-yl)-1H-pyrazol-1-yl)ethyl)morpholine,
N-(2-(4-(6-fluoro-1H-indol-3-yl)-1H-pyrazol-1-yl)ethyl)acetamide,
1-(2-(4-(6-fluoro-1H-indol-3-yl)-1H-pyrazol-1-yl)ethyl)urea,
1-(2-(4-(6-fluoro-1H-indol-3-yl)-1H-pyrazol-1-yl)ethyl)-3-methylurea,
2-(4-(6-fluoro-1H-indol-3-yl)-1H-pyrazol-1-yl)-N-methylethanamine,
N-(2-(4-(6-fluoro-1H-indol-3-yl)-1H-pyrazol-1-yl)ethyl)methanesulfonamide,
2-(4-(6-fluoro-1H-indol-3-yl)-1H-pyrazol-1-yl)ethanol,
6-fluoro-3-(1-(2-(piperazin-1-yl)ethyl)-1H-pyrazol-4-yl)-1H-indole,
1-(4-(2-(4-(6-fluoro-1H-indol-3-yl)-1H-pyrazol-1-yl)ethyl)piperazin-1-yl)ethanone,
6-fluoro-3-(1-(2-(pyrrolidin-1-yl)ethyl)-1H-pyrazol-4-yl)-1H-indole,
1-(2-(4-(6-fluoro-1H-indol-3-yl)-1H-pyrazol-1-yl)ethyl)pyrrolidin-2-one,
6-fluoro-3-(1-(2-(methylsulfonyl)ethyl)-1H-pyrazol-4-yl)-1H-indole,
5,6-difluoro-3-(1-(2-(methylsulfonyl)ethyl)-1H-pyrazol-4-yl)-1H-indole,
3-(3,5-dimethyl-1-(2-(methylsulfonyl)ethyl)-1H-pyrazol-4-yl)-6-fluoro-1H-indole,
3-(1-(2-(methylsulfonyl)ethyl)-5-(trifluoromethyl)-1H-pyrazol-4-yl)-1H-indole,
(−)-3-(4-(6-fluoro-1H-indol-3-yl)-1H-pyrazol-1-yl)-2-methylpropanamide,
(+)-3-(4-(6-fluoro-1H-indol-3-yl)-1H-pyrazol-1-yl)-2-methylpropanamide,
3-(4-(6-fluoro-1H-indol-3-yl)-1H-pyrazol-1-yl)-2-hydroxypropanamide,
2-(4-(6-fluoro-1H-indol-3-yl)-1H-pyrazol-1-yl)acetamide,
2-(4-(6-fluoro-1H-indol-3-yl)-1H-pyrazol-1-yl)-N-methylacetamide,
2-(4-(6-fluoro-1H-indol-3-yl)-1H-pyrazol-1-yl)-N,N-dimethylacetamide,
2-(4-(6-fluoro-1H-indol-3-yl)-1H-pyrazol-1-yl)acetic acid,
methyl 2-(4-(6-fluoro-1H-indol-3-yl)-1H-pyrazol-1-yl)acetate,
6-fluoro-3-(1-(piperidin-4-ylmethyl)-1H-pyrazol-4-yl)-1H-indole,
5,6-difluoro-3-(1-(piperidin-4-ylmethyl)-1H-pyrazol-4-yl)-1H-indole,
6-fluoro-3-(1-((1-(2,2,2-trifluoroethyl)piperidin-4-yl)methyl)-1H-pyrazol-4-yl)-1H-indole,
6-fluoro-3-(1-((1-(2-fluoroethyl)piperidin-4-yl)methyl)-1H-pyrazol-4-yl)-1H-indole,
2-(4-((4-(6-fluoro-1H-indol-3-yl)-1H-pyrazol-1-yl)methyl)piperidin-1-yl)ethanol,
1,1,1-trifluoro-3-(4-((4-(6-fluoro-1H-indol-3-yl)-1H-pyrazol-1-yl)methyl)piperidin-1-yl)propan-2-ol,
2-(4-((4-(6-fluoro-1H-indol-3-yl)-1H-pyrazol-1-yl)methyl)piperidin-1-yl)acetic acid,
4-(4-((4-(6-fluoro-1H-indol-3-yl)-1H-pyrazol-1-yl)methyl)piperidin-1-yl)-4-oxobutanoic acid,
1-(4-((4-(6-fluoro-1H-indol-3-yl)-1H-pyrazol-1-yl)methyl)piperidin-1-yl)ethanone,
3-(1-((1-cyclopropylpiperidin-4-yl)methyl)-1H-pyrazol-4-yl)-6-fluoro-1H-indole, 6-fluoro-3-(1-((1-methylpiperidin-4-yl)methyl)-1H-pyrazol-4-yl)-1H-indole, 6-fluoro-3-(1-(((1-(methylsulfonyl)piperidin-4-yl)methyl)-1H-pyrazol-4-yl)-1H-indole,
3-(3,5-dimethyl-1-(piperidin-4-ylmethyl)-1H-pyrazol-4-yl)-6-fluoro-1H-indole,
6-fluoro-3-(3-methyl-1-(piperidin-4-ylmethyl)-1H-pyrazol-4-yl)-1H-indole,
6-fluoro-3-(5-methyl-1-(piperidin-4-ylmethyl)-1H-pyrazol-4-yl)-1H-indole,
6-fluoro-3-(1-((tetrahydro-2H-pyran-4-yl)methyl)-1H-pyrazol-4-yl)-1H-indole,
4-((4-(6-fluoro-1H-indol-3-yl)-1H-pyrazol-1-yl)methyl)tetrahydro-2H-pyran-4-ol,
4-((4-(6-fluoro-1H-indol-3-yl)-1H-pyrazol-1-yl)methyl)tetrahydro-2H-thiopyran 1,1-dioxide,
(1S,3S)-3-(4-(6-fluoro-1H-indol-3-yl)-1H-pyrazol-1-yl)cyclobutanecarboxamide,
(1R,3R)-3-(4-(6-fluoro-1H-indol-3-yl)-1H-pyrazol-1-yl)cyclobutanecarboxamide,
(1S,3S)-3-(4-(6-fluoro-1H-indol-3-yl)-1H-pyrazol-1-yl)-N-methylcyclobutanecarboxamide,
(1R,3R)-3-(4-(6-fluoro-1H-indol-3-yl)-1H-pyrazol-1-yl)-N-methylcyclobutanecarboxamide,
(1S,3S)-3-(4-(6-fluoro-1H-indol-3-yl)-1H-pyrazol-1-yl)cyclobutanecarboxylic acid,
(1R,3R)-3-(4-(6-fluoro-1H-indol-3-yl)-1H-pyrazol-1-yl)cyclobutanecarboxylic acid,
(1R,4R)-4-(4-(6-fluoro-1H-indol-3-yl)-1H-pyrazol-1-yl)cyclohexanecarboxamide,
(1R,4R)-4-(4-(6-fluoro-1H-indol-3-yl)-1H-pyrazol-1-yl)cyclohexanol,
(1R,4R)-4-(4-(6-fluoro-1H-indol-3-yl)-1H-pyrazol-1-yl)cyclohexanol,
6-fluoro-3-(1H-pyrazol-4-yl)-1H-indole,
5,6-difluoro-3-(1H-pyrazol-4-yl)-1H-indole,
3-(1H-pyrazol-4-yl)-6-(trifluoromethyl)-1H-indole,
6-fluoro-3-(1-methyl-1H-pyrazol-4-yl)-1H-indole,
3-(1,5-dimethyl-1H-pyrazol-4-yl)-6-fluoro-1H-indole,
3-(1,3-dimethyl-1H-pyrazol-4-yl)-6-fluoro-1H-indole,
6-fluoro-3-(1,3,5-trimethyl-1H-pyrazol-4-yl)-1H-indole,
3-(1-methyl-5-(trifluoromethyl)-1H-pyrazol-4-yl)-1H-indole,
6-fluoro-3-(1-(piperidin-4-yl)-1H-pyrazol-4-yl)-1H-indole,
2-(4-(4-(6-fluoro-1H-indol-3-yl)-1H-pyrazol-1-yl)piperidin-1-yl)ethanol,
4-(4-(4-(6-fluoro-1H-indol-3-yl)-1H-pyrazol-1-yl)piperidin-1-yl)-4-oxobutanoic acid,
1-(4-(4-(6-fluoro-1H-indol-3-yl)-1H-pyrazol-1-yl)piperidin-1-yl)-3-methoxypropan-1-one,
1-(4-(4-(6-fluoro-1H-indol-3-yl)-1H-pyrazol-1-yl)piperidin-1-yl)propan-1-one,
2-(dimethylamino)-1-(4-(4-(6-fluoro-1H-indol-3-yl)-1H-pyrazol-1-yl)piperidin-1-yl)ethanone,
1-(4-(4-(6-fluoro-1H-indol-3-yl)-1H-pyrazol-1-yl)piperidin-1-yl)-2-hydroxyethanone,
1-(4-(4-(6-fluoro-1H-indol-3-yl)-1H-pyrazol-1-yl)piperidin-1-yl)-2-methoxyethanone,
1-(4-(4-(6-fluoro-1H-indol-3-yl)-1H-pyrazol-1-yl)piperidin-1-yl)-2-methylpropan-1-one,
1-(4-(4-(6-fluoro-1H-indol-3-yl)-1H-pyrazol-1-yl)piperidin-1-yl)-2,2-dimethylpropan-1-one,
cyclopropyl(4-(4-(6-fluoro-1H-indol-3-yl)-1H-pyrazol-1-yl)piperidin-1-yl)methanone,
1-(4-(4-(6-fluoro-1H-indol-3-yl)-1H-pyrazol-1-yl)piperidin-1-yl)ethanone,
4-(4-(6-fluoro-1H-indol-3-yl)-1H-pyrazol-1-yl)-N,N-dimethylpiperidine-1-carboxamide,
6-fluoro-3-(1-(1-methylpiperidin-4-yl)-1H-pyrazol-4-yl)-1H-indole,
6-fluoro-3-(1-(1-(((trifluoromethyl)sulfonyl)piperidin-4-yl)-1H-pyrazol-4-yl)-1H-indole,
1-(4-(4-(1H-indol-3-yl)-5-(trifluoromethyl)-1H-pyrazol-1-yl)piperidin-1-yl)ethanone,
1-(4-(4-(6-fluoro-1H-indol-3-yl)-3-methyl-1H-pyrazol-1-yl)piperidin-1-yl)ethanone,
1-(4-(4-(6-fluoro-1H-indol-3-yl)-5-methyl-1H-pyrazol-1-yl)piperidin-1-yl)ethanone,
6-fluoro-3-(1-(1-((2-methoxyethyl)sulfonyl)piperidin-4-yl)-1H-pyrazol-4-yl)-1H-indole,
3-(1-(1-(cyclopropylsulfonyl)piperidin-4-yl)-1H-pyrazol-4-yl)-6-fluoro-1H-indole,
3-(1-(1-(ethylsulfonyl)piperidin-4-yl)-1H-pyrazol-4-yl)-6-fluoro-1H-indole,
6-fluoro-3-(1-(1-(isopropylsulfonyl)piperidin-4-yl)-1H-pyrazol-4-yl)-1H-indole,
4-(4-(6-fluoro-1H-indol-3-yl)-1H-pyrazol-1-yl)piperidin-2-one,
4-(4-(6-fluoro-1H-indol-3-yl)-1H-pyrazol-1-yl)-1-methylpiperidin-2-one,
1-(4-(4-(6-fluoro-1H-indol-3-yl)-1H-pyrazol-1-yl)piperidin-1-yl)prop-2-en-1-one,
1-(4-(4-(6-fluoro-1H-indol-3-yl)-1H-pyrazol-1-yl)piperidin-1-yl)-4-(methylsulfonyl)butan-1-one,
1-(4-(4-(6-fluoro-1H-indol-3-yl)-1H-pyrazol-1-yl)piperidin-1-yl)-3-hydroxypropan-1-one,
1-(4-(4-(6-fluoro-1H-indol-3-yl)-1H-pyrazol-1-yl)piperidin-1-yl)-3-(methylsulfonyl)propan-1-one,
6-fluoro-3-(1-(1-(methylsulfonyl)piperidin-4-yl)-1H-pyrazol-4-yl)-1H-indole,
6-fluoro-3-(1-(pyridazin-3-yl)-1H-pyrazol-4-yl)-1H-indole,
3-(1-(6-chloropyridazin-3-yl)-1H-pyrazol-4-yl)-6-fluoro-1H-indole,
6-(4-(6-fluoro-1H-indol-3-yl)-1H-pyrazol-1-yl)pyridazin-3-amine,
6-fluoro-3-(1-(pyridazin-4-yl)-1H-pyrazol-4-yl)-1H-indole,
6-fluoro-3-(1-(pyridin-2-yl)-1H-pyrazol-4-yl)-1H-indole,
6-fluoro-3-(1-(pyridin-3-yl)-1H-pyrazol-4-yl)-1H-indole,
6-fluoro-3-(1-(pyridin-4-yl)-1H-pyrazol-4-yl)-1H-indole,
or a pharmaceutically acceptable enantiomer, salt or solvate thereof.

In certain embodiments there is provided a pharmaceutical composition comprising the compound of Formula I, or a pharmaceutically acceptable enantiomer, salt or solvate thereof; and one or more of a pharmaceutically acceptable carrier, diluent, excipient and adjuvant. In certain embodiments there is provided a medicament comprising the compound of Formula I, or a pharmaceutically acceptable enantiomer, salt or solvate thereof.

In certain embodiments there is provided a method for treating or reducing likelihood of occurrence in a subject of one or more of cancer, a neurodegenerative disorder and a chronic viral infection, comprising administering to the subject the compound of Formula I or a pharmaceutically acceptable enantiomer, salt or solvate thereof. In certain embodiments there is provided a method of inhibiting tryptophan-2,3-dioxygenase (TDO2), comprising contacting TDO2 with the compound of Formula I or a pharmaceutically acceptable enantiomer, salt or solvate thereof under conditions and for a time sufficient for the compound to inhibit TDO2 enzymatic activity.

In certain embodiments there is provided a process for manufacturing the compound of Formula I or a pharmaceutically acceptable enantiomer, salt or solvate thereof, comprising deprotecting indole amine of a compound of Formula IV:

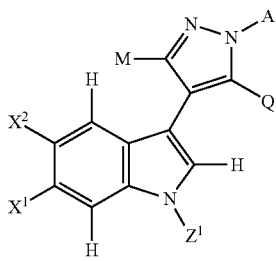

wherein $X^1$, $X^2$, M, Q and A are as defined in claim 1; and $Z^1$ represents an amino-protecting group selected from an arylsulphonyl, a tert-butoxy carbonyl, a methoxymethyl, a para-methoxy benzyl and a benzyl;

to afford the compound of Formula I. In certain further embodiments the process further comprises a preliminary step of reacting a compound of Formula II,

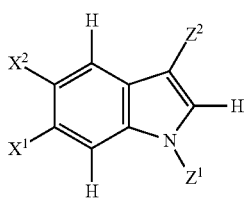

wherein $X^1$ and $X^2$ are as defined in Formula I;

$Z^1$ represents an amino-protecting group selected from an arylsulphonyl, a tert-butoxy carbonyl, a methoxymethyl, a para-methoxy benzyl and a benzyl;

$Z^2$ represents an halogen, an alkylsulfonyloxy having 1-6 carbon atoms or arylsulfonyloxy having 6-10 carbon atoms;

with a compound of Formula III

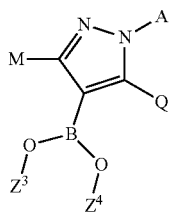

wherein

M, Q and A are as defined in claim 1;

$Z^3$ and $Z^4$ represent alkyl groups, with the possibility for $Z^3$ and $Z^4$ to form together a ring;

so as to obtain a compound of Formula IV,

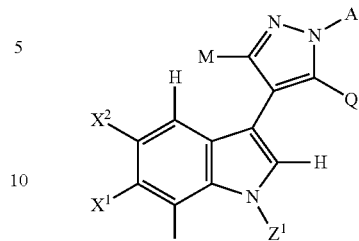

wherein $X^1$, $X^2$, M, Q, A and $Z^1$ are defined as above.

In certain other further embodiments the above described process further comprises a preliminary step of reacting a compound of Formula V,

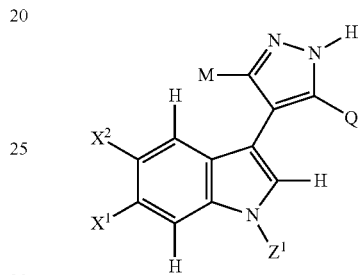

wherein $X^1$, $X^2$, M and Q are as defined in claim 1; and $Z^1$ represents an amino-protecting group selected from an arylsulphonyl, a tert-butoxy carbonyl, a methoxymethyl, a para-methoxy benzyl and a benzyl;

with a compound of Formula VI $$Z^5\text{-A}$$

wherein

A is as defined in claim 1; and $Z^5$ represents a leaving group selected from a halogen, alkylsulfonyloxy having 1-6 carbon atoms and arylsulfonyloxy having 6-10 carbon atoms;

so as to obtain a compound of Formula IV,

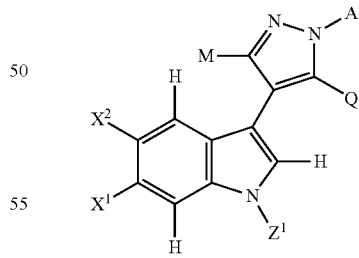

wherein $X^1$, $X^2$, M, Q, A and $Z^1$ are defined as above.

These and other aspects of the herein described invention embodiments will be evident upon reference to the following detailed description. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

DETAILED DESCRIPTION

Compounds

This invention relates in certain embodiments to compounds of Formula I:

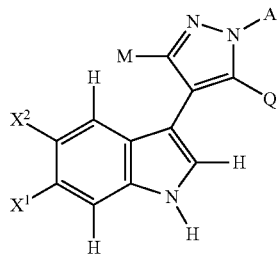

and pharmaceutically acceptable enantiomers, salts and solvates thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted by one or more substituents selected from the group comprising halogen, hydroxyl, $CONR^1R^2$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

A represents:

a hydrogen atom;

aryl, optionally substituted with halogen, hydroxyl, nitro, amido, carboxy, amino, cyano, haloalkoxy, haloalkyl, alkyl;

heteroaryl, optionally substituted with halogen, hydroxyl, nitro, amido, carboxy, amino, cyano, haloalkoxy, haloalkyl, alkyl; preferably substituted or unsubstituted pyridyl or pyridazine, more preferably substituted or unsubstituted pyridyl;

C1-C10 alkyl, linear or branched, optionally substituted with up to three substituents selected from the group comprising halogen, hydroxyl, $COOR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group, optionally substituted, selected from C1-C6 alkyl, aryl, heteroaryl, amino;

heterocyclyl, preferably saturated heteroaryl selected from azetidine, piperidine, morpholine, piperazine, tetrahydrofurane, tetrahydropyrane, tetrahydro-thiopyran-dioxide, dioxane, imidazolidinone, pyrrolidine, pyrrolidinone; optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$;

C1-C3 alkyl-heterocyclyl, preferably saturated heteroaryl selected from azetidine, piperidine, morpholine, piperazine, tetrahydrofurane, tetrahydropyrane, tetrahydro-thiopyran-dioxide, dioxane, imidazolidinone, pyrrolidine, pyrrolidinone; wherein both the C1-C3 alkyl and the heterocyclyl are optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group, optionally substituted, selected from C1-C6 alkyl, cycloalkyl, alkene, aryl, heteroaryl and amino, optionally substituted by one or more groups selected from halogen, hydroxyl, alkoxy, COOH, amino, $SO_2Me$;

cycloalkyl, preferably cyclobutane or cyclohexyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$;

C1-C3 alkyl-cycloalkyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a group selected from C1-C6 alkyl, cycloalkyl, alkene, aryl, heteroaryl and amino, optionally substituted by one or more groups selected from halogen, hydroxyl, alkoxy, COOH, amino, $SO_2Me$.

In one embodiment, preferred compounds of Formula I are those of Formula Ia:

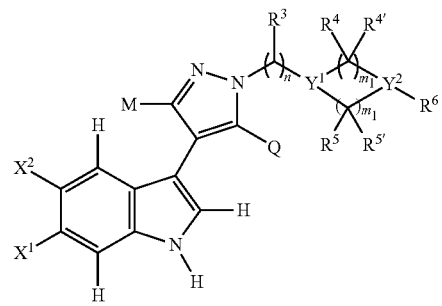

and pharmaceutically acceptable enantiomers, salts and solvates thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted by one or more substituents selected from the group comprising halogen, hydroxyl, CONR¹R², NR¹COR² wherein R¹ and R² represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

n represents an integer equal to 0, 1, 2 or 3;

$m_1$ and $m_2$ represent each independently an integer equal to 1 or 2;

$Y^1$ and $Y^2$ represent each independently $CR^7$, N, O, $SO_2$, wherein $R^7$ represents H or hydroxyl;

$R^3$ represents H, alkyl;

$R^4$, $R^{4'}$, $R^5$ and $R^{5'}$ represent each independently H, hydroxyl, alkyl, alkoxy, haloalkyl or $R^4$ and $R^{4'}$ form together an oxo moiety or $R^5$ and $R^{5'}$ form together an oxo moiety;

$R^6$ is absent or represents H, alkyl, the alkyl group being optionally substituted by one or more groups selected from halogen, hydroxyl or COOH; cycloalkyl, halogen, hydroxyl, oxo, $COR^1$, $COOR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$.

In one embodiment, preferred compounds of Formula I are those of Formula Ia-1:

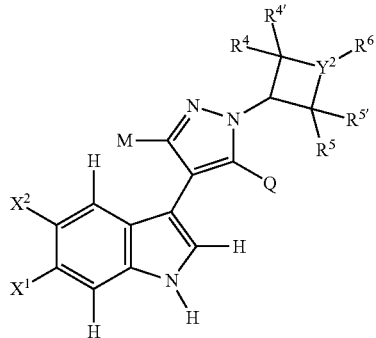

and pharmaceutically acceptable enantiomers, salts and solvates thereof, wherein:

$X^1$ and $X^2$ represent each independently H or F;

M and Q represent each independently H, C1-C6 alkyl optionally substituted by one or more halogen;

$Y^2$ represents N or CH;

$R^4$, $R^{4'}$, $R^5$ and $R^{5'}$ represent each independently H, hydroxyl, alkyl, alkoxy, haloalkyl or $R^4$ and $R^{4'}$ form together an oxo moiety or $R^5$ and $R^{5'}$ form together an oxo moiety, preferably $R^4$, $R^{4'}$, $R^5$ and $R^{5'}$ represent H or oxo;

$R^6$ represents H, alkyl, the alkyl group being optionally substituted by one or more groups selected from halogen, hydroxyl or COOH; cycloalkyl, halogen, hydroxyl, oxo, $COOR^1$, $COR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$; preferably $R^6$ represents H, COOH, COMe, $CONH_2$, CONHMe.

In one embodiment, preferred compounds of Formula I are those of Formula Ia-2:

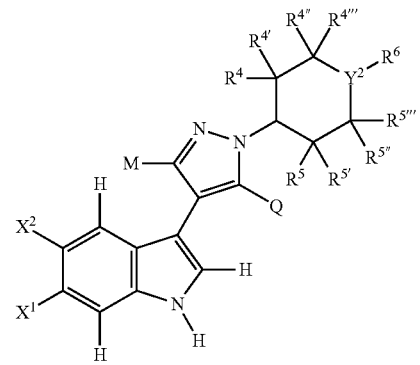

and pharmaceutically acceptable enantiomers, salts and solvates thereof, wherein:

$X^1$ and $X^2$ represent each independently H or F;

M and Q represent each independently H, C1-C6 alkyl optionally substituted one or more alogen;

$Y^2$ represents N or CH; preferably Y is N;

$R^4$, $R^{4'}$, $R^{4''}$, $R^{4'''}$, $R^5$, $R^{5'}$, $R^{5''}$ and $R^{5'''}$ represent each independently H, hydroxyl, alkyl, alkoxy, haloalkyl or $R^4$ and $R^{4'}$ form together an oxo moiety or $R^{4''}$ and $R^{4'''}$ form together an oxo moiety or $R^5$ and $R^{5'}$ form together an oxo moiety or $R^{5''}$ and $R^{5'''}$ form together an oxo moiety, preferably $R^4$, $R^{4'}$, $R^{4''}$, $R^{4'''}$, $R^5$, $R^{5'}$, $R^{5''}$ and $R^{5'''}$ represent H or oxo;

$R^6$ represents

H;

alkyl, the alkyl group being optionally substituted by one or more groups selected from halogen, hydroxyl or COOH; preferably methyl or —$CH_2$—$CH_2$—OH;

cycloalkyl;

halogen;

hydroxyl;

oxo;

$COR^1$, $SO_2R^1$, wherein $R^1$ represents a group selected from C1-C6 alkyl, preferably Me, Et, iPr, tBu; cycloalkyl, preferably cyclopropane; alkene, preferably ethylene; amino, preferably $NMe_2$; wherein $R^1$ groups are optionally substituted by one or more groups selected from halogen, preferably F; hydroxyl; alkoxy, preferably OMe; COOH; amino, preferably $NMe_2$ or $NH_2$; $SO_2Me$.

In one embodiment, preferred compounds of Formula I are those of Formula Ia-3:

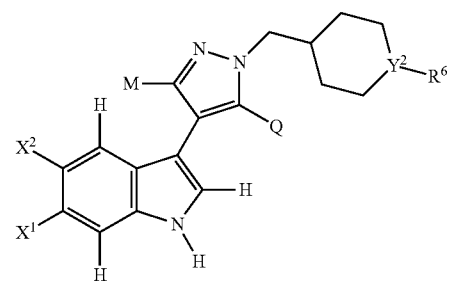

and pharmaceutically acceptable enantiomers, salts and solvates thereof, wherein:

$X^1$ and $X^2$ represent each independently H or F;

M and Q represent each independently H, C1-C6 alkyl optionally substituted one or more halogen;

$Y^2$ represents N or CH; preferably Y is N;

$R^6$ represents
H;
alkyl, the alkyl group being optionally substituted by one or more groups selected from halogen, hydroxyl or COOH;
cycloalkyl, preferably cyclopropane;
$COR^1$, $SO_2R^1$, wherein $R^1$ represents a group selected from C1-C6 alkyl, preferably methyl or ethyl; cycloalkyl; alkene; amino; wherein $R^1$ groups are optionally substituted by one or more groups selected from halogen; hydroxyl; alkoxy; COOH; amino; $SO_2Me$.

In one embodiment, preferred compounds of Formula I are those of Formula Ib:

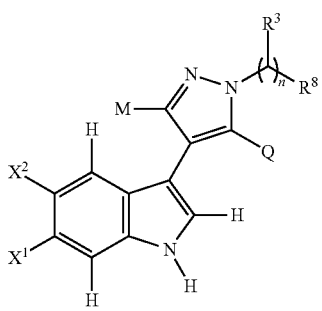

and pharmaceutically acceptable enantiomers, salts and solvates thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted by one or more substituents selected from the group comprising halogen, hydroxyl, $CONR^1R^2$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

n represents an integer equal to 1, 2 or 3, preferably 1 or 2;

$R^3$ represents H, alkyl;

$R^8$ represents H, alkyl, the alkyl group being optionally substituted by one or more groups selected from halogen, hydroxyl, COOH, $CONH_2$; cycloalkyl, halogen, hydroxyl, oxo, $COR^1$, $COOR^1$, $CONR^1R^2$, $NR^1COR^2$, $NR^1R^2$, $SO_2R^1$, $SO_2NR^1R^2$, $NR^1SO_2R^2$, $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, $SO_2Me$.

In one embodiment, preferred compounds of Formula I are those of Formula Ic:

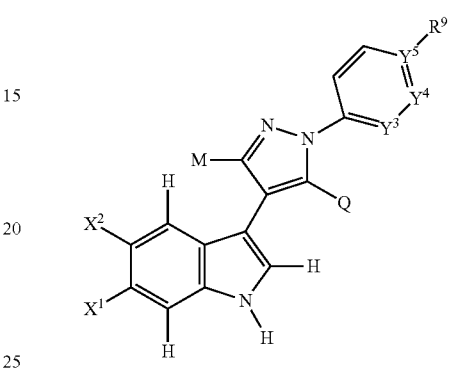

and pharmaceutically acceptable enantiomers, salts and solvates thereof, wherein:

$X^1$ and $X^2$ represent each independently H, halogen or haloalkyl, preferably H, F or $CF_3$, more preferably H or F;

M and Q represent each independently H, halogen, hydroxyl, C1-C6 alkyl optionally substituted one or more substituents selected from the group comprising halogen, hydroxyl, $CONR^1R^1$, $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, alkylheteroaryl; preferably M and Q represent each independently H, methyl or $CF_3$, more preferably H or methyl;

$Y^3$, $Y^4$, $Y^5$ represent each independently N or CH;

$R^9$ is absent or represents H; halogen, preferably Cl; amino, preferably $NH_2$.

In a preferred embodiment, in compounds of Formula Ic of the invention at least one of $Y^3$, $Y^4$, $Y^5$ represent N.

Particularly preferred compounds according to certain embodiments of Formula I of the invention are those listed in Table 1 hereafter.

TABLE 1

| Cpd n° | Structure | Chemical name | MW |
|---|---|---|---|
| 1 | ![structure] $C_{14}H_{11}FN_4O$ | 3-(4-(6-fluoro-1H-indol-3-yl)-1H-pyrazol-1-yl)azetidin-2-one | 270.26 |

TABLE 1-continued

| Cpd n° | Structure | Chemical name | MW |
|---|---|---|---|
| 2 | C₁₄H₁₃FN₄ | 3-(1-(azetidin-3-yl)-1H-pyrazol-4-yl)-6-fluoro-1H-indole | 256.28 |
| 3 | C₁₆H₁₅FN₄O | 1-(3-(4-(6-fluoro-1H-indol-3-yl)-1H-pyrazol-1-yl)azetidin-1-yl)ethanone | 298.31 |
| 4 | C₁₅H₁₄FN₅O | 3-(4-(6-fluoro-1H-indol-3-yl)-1H-pyrazol-1-yl)azetidine-1-carboxamide | 299.30 |
| 5 | C₁₆H₁₆FN₅O | 3-(4-(6-fluoro-1H-indol-3-yl)-1H-pyrazol-1-yl)-N-methylazetidine-1-carboxamide | 313.33 |
| 6 | C₁₅H₁₅FN₄ | 3-(1-(azetidin-3-ylmethyl)-1H-pyrazol-4-yl)-6-fluoro-1H-indole | 270.30 |

TABLE 1-continued
| Cpd n° | Structure | Chemical name | MW |
|---|---|---|---|
| 7 | 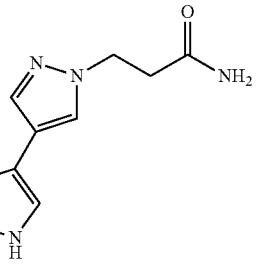 $C_{14}H_{13}FN_4O$ | 3-(4-(6-fluoro-1H-indol-3-yl)-1H-pyrazol-1-yl)propanamide | 272.28 |
| 8 | 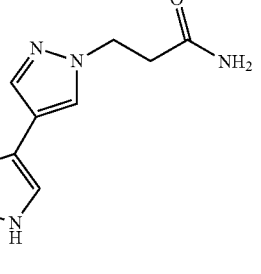 $C_{14}H_{12}F_2N_4O$ | 3-(4-(5,6-difluoro-1H-indol-3-yl)-1H-pyrazol-1-yl)propanamide | 290.27 |
| 9 | 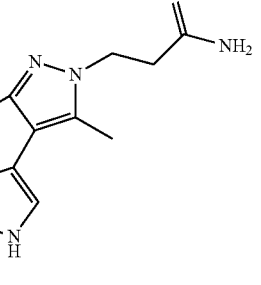 $C_{16}H_{17}FN_4O$ | 3-(4-(6-fluoro-1H-indol-3-yl)-3,5-dimethyl-1H-pyrazol-1-yl)propanamide | 300.33 |
| 10 | 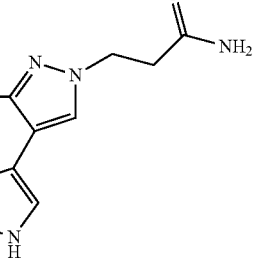 $C_{15}H_{15}FN_4O$ | 3-(4-(6-fluoro-1H-indol-3-yl)-3-methyl-1H-pyrazol-1-yl)propanamide | 286.30 |
| 11 | 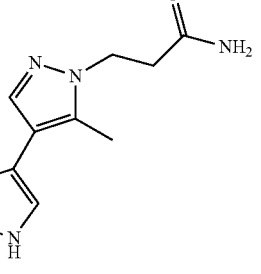 $C_{15}H_{15}FN_4O$ | 3-(4-(6-fluoro-1H-indol-3-yl)-5-methyl-1H-pyrazol-1-yl)propanamide | 286.30 |

TABLE 1-continued
| Cpd n° | Structure | Chemical name | MW |
|---|---|---|---|
| 12 | 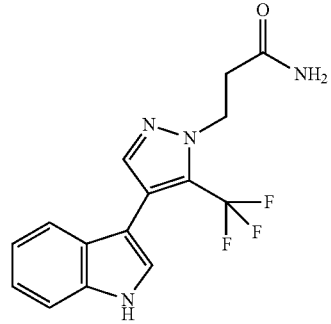<br>C₁₅H₁₃F₃N₄O | 3-(4-(1H-indol-3-yl)-5-(trifluoromethyl)-1H-pyrazol-1-yl)propanamide | 322.29 |
| 13 | 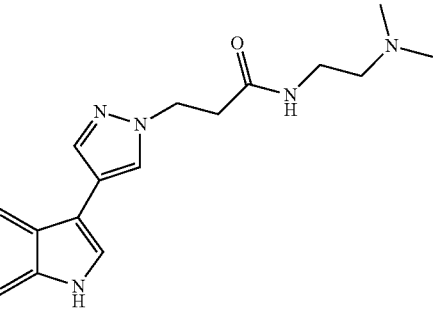<br>C₁₈H₂₂FN₅O | N-(2-(dimethylamino)ethyl)-3-(4-(6-fluoro-1H-indol-3-yl)-1H-pyrazol-1-yl)propanamide | 343.40 |
| 14 | 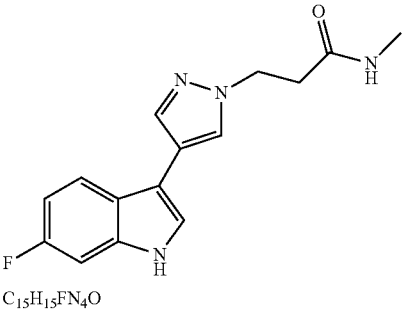<br>C₁₅H₁₅FN₄O | 3-(4-(6-fluoro-1H-indol-3-yl)-1H-pyrazol-1-yl)-N-methylpropanamide | 286.30 |
| 15 | 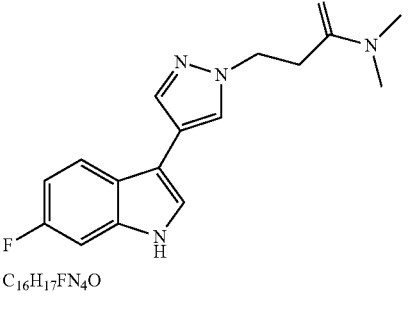<br>C₁₆H₁₇FN₄O | 3-(4-(6-fluoro-1H-indol-3-yl)-1H-pyrazol-1-yl)-N,N-dimethylpropanamide | 300.33 |

TABLE 1-continued
| Cpd n° | Structure | Chemical name | MW |
|---|---|---|---|
| 16 | 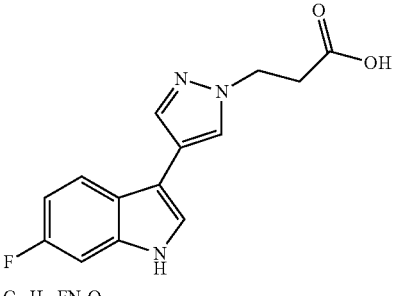<br>$C_{14}H_{12}FN_3O_2$ | 3-(4-(6-fluoro-1H-indol-3-yl)-1H-pyrazol-1-yl)propanoic acid | 273.26 |
| 17 | 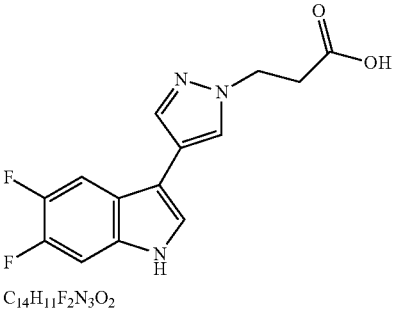<br>$C_{14}H_{11}F_2N_3O_2$ | 3-(4-(5,6-difluoro-1H-indol-3-yl)-1H-pyrazol-1-yl)propanoic acid | 291.25 |
| 18 | 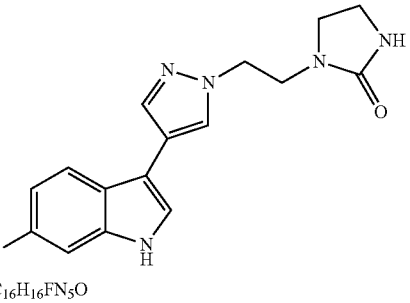<br>$C_{16}H_{16}FN_5O$ | 1-(2-(4-(6-fluoro-1H-indol-3-yl)-1H-pyrazol-1-yl)ethyl)imidazolidin-2-one | 313.33 |
| 19 | 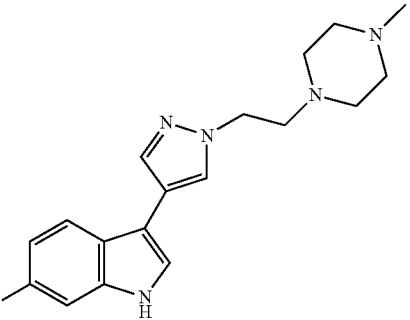<br>$C_{18}H_{22}FN_5$ | 6-fluoro-3-(1-(2-(4-methylpiperazin-1-yl)ethyl)-1H-pyrazol-4-yl)-1H-indole | 327.40 |

TABLE 1-continued
| Cpd n° | Structure | Chemical name | MW |
|---|---|---|---|
| 20 | 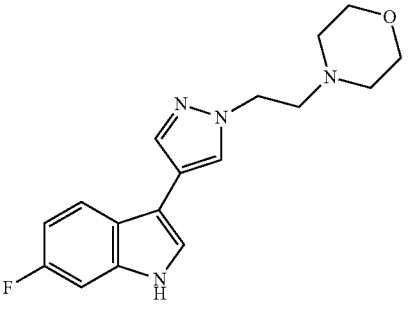 C17H19FN4O | 4-(2-(4-(6-fluoro-1H-indol-3-yl)-1H-pyrazol-1-yl)ethyl)morpholine | 314.36 |
| 21 | 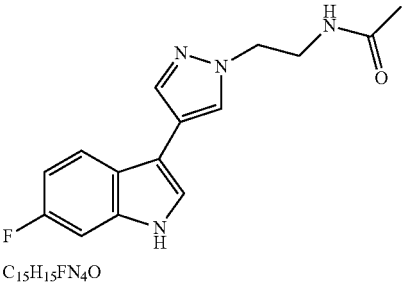 C15H15FN4O | N-(2-(4-(6-fluoro-1H-indol-3-yl)-1H-pyrazol-1-yl)ethyl)acetamide | 286.30 |
| 22 | 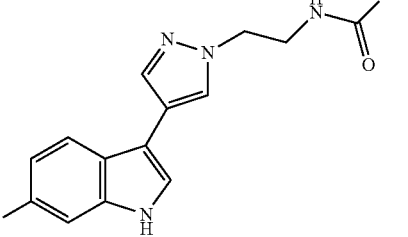 C14H14FN5O | 1-(2-(4-(6-fluoro-1H-indol-3-yl)-1H-pyrazol-1-yl)ethyl)urea | 287.29 |
| 23 | 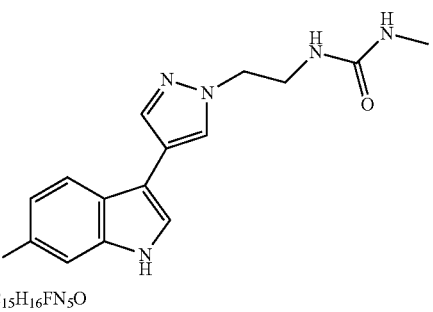 C15H16FN5O | 1-(2-(4-(6-fluoro-1H-indol-3-yl)-1H-pyrazol-1-yl)ethyl)-3-methylurea | 301.32 |
| 24 | 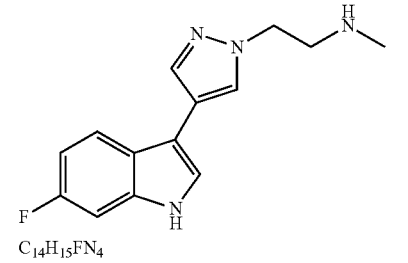 C14H15FN4 | 2-(4-(6-fluoro-1H-indol-3-yl)-1H-pyrazol-1-yl)-N-methylethanamine | 258.29 |

TABLE 1-continued
| Cpd n° | Structure | Chemical name | MW |
|---|---|---|---|
| 25 | 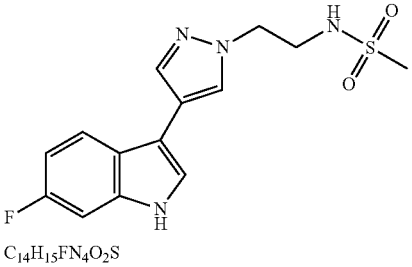 $C_{14}H_{15}FN_4O_2S$ | N-(2-(4-(6-fluoro-1H-indol-3-yl)-1H-pyrazol-1-yl)ethyl)methanesulfonamide | 322.36 |
| 26 | 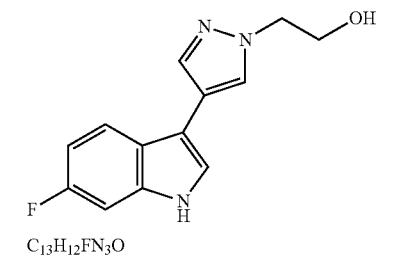 $C_{13}H_{12}FN_3O$ | 2-(4-(6-fluoro-1H-indol-3-yl)-1H-pyrazol-1-yl)ethanol | 245.25 |
| 27 | 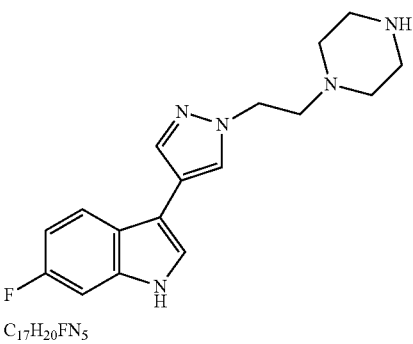 $C_{17}H_{20}FN_5$ | 6-fluoro-3-(1-(2-(piperazin-1-yl)ethyl)-1H-pyrazol-4-yl)-1H-indole | 313.37 |
| 28 | 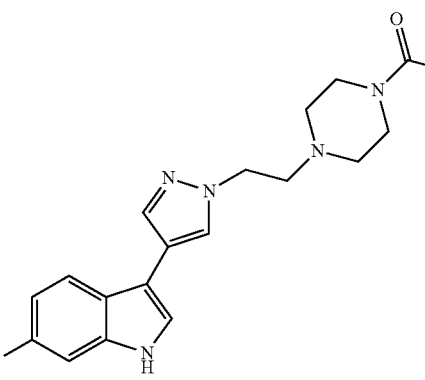 $C_{19}H_{22}FN_5O$ | 1-(4-(2-(4-(6-fluoro-1H-indol-3-yl)-1H-pyrazol-1-yl)ethyl)piperazin-1-yl)ethanone | 355.41 |
| 29 | 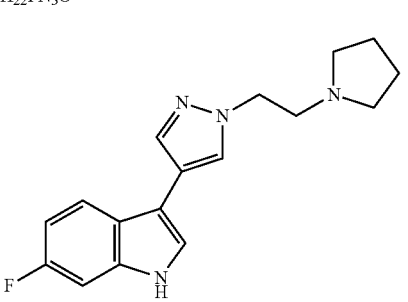 $C_{17}H_{19}FN_4$ | 6-fluoro-3-(1-(2-(pyrrolidin-1-yl)ethyl)-1H-pyrazol-4-yl)-1H-indole | 298.36 |

TABLE 1-continued

| Cpd n° | Structure | Chemical name | MW |
|---|---|---|---|
| 30 | C₁₇H₁₇FN₄O | 1-(2-(4-(6-fluoro-1H-indol-3-yl)-1H-pyrazol-1-yl)ethyl)pyrrolidin-2-one | 312.34 |
| 31 | C₁₄H₁₄FN₃O₂S | 6-fluoro-3-(1-(2-(methylsulfonyl)ethyl)-1H-pyrazol-4-yl)-1H-indole | 307.34 |
| 32 | C₁₄H₁₃F₂N₃O₂S | 5,6-difluoro-3-(1-(2-(methylsulfonyl)ethyl)-1H-pyrazol-4-yl)-1H-indole | 325.33 |
| 33 | C₁₆H₁₈FN₃O₂S | 3-(3,5-dimethyl-1-(2-(methylsulfonyl)ethyl)-1H-pyrazol-4-yl)-6-fluoro-1H-indole | 335.40 |

TABLE 1-continued

| Cpd n° | Structure | Chemical name | MW |
|---|---|---|---|
| 34 | 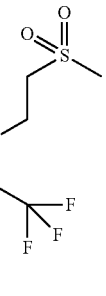<br>$C_{15}H_{14}F_3N_3O_2S$ | 3-(1-(2-(methylsulfonyl)ethyl)-5-(trifluoromethyl)-1H-pyrazol-4-yl)-1H-indole | 357.35 |
| 35 | <br>$C_{15}H_{15}FN_4OP$ | 3-(4-(6-fluoro-1H-indol-3-yl)-1H-pyrazol-1-yl)-2-methylpropanamide<br>(first eluted enantiomer) | 320.30 |
| 36 | <br>$C_{15}H_{15}FN_4OP_2$ | 3-(4-(6-fluoro-1H-indol-3-yl)-1H-pyrazol-1-yl)-2-methylpropanamide<br>(second eluted enantiomer) | 352.28 |
| 37 | 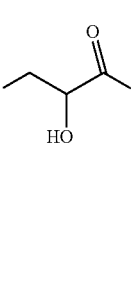<br>$C_{14}H_{13}FN_4O_2$ | 3-(4-(6-fluoro-1H-indol-3-yl)-1H-pyrazol-1-yl)-2-hydroxypropanamide | 288.28 |
| 38 | 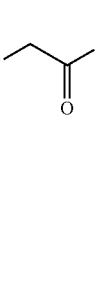<br>$C_{13}H_{11}FN_4O$ | 2-(4-(6-fluoro-1H-indol-3-yl)-1H-pyrazol-1-yl)acetamide | 258.25 |

TABLE 1-continued

| Cpd n° | Structure | Chemical name | MW |
|---|---|---|---|
| 39 | 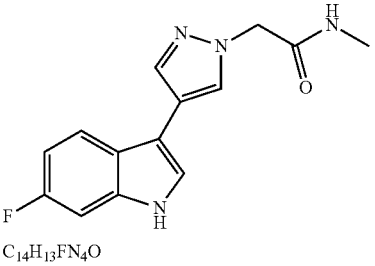<br>C₁₄H₁₃FN₄O | 2-(4-(6-fluoro-1H-indol-3-yl)-1H-pyrazol-1-yl)-N-methylacetamide | 272.28 |
| 40 | 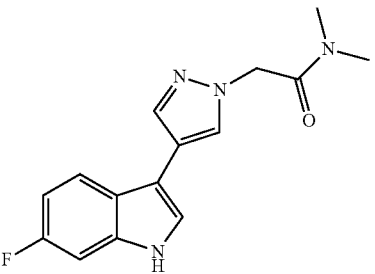<br>C₁₅H₁₅FN₄O | 2-(4-(6-fluoro-1H-indol-3-yl)-1H-pyrazol-1-yl)-N,N-dimethylacetamide | 286.30 |
| 41 | 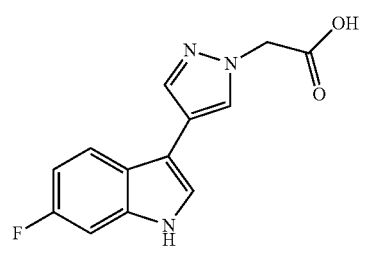<br>C₁₃H₁₀FN₃O₂ | 2-(4-(6-fluoro-1H-indol-3-yl)-1H-pyrazol-1-yl)acetic acid | 259.24 |
| 42 | 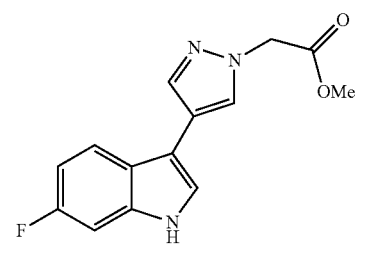<br>C₁₄H₁₂FN₃O₂ | methyl 2-(4-(6-fluoro-1H-indol-3-yl)-1H-pyrazol-1-yl)acetate | 273.26 |
| 43 | 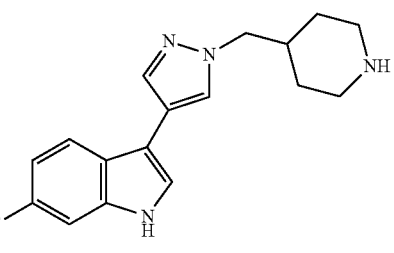<br>C₁₇H₁₉FN₄ | 6-fluoro-3-(1-(piperidin-4-ylmethyl)-1H-pyrazol-4-yl)-1H-indole | 298.36 |

TABLE 1-continued

| Cpd n° | Structure | Chemical name | MW |
|---|---|---|---|
| 44 | $C_{17}H_{18}F_2N_4$ | 5,6-difluoro-3-(1-(piperidin-4-ylmethyl)-1H-pyrazol-4-yl)-1H-indole | 316.35 |
| 45 | $C_{19}H_{20}F_4N_4$ | 6-fluoro-3-(1-((1-(2,2,2-trifluoroethyl)piperidin-4-yl)methyl)-1H-pyrazol-4-yl)-1H-indole | 380.38 |
| 46 | $C_{19}H_{22}F_2N_4$ | 6-fluoro-3-(1-((1-(2-fluoroethyl)piperidin-4-yl)methyl)-1H-pyrazol-4-yl)-1H-indole | 344.40 |
| 47 | $C_{19}H_{23}FN_4O$ | 2-(4-((4-(6-fluoro-1H-indol-3-yl)-1H-pyrazol-1-yl)methyl)piperidin-1-yl)ethanol | 342.41 |
| 48 | $C_{20}H_{22}F_4N_4O$ | 1,1,1-trifluoro-3-(4-((4-(6-fluoro-1H-indol-3-yl)-1H-pyrazol-1-yl)methyl)piperidin-1-yl)propan-2-ol | 410.41 |

TABLE 1-continued

| Cpd n° | Structure | Chemical name | MW |
|---|---|---|---|
| 49 | C₁₉H₂₁FN₄O₂ | 2-(4-((4-(6-fluoro-1H-indol-3-yl)-1H-pyrazol-1-yl)methyl)piperidin-1-yl)acetic acid | 356.39 |
| 50 | C₂₁H₂₃FN₄O₃ | 4-(4-((4-(6-fluoro-1H-indol-3-yl)-1H-pyrazol-1-yl)methyl)piperidin-1-yl)-4-oxobutanoic acid | 398.43 |
| 51 | C₁₉H₂₁FN₄O | 1-(4-((4-(6-fluoro-1H-indol-3-yl)-1H-pyrazol-1-yl)methyl)piperidin-1-yl)ethanone | 340.39 |
| 52 | C₂₀H₂₃FN₄ | 3-(1-((1-cyclopropylpiperidin-4-yl)methyl)-1H-pyrazol-4-yl)-6-fluoro-1H-indole | 338.42 |
| 53 | C₁₈H₂₁FN₄ | 6-fluoro-3-(1-((1-methylpiperidin-4-yl)methyl)-1H-pyrazol-4-yl)-1H-indole | 312.38 |

TABLE 1-continued

| Cpd n° | Structure | Chemical name | MW |
|---|---|---|---|
| 54 | C₁₈H₂₁FN₄O₂S | 6-fluoro-3-(1-((1-(methylsulfonyl)piperidin-4-yl)methyl)-1H-pyrazol-4-yl)-1H-indole | 376.45 |
| 55 | C₁₉H₂₃FN₄ | 3-(3,5-dimethyl-1-(piperidin-4-ylmethyl)-1H-pyrazol-4-yl)-6-fluoro-1H-indole | 326.41 |
| 56 | C₁₈H₂₁FN₄ | 6-fluoro-3-(3-methyl-1-(piperidin-4-ylmethyl)-1H-pyrazol-4-yl)-1H-indole | 312.38 |
| 57 | C₁₈H₂₁FN₄ | 6-fluoro-3-(5-methyl-1-(piperidin-4-ylmethyl)-1H-pyrazol-4-yl)-1H-indole | 312.38 |
| 58 | C₁₇H₁₈FN₃O | 6-fluoro-3-(1-((tetrahydro-2H-pyran-4-yl)methyl)-1H-pyrazol-4-yl)-1H-indole | 299.34 |

TABLE 1-continued

| Cpd n° | Structure | Chemical name | MW |
|---|---|---|---|
| 59 | 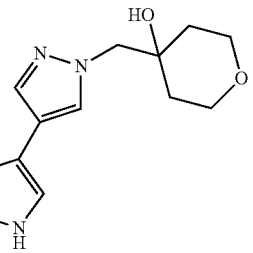<br>$C_{17}H_{18}FN_3O_2$ | 4-((4-(6-fluoro-1H-indol-3-yl)-1H-pyrazol-1-yl)methyl)tetrahydro-2H-pyran-4-ol | 315.34 |
| 60 | 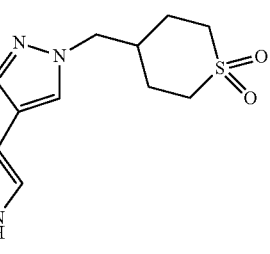<br>$C_{17}H_{18}FN_3O_2S$ | 4-((4-(6-fluoro-1H-indol-3-yl)-1H-pyrazol-1-yl)methyl)tetrahydro-2H-thiopyran 1,1-dioxide | 347.41 |
| 61 | 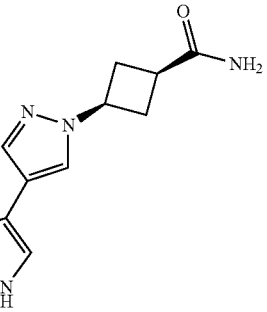<br>$C_{16}H_{15}FN_4O$ | (1S,3R)-3-(4-(6-fluoro-1H-indol-3-yl)-1H-pyrazol-1-yl)cyclobutanecarboxamide | 298.31 |
| 62 | 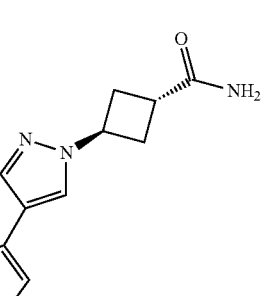<br>$C_{16}H_{15}FN_4O$ | (1R,3R)-3-(4-(6-fluoro-1H-indol-3-yl)-1H-pyrazol-1-yl)cyclobutanecarboxamide | 298.31 |
| 63 | 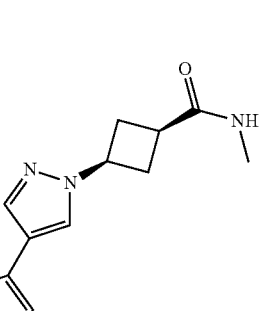<br>$C_{17}H_{17}FN_4O$ | (1S,3S)-3-(4-(6-fluoro-1H-indol-3-yl)-1H-pyrazol-1-yl)-N-methylcyclobutanecarboxamide | 312.34 |

TABLE 1-continued

| Cpd n° | Structure | Chemical name | MW |
|---|---|---|---|
| 64 | $C_{17}H_{17}FN_4O$ | (1R,3R)-3-(4-(6-fluoro-1H-indol-3-yl)-1H-pyrazol-1-yl)-N-methylcyclo-butanecarboxamide | 312.34 |
| 65 | $C_{16}H_{14}FN_3O_2$ | (1S,3S)-3-(4-(6-fluoro-1H-indol-3-yl)-1H-pyrazol-1-yl)cyclobutanecarboxylic acid | 299.30 |
| 66 | $C_{16}H_{14}FN_3O_2$ | (1R,3R)-3-(4-(6-fluoro-1H-indol-3-yl)-1H-pyrazol-1-yl)cyclobutanecarboxylic acid | 299.30 |
| 67 | $C_{18}H_{19}FN_4O$ | (1R,4R)-4-(4-(6-fluoro-1H-indol-3-yl)-1H-pyrazol-1-yl)cyclohexanecarboxamide | 326.37 |

TABLE 1-continued

| Cpd n° | Structure | Chemical name | MW |
|---|---|---|---|
| 68 | $C_{17}H_{18}FN_3O$ | (1R,4R)-4-(4-(6-fluoro-1H-indol-3-yl)-1H-pyrazol-1-yl)cyclohexanol | 299.34 |
| 69 | $C_{17}H_{18}FN_3O$ | (1R,4R)-4-(4-(6-fluoro-1H-indol-3-yl)-1H-pyrazol-1-yl)cyclohexanol | 299.34 |
| 70 | $C_{11}H_8FN_3$ | 6-fluoro-3-(1H-pyrazol-4-yl)-1H-indole | 201.20 |
| 71 | $C_{11}H_7F_2N_3$ | 5,6-difluoro-3-(1H-pyrazol-4-yl)-1H-indole | 219.19 |
| 72 | $C_{12}H_8F_3N_3$ | 3-(1H-pyrazol-4-yl)-6-(trifluoromethyl)-1H-indole | 251.21 |

TABLE 1-continued

| Cpd n° | Structure | Chemical name | MW |
|---|---|---|---|
| 73 | $C_{12}H_{10}FN_3$ | 6-fluoro-3-(1-methyl-1H-pyrazol-4-yl)-1H-indole | 215.23 |
| 74 | $C_{13}H_{12}FN_3$ | 3-(1,5-dimethyl-1H-pyrazol-4-yl)-6-fluoro-1H-indole | 229.25 |
| 75 | $C_{13}H_{12}FN_3$ | 3-(1,3-dimethyl-1H-pyrazol-4-yl)-6-fluoro-1H-indole | 229.25 |
| 76 | $C_{14}H_{14}FN_3$ | 6-fluoro-3-(1,3,5-trimethyl-1H-pyrazol-4-yl)-1H-indole | 243.28 |
| 77 | $C_{13}H_{10}F_3N_3$ | 3-(1-methyl-5-(trifluoromethyl)-1H-pyrazol-4-yl)-1H-indole | 265.23 |
| 78 | $C_{16}H_{17}FN_4$ | 6-fluoro-3-(1-(piperidin-4-yl)-1H-pyrazol-4-yl)-1H-indole | 284.33 |

TABLE 1-continued
| Cpd n° | Structure | Chemical name | MW |
|---|---|---|---|
| 79 | 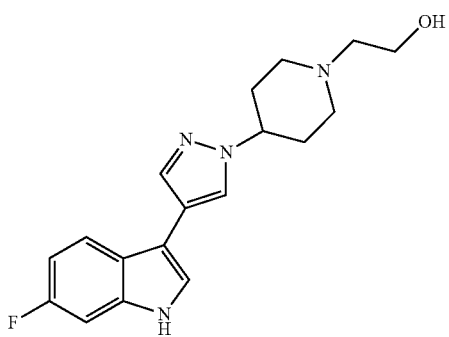 C₁₈H₂₁FN₄O | 2-(4-(4-(6-fluoro-1H-indol-3-yl)-1H-pyrazol-1-yl)piperidin-1-yl)ethanol | 328.38 |
| 80 | 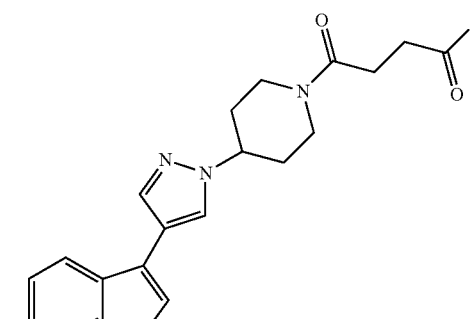 C₂₀H₂₁FN₄O₃ | 4-(4-(4-(6-fluoro-1H-indol-3-yl)-1H-pyrazol-1-yl)piperidin-1-yl)-4-oxobutanoic acid | 384.40 |
| 81 | 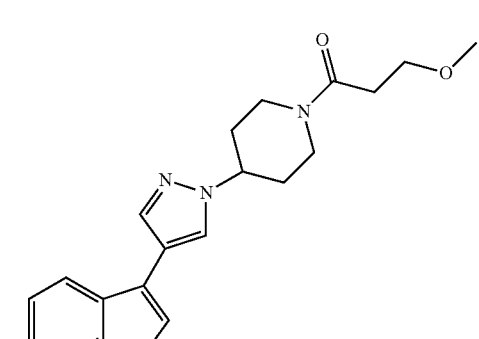 C₂₀H₂₃FN₄O₂ | 1-(4-(4-(6-fluoro-1H-indol-3-yl)-1H-pyrazol-1-yl)piperidin-1-yl)-3-methoxypropan-1-one | 370.42 |
| 82 | 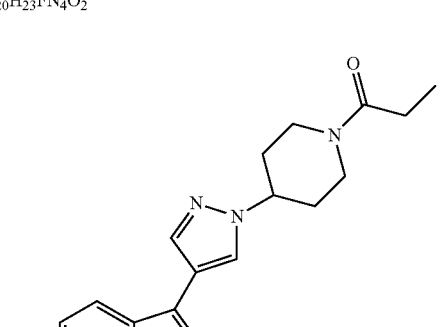 C₁₉H₂₁FN₄O | 1-(4-(4-(6-fluoro-1H-indol-3-yl)-1H-pyrazol-1-yl)piperidin-1-yl)propan-1-one | 340.39 |

TABLE 1-continued

| Cpd n° | Structure | Chemical name | MW |
|---|---|---|---|
| 83 | 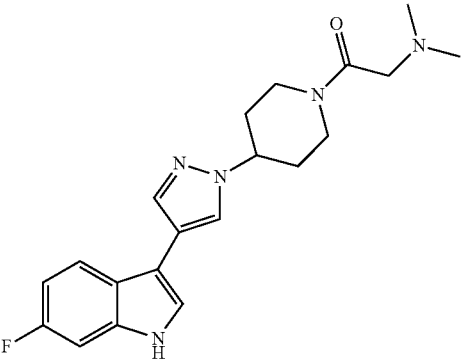<br>C₂₀H₂₄FN₅O | 2-(dimethylamino)-1-(4-(4-(6-fluoro-1H-indol-3-yl)-1H-pyrazol-1-yl)piperidin-1-yl)ethanone | 369.44 |
| 84 | 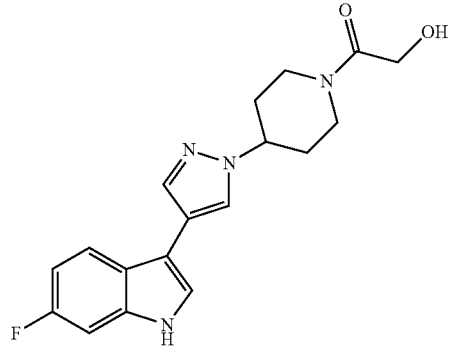<br>C₁₈H₁₉FN₄O₂ | 1-(4-(4-(6-fluoro-1H-indol-3-yl)-1H-pyrazol-1-yl)piperidin-1-yl)-2-hydroxyethanone | 342.37 |
| 85 | 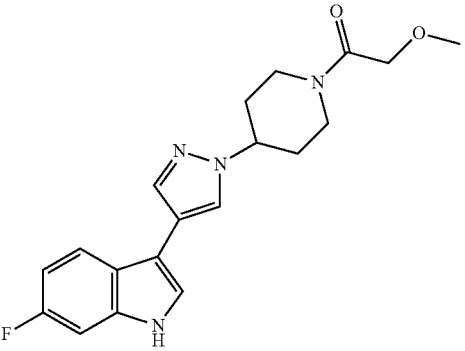<br>C₁₉H₂₁FN₄O₂ | 1-(4-(4-(6-fluoro-1H-indol-3-yl)-1H-pyrazol-1-yl)piperidin-1-yl)-2-methoxyethanone | 356.39 |
| 86 | 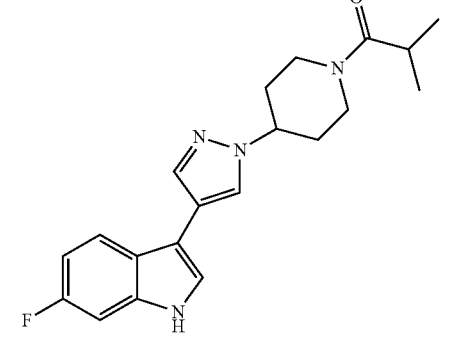<br>C₂₀H₂₃FN₄O | 1-(4-(4-(6-fluoro-1H-indol-3-yl)-1H-pyrazol-1-yl)piperidin-1-yl)-2-methylpropan-1-one | 354.42 |

TABLE 1-continued

| Cpd n° | Structure | Chemical name | MW |
|---|---|---|---|
| 87 | C$_{21}$H$_{25}$FN$_4$O | 1-(4-(4-(6-fluoro-1H-indol-3-yl)-1H-pyrazol-1-yl)piperidin-1-yl)-2,2-dimethylpropan-1-one | 368.45 |
| 88 | C$_{20}$H$_{21}$FN$_4$O | cyclopropyl(4-(4-(6-fluoro-1H-indol-3-yl)-1H-pyrazol-1-yl)piperidin-1-yl)methanone | 352.41 |
| 89 | C$_{18}$H$_{19}$FN$_4$O | 1-(4-(4-(6-fluoro-1H-indol-3-yl)-1H-pyrazol-1-yl)piperidin-1-yl)ethanone | 326.37 |
| 90 | C$_{19}$H$_{22}$FN$_5$O | 4-(4-(6-fluoro-1H-indol-3-yl)-1H-pyrazol-1-yl)-N,N-dimethylpiperidine-1-carboxamide | 355.41 |

TABLE 1-continued

| Cpd n° | Structure | Chemical name | MW |
|---|---|---|---|
| 91 | C₁₇H₁₉FN₄ | 6-fluoro-3-(1-(1-methylpiperidin-4-yl)-1H-pyrazol-4-yl)-1H-indole | 298.36 |
| 92 | C₁₇H₁₆F₄N₄O₂S | 6-fluoro-3-(1-(1-((trifluoromethyl)sulfonyl)piperidin-4-yl)-1H-pyrazol-4-yl)-1H-indole | 416.39 |
| 93 | C₁₉H₁₉F₃N₄O | 1-(4-(4-(1H-indol-3-yl)-5-(trifluoromethyl)-1H-pyrazol-1-yl)piperidin-1-yl)ethanone | 376.38 |
| 94 | C₁₉H₂₁FN₄O | 1-(4-(4-(6-fluoro-1H-indol-3-yl)-3-methyl-1H-pyrazol-1-yl)piperidin-1-yl)ethanone | 340.39 |

TABLE 1-continued

| Cpd n° | Structure | Chemical name | MW |
|---|---|---|---|
| 95 | $C_{19}H_{21}FN_4O$ | 1-(4-(4-(6-fluoro-1H-indol-3-yl)-5-methyl-1H-pyrazol-1-yl)piperidin-1-yl)ethanone | 340.39 |
| 96 | $C_{19}H_{23}FN_4O_3S$ | 6-fluoro-3-(1-(1-((2-methoxyethyl)sulfonyl)piperidin-4-yl)-1H-pyrazol-4-yl)-1H-indole | 406.47 |
| 97 | $C_{19}H_{21}FN_4O_2S$ | 3-(1-(1-(cyclopropylsulfonyl)piperidin-4-yl)-1H-pyrazol-4-yl)-6-fluoro-1H-indole | 388.46 |
| 98 | $C_{18}H_{21}FN_4O_2S$ | 3-(1-(1-(ethylsulfonyl)piperidin-4-yl)-1H-pyrazol-4-yl)-6-fluoro-1H-indole | 376.45 |

TABLE 1-continued

| Cpd n° | Structure | Chemical name | MW |
|---|---|---|---|
| 99 | C₁₉H₂₃FN₄O₂S | 6-fluoro-3-(1-(1-(isopropylsulfonyl)piperidin-4-yl)-1H-pyrazol-4-yl)-1H-indole | 390.47 |
| 100 | C₁₆H₁₅FN₄O | 4-(4-(6-fluoro-1H-indol-3-yl)-1H-pyrazol-1-yl)piperidin-2-one | 298.31 |
| 101 | C₁₇H₁₇FN₄O | 4-(4-(6-fluoro-1H-indol-3-yl)-1H-pyrazol-1-yl)-1-methylpiperidin-2-one | 312.34 |
| 102 | C₁₉H₁₉FN₄O | 1-(4-(4-(6-fluoro-1H-indol-3-yl)-1H-pyrazol-1-yl)piperidin-1-yl)prop-2-en-1-one | 338.38 |

TABLE 1-continued

| Cpd n° | Structure | Chemical name | MW |
|---|---|---|---|
| 103 | C21H25FN4O3S | 1-(4-(4-(6-fluoro-1H-indol-3-yl)-1H-pyrazol-1-yl)piperidin-1-yl)-4-(methylsulfonyl)butan-1-one | 432.51 |
| 104 | C19H21FN4O2 | 1-(4-(4-(6-fluoro-1H-indol-3-yl)-1H-pyrazol-1-yl)piperidin-1-yl)-3-hydroxypropan-1-one | 356.39 |
| 105 | C20H23FN4O3S | 1-(4-(4-(6-fluoro-1H-indol-3-yl)-1H-pyrazol-1-yl)piperidin-1-yl)-3-(methylsulfonyl)propan-1-one | 418.49 |
| 106 | C17H19FN4O2S | 6-fluoro-3-(1-(1-(methylsulfonyl)piperidin-4-yl)-1H-pyrazol-4-yl)-1H-indole | 362.42 |

TABLE 1-continued

| Cpd n° | Structure | Chemical name | MW |
|---|---|---|---|
| 107 | $C_{15}H_{10}FN_5$ | 6-fluoro-3-(1-(pyridazin-3-yl)-1H-pyrazol-4-yl)-1H-indole | 279.27 |
| 108 | $C_{15}H_9ClFN_5$ | 3-(1-(6-chloropyridazin-3-yl)-1H-pyrazol-4-yl)-6-fluoro-1H-indole | 313.72 |
| 109 | $C_{15}H_{11}FN_6$ | 6-(4-(6-fluoro-1H-indol-3-yl)-1H-pyrazol-1-yl)pyridazin-3-amine | 294.29 |
| 110 | $C_{15}H_{10}FN_5$ | 6-fluoro-3-(1-(pyridazin-4-yl)-1H-pyrazol-4-yl)-1H-indole | 279.27 |

TABLE 1-continued

| Cpd n° | Structure | Chemical name | MW |
|---|---|---|---|
| 111 | C₁₆H₁₁FN₄ | 6-fluoro-3-(1-(pyridin-2-yl)-1H-pyrazol-4-yl)-1H-indole | 278.28 |
| 112 | C₁₆H₁₁FN₄ | 6-fluoro-3-(1-(pyridin-3-yl)-1H-pyrazol-4-yl)-1H-indole | 278.28 |
| 113 | C₁₆H₁₁FN₄ | 6-fluoro-3-(1-(pyridin-4-yl)-1H-pyrazol-4-yl)-1H-indole | 278.28 | or pharmaceutically acceptable enantiomers, salts and solvates thereof.

In Table 1, the term "Cpd" means compound.

The compounds of Table 1 were named using ChemBioDraw® Ultra version 12.0 (PerkinElmer).

The compounds of Formula I and subformulae thereof may contain an asymmetric center and thus may exist as different stereoisomeric forms. Accordingly, the present invention includes in certain embodiments all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of certain embodiments of the invention may be in the form of pharmaceutically acceptable salts. Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When in certain embodiments the compounds of the invention contain an acidic group as well as a basic group, the compounds may also form internal salts, and such compounds are within the scope of the invention. When in certain embodiments the compounds of the invention contain a hydrogen-donating heteroatom (e.g. NH), the encompassed invention embodiments also include salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds according to certain embodiments of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of these and related embodiments, pharmaceutically acceptable salts of the compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

All references to compounds of formula I include references to enantiomers, salts, solvates, polymorphs, multi-component complexes and liquid crystals thereof.

The compounds according to certain embodiments of the invention include compounds of formula I as hereinbefore defined, including all polymorphs and crystal habits thereof, prodrugs and isomers thereof (including optical, geometric and tautomeric isomers) and isotopically-labeled compounds of formula I.

In addition, although generally, with respect to the salts of the compounds of the herein disclosed invention embodiments, pharmaceutically acceptable salts are preferred, it should be noted that according to certain contemplated embodiments the invention in its broadest sense also includes non-pharmaceutically acceptable salts, which may for example be used in the isolation and/or purification of the compounds. For example, salts formed with optically active acids or bases may be used to form diastereoisomeric salts that can facilitate the separation of optically active isomers of the compounds of Formula I above.

The invention in certain embodiments also generally encompasses all pharmaceutically acceptable predrugs and prodrugs of the compounds of Formula I.

Process for Manufacturing

The compounds of Formula I can be prepared by different ways with reactions known to a person skilled in the art.

Certain embodiments of the invention further relate to a process for manufacturing of compounds of Formula I,

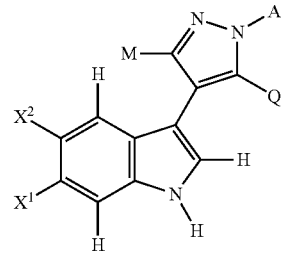

and pharmaceutically acceptable enantiomers, salts and solvates thereof, wherein $X^1$, $X^2$, M, Q and A are as defined above;

comprising deprotecting the indole amine of compound of Formula IV:

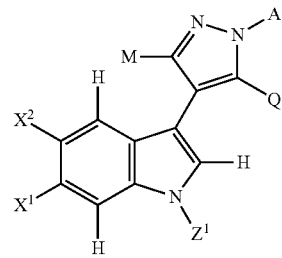

wherein

X$^1$, X$^2$, M, Q and A are as defined above; and

Z$^1$ represents an amino-protecting group such as for example an arylsulphonyl, a tert-butoxy carbonyl, a methoxymethyl, a para-methoxy benzyl, a benzyl or any other suitable protecting group known by those skilled in the art;

to afford compound of Formula I.

According to one embodiment, deprotection step of the process of the invention, depending on the nature of the group Z$^1$, may be performed by treatment with bases, such as but not limited to sodium hydroxide, potassium hydroxide, potassium carbonate, in the presence or absence of a suitable solvent such as but not limited to methanol, ethanol, isopropanol, tert-butanol, THF, DMF, dioxane, water or a mixture thereof, at a temperature between about 20° C. to about 100° C., preferably at about 85° C., for a few hours, e.g. one hour to 24 h. Alternatively, depending on the nature of the group Z$^1$, step b) may be performed in the presence of strong acids, such as but not limited to HCl, TFA, HF, HBr, in the presence or absence of a suitable solvent such as methanol, ethanol, isopropanol, tert-butanol, THF, DMF, Dioxane, water or a mixture thereof, at a temperature between about 20° C. to about 100° C., for a period comprised between 10 minutes and a few hours, e.g. 10 minutes to 24 h.

According to one embodiment, the process of the invention further comprises a preliminary step, selected for step (a1) or step (a2), according to the following general scheme:

The invention relates in certain embodiments to a first process of manufacturing of compounds of Formula I, according to the following general scheme:

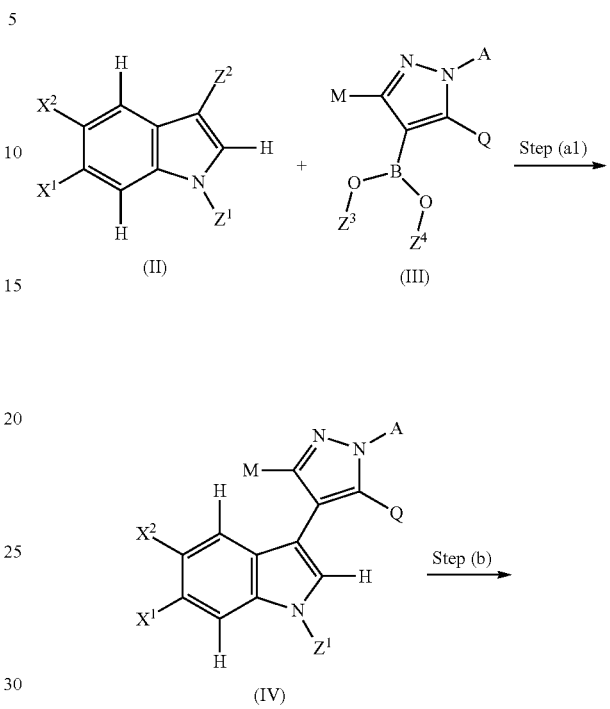

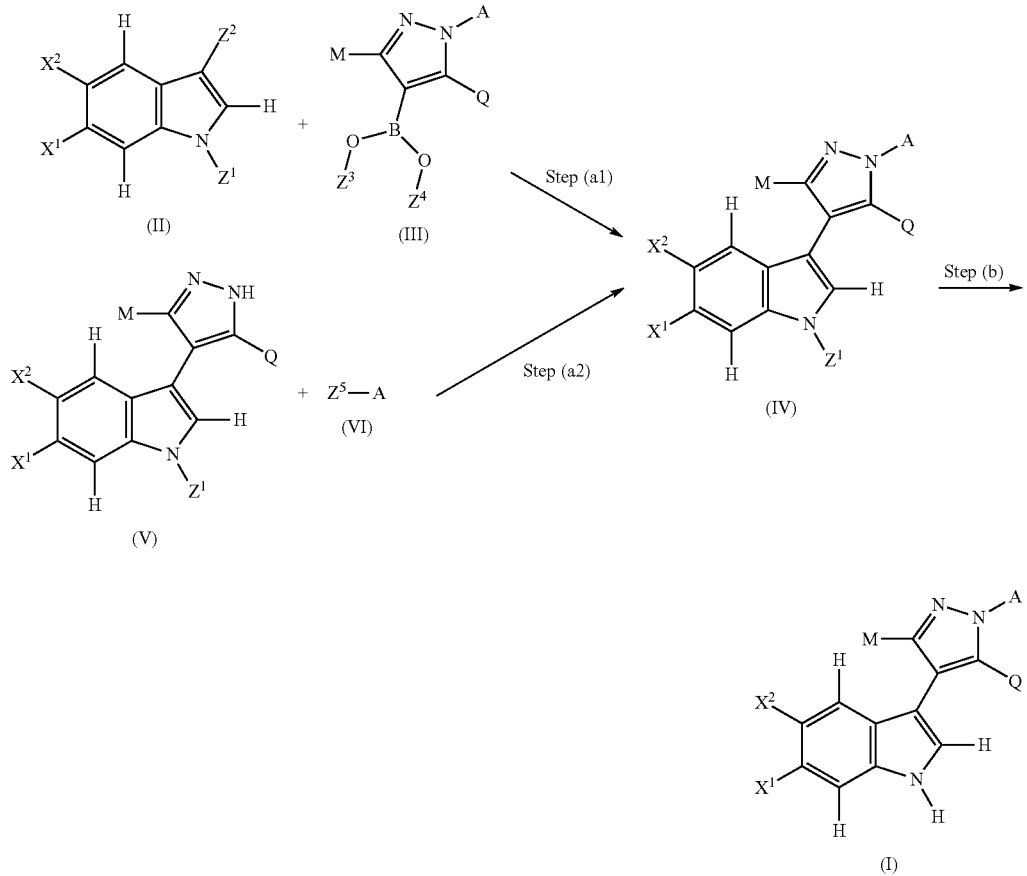

-continued

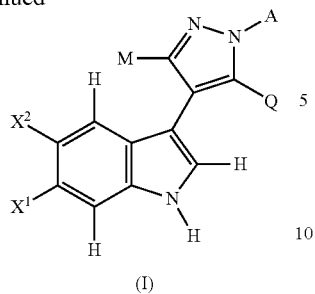

(I)

According to an embodiment, the first process of manufacturing of compounds of Formula I:

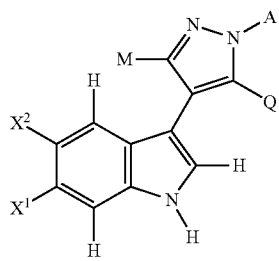

and pharmaceutically acceptable enantiomers, salts and solvates thereof, wherein $X^1$, $X^2$, M, Q and A are as defined above;
is characterized in that it comprises the following steps:
(a1) reacting a compound of Formula II,

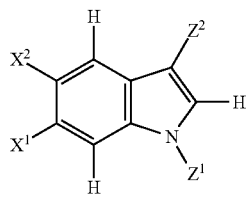

wherein
$X^1$ and $X^2$ are defined as above;
$Z^1$ represents an amino-protecting group such as for example an arylsulphonyl, a tert-butoxy carbonyl, a methoxymethyl, a para-methoxy benzyl, a benzyl or any other suitable protecting group known by those skilled in the art;
$Z^2$ represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy);
with a compound of Formula III

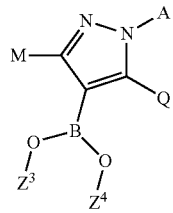

wherein
M, Q and A are defined as above;
$Z^3$ and $Z^4$ represent alkyl groups, with the possibility for $Z^3$ and $Z^4$ to form together a ring;

so as to obtain a compound of Formula IV,

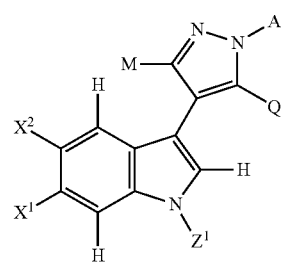

wherein $X^1$, $X^2$, M, Q, A and $Z^1$ are defined as above;
(b) deprotecting the indole amine of compound of Formula IV, to afford compound of Formula I.

According to one embodiment, step (a1) of the process of the invention may be performed with or without a catalyst such as but not limited to $Pd_2(dba)_3$, $Pd(PPh_3)_4$, dichlorobis(triphenylphosphine)palladium(II) or 1,1'-bis(diphenylphosphino)ferrocenedichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a1) of the process of the invention is preferably performed in the presence of bases such as but not limited to $K_3PO_4$, $K_2CO_3$, $Na_2CO_3$.

According to one embodiment, step (a1) of the process of the invention is preferably performed in the presence of a suitable solvent such as but not limited to dioxane, THF, DMF, water or mixtures thereof, preferably in a mixture of dioxane or THF and water.

According to one embodiment, step (a1) of the process of the invention may be carried out at a temperature ranging from about 20° C. to about 180° C., with or without microwave irradiation, for a period ranging from 10 minutes to a few hours, preferably from 10 minutes to 24 h.

The invention further relates in certain embodiments to a second process of manufacturing of compounds of Formula I, according to the following general scheme:

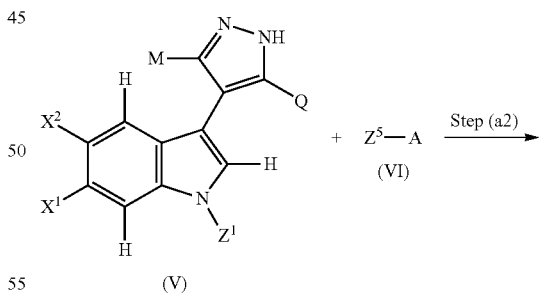

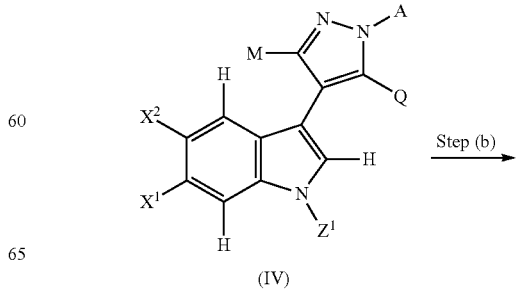

-continued

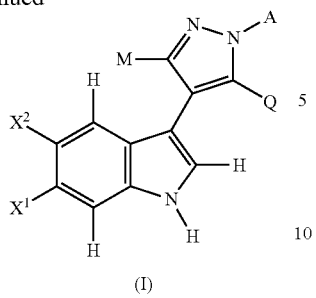

(I)

so as to obtain a compound of Formula IV,

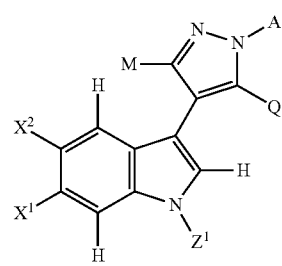

wherein $X^1$, $X^2$, M, Q, A and $Z^1$ are defined as above;

(b) deprotecting the indole amine of compound of Formula IV, to afford compound of Formula I.

According to one embodiment, step (a2) of the process of the invention may be performed in the presence of bases such as but not limited to cesium carbonate, sodium carbonate, potassium carbonate, sodium hydride, sodium hydroxide, potassium hydroxide.

According to one embodiment, step (a2) of the process of the invention may be performed in the presence of a suitable solvent such as but not limited to DMF, methanol, ethanol, isopropanol, tert-butanol, THF, dioxane, dichloromethane, water.

According to one embodiment, step (a2) of the process of the invention may be performed in the presence or absence of catalytic amounts of appropriate iodide salts, such as but not limited to tetrabutylammonium iodide.

According to one embodiment, step (a2) of the process of the invention may be carried out at a temperature between about 20° C. to about 180° C., with or without microwave irradiation, for a period comprised between 10 minutes and a few hours, e.g. 10 minutes to 24 h.

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

According to an embodiment, the first process of manufacturing of compounds of Formula I:

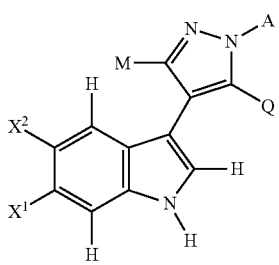

and pharmaceutically acceptable enantiomers, salts and solvates thereof, wherein $X^1$, $X^2$, M, Q and A are as defined above;

is characterized in that it comprises the following steps:

(a2) reacting a compound of Formula V,

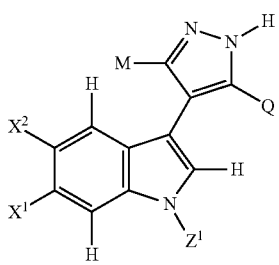

wherein $X^1$, $X^2$, M and Q are defined as above; and $Z^1$ represents an amino-protecting group such as for example an arylsulphonyl, a tert-butoxy carbonyl, a methoxymethyl, a para-methoxy benzyl, a benzyl or any other suitable protecting group known by those skilled in the art;

with a compound of Formula VI $Z^5$-A wherein

A is defined as above; and $Z^5$ represents an halogen (preferably iodine, bromine or chlorine), alkylsulfonyloxy having 1-6 carbon atoms (preferably methylsulfonyloxy or trifluoro-methylsulfonyloxy) or arylsulfonyloxy having 6-10 carbon atoms (preferably phenyl- or p-tolylsulfonyloxy), or any other leaving group known to those skilled in the art;

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Applications

The invention is in certain embodiments further directed to the use of the herein disclosed compounds or pharmaceutically acceptable enantiomers, salts and solvates thereof as TDO2 inhibitors.

Accordingly, in a particularly preferred embodiment, the invention relates to the use of compounds of Formula I and subformulae in particular those of Table 1 above, or pharmaceutically acceptable enantiomers, salts and solvates thereof, as TDO2 inhibitors.

Accordingly, in another aspect or embodiment, the invention relates to the use of these compounds or enantiomers, salts and solvates thereof for the synthesis of pharmaceutical active ingredients, such as TDO2 inhibitors.

In one embodiment, the invention relates to the use of compounds of Formula I and subformulae in particular those of Table 1 above, or pharmaceutically acceptable enantiomers, salts and solvates thereof, for increasing immune recognition and destruction of the cancer cells.

The compounds of certain herein disclosed embodiments of the invention are therefore useful as medicaments, in particular in reducing (e.g., in a statistically significant manner relative to an appropriate control) the likelihood of occurrence of cancer and/or in the prevention and/or treatment of cancer.

In one embodiment, compounds of the invention or pharmaceutically acceptable enantiomers, salts or solvates thereof are for use in the treatment and/or in reducing (e.g., in a statistically significant manner relative to an appropriate control) the likelihood of occurrence of and/or in prevention of cancer, neurodegenerative disorders such as Parkinson's disease, Alzheimer's disease and Huntington's disease, chronic viral infections such as HCV and HIV, depression, and obesity.

The invention further relates in certain embodiments to a method for treatment or prevention or reducing likelihood of occurrence of cancer, neurodegenerative disorders such as Parkinson's disease, Alzheimer's disease and Huntington's disease, chronic viral infections such as HCV and HIV, depression, and obesity, which comprises administering to a mammalian species in need thereof a therapeutically effective amount of the herein disclosed compound according to the present invention embodiments or a pharmaceutically acceptable enantiomers, salts or solvates thereof.

Various cancers are known in the art. The cancer may be metastatic or non-metastatic. The cancer may be may be familial or sporadic. In some embodiments, the cancer is selected from the group consisting of: leukemia and multiple myeloma. Additional cancers that can be treated using the methods of the embodiments disclosed herein include, for example, benign and malignant solid tumours and benign and malignant non-solid tumours. The presence of cancer or a malignant condition in a subject refers to the presence of dysplastic, cancerous and/or transformed cells in the subject, including, for example neoplastic, tumor, non-contact inhibited or oncogenically transformed cells, or the like which are known to the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3).

Examples of solid tumours include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumours (seminomas, and non-seminomas such as teratomas and choriocarcinomas), stromal tumours, germ cell tumours, and thyroid cancer (including thyroid adenocarcinoma and medullary carcinoma).

Examples of non-solid tumours include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

The invention in certain embodiments also provides for a method for delaying in patient the onset of cancer comprising the administration of a pharmaceutically effective amount of a compound of Formula I or pharmaceutically acceptable enantiomer, salt and solvate thereof to a patient in need thereof.

Preferably, the patient is a warm-blooded animal, more preferably a human.

The compounds according to certain embodiments of the invention are especially useful in reducing the likelihood of occurrence of and/or in the treatment and/or prevention of cancer.

In a specific embodiment, the compounds of the invention are especially useful in the treatment and/or reducing the likelihood of occurrence of and/or prevention of cancer.

The invention in certain embodiments further provides the use of a compound of Formula I or a pharmaceutically acceptable enantiomer, salt and solvate thereof for the manufacture of a medicament for treating and/or reducing the likelihood of occurrence of and/or preventing cancer.

According to a further feature of certain embodiments according to the present invention there is provided a method for modulating TDO2 activity, in a patient, preferably a warm blooded animal, and even more preferably a human, in need of such treatment, which comprises administering to said patient an effective amount of a compound of the present disclosure, or a pharmaceutically acceptable enantiomer, salt and solvate thereof.

Formulations

The invention in certain embodiments also provides pharmaceutical compositions comprising a compound of Formula I or a pharmaceutically acceptable enantiomer, salt and solvate thereof and at least one pharmaceutically acceptable carrier, diluent, excipient and/or adjuvant. As indicated above, the invention embodiments also encompass pharmaceutical compositions which contain, in addition to a compound of the present invention disclosure, a pharmaceutically acceptable enantiomer, salt and solvate thereof as active ingredient, additional therapeutic agents and/or active ingredients.

Another object according to certain embodiments of this invention is a medicament comprising at least one compound of the invention, or a pharmaceutically acceptable enantiomer, salt and solvate thereof, as active ingredient.

According to a further feature of certain embodiments of the present invention there is provided the use of a compound of Formula I or a pharmaceutically acceptable enantiomer, salt and solvate thereof for the manufacture of a medicament for modulating TDO2 activity in a patient, in need of such treatment, which comprises administering to said patient an effective amount of the compound, or a pharmaceutically acceptable enantiomer, salt and solvate thereof.

Generally, for pharmaceutical use, the compounds may be formulated as a pharmaceutical preparation comprising at least one compound and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations according to certain embodiments of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated or for which the likelihood of occurrence is to be reduced (e.g., in a statistically significant manner relative to an appropriate control) and the route of administration, the active compound of the invention may be administered as a single daily dose, divided over one or more daily doses, or essentially continuously, e.g., using a drip infusion.

DEFINITIONS

In the present disclosure, the following terms have the following meanings:

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl.

The term "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

The term "haloalkyl" alone or in combination, refers to an alkyl radical having the meaning as defined above wherein one or more hydrogens are replaced with a halogen as defined above. Non-limiting examples of such haloalkyl radicals include fluoromethyl, difluoromethyl, trifluoro methyl and the like.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

Where at least one carbon atom in a cycloalkyl group is replaced with a heteroatom, the resultant ring is referred to herein as "heterocyclyl".

The terms "heterocyclyl" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include piperidinyl, azetidinyl, tetrahydropyranyl, piperazinyl, imidazolinyl, morpholinyl, oxetanyl, pyrazolidinyl imidazolidinyl, isoxazolinyl, oxazolidinyl, isoxazolidinyl, thiazolidinyl, isothiazolidinyl, indolyl, indolinyl, isoindolinyl, tetrahydrofuranyl, tetrahydroquinolinyl, thiomorpholinyl, thiomorpholinylsulfoxide, thiomorpholinylsulfone, pyrrolizinyl.

The term "alkene" as used herein refers to an unsaturated hydrocarbyl group, which may be linear or branched, comprising one or more carbon-carbon double bonds. Suitable alkenyl groups comprise between 2 and 6 carbon atoms, preferably between 2 and 4 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein.

Non-limiting examples of aryl comprise phenyl, biphenylyl, biphenylenylnaphthalenyl, indenyl.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyridazinyl, pyridinyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, oxazinyl, dioxinyl, thiazinyl, triazinyl, indolyl, indolizinyl, isoindolyl, benzofuranyl, isobenzofuranyl, benzothiophenyl, isobenzothiophenyl, indazolyl, benzimidazolyl, quinolinyl, isoquinolinyl, cinnolinyl, quinazolinyl, quinoxalinyl.

The term "arylalkyl" refers to any group -alkyl-aryl. The term "alkylaryl" refers to any group -aryl-alkyl.

The term "heteroarylalkyl" refers to any group -alkyl-heteroaryl. The term "alkylheteroaryl" refers to any group -heteroaryl-alkyl.

The term "alkoxy" refers to any group O-alkyl. The term "haloalkoxy" refers to any group O-haloalkyl.

The term "oxo" refers to a =O moiety.

The term "amino" refers to a —$NH_2$ group or any group derived thereof by substitution of one nor two hydrogen atom by an organic aliphatic or aromatic group. Preferably, groups derived from —$NH_2$ are alkylamino groups, i.e. N-alkyl groups, comprising monoalkylamino and dialkylamino. According to a specific embodiment, the term "amino" refers to $NH_2$, NHMe or $NMe_2$.

The term "amino-protecting group" refers to a protecting group for an amine function. According to a preferred embodiment, the amino-protecting group is selected in the groups comprising: arylsulphonyl, tert-butoxy carbonyl, methoxymethyl, para-methoxy benzyl or benzyl.

The term "leaving group" refers to a molecular fragment that departs with a pair of electrons in heterolytic bond cleavage. According to a preferred embodiment, the leaving group is selected in the groups comprising: halogen, preferably iodine, bromine or chlorine; alkylsulfonyloxy having 1-6 carbon atoms, preferably methylsulfonyloxy or trifluoromethylsulfonyloxy; or arylsulfonyloxy having 6-10 carbon atoms, preferably phenyl- or p-tolylsulfonyloxy. The term "solvate" is used herein to describe a compound in this invention that contains stoichiometric or sub-stoichiometric amounts of one or more pharmaceutically acceptable solvent molecule such as ethanol.

The term "hydrate" refers to when the said solvent is water.

The compounds of certain embodiments of the present invention include compounds of Formula I as hereinbefore defined, including all polymorphs and crystal habits thereof, prodrugs and prodrugs thereof and isotopically-labeled compounds of Formula I.

The invention in certain embodiments also generally covers all pharmaceutically acceptable predrugs and prodrugs of the compounds of Formula I.

The term "prodrug" as used herein means the pharmacologically acceptable derivatives of compounds of Formula I, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e., neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

Certain embodiments contemplate compositions or methods by which the likelihood of occurrence of a condition or disease and/or its attendant symptoms is reduced (e.g., decreased in a statistically significant manner relative to an appropriate control), as may be determined according to criteria (e.g., clinical, diagnostic, prognostic, etc.) known to the art for a particular condition, disease and/or attendant symptoms.

The term "therapeutically effective amount" (or more simply an "effective amount") as used herein means the amount of active agent or active ingredient that is sufficient to achieve the desired therapeutic or prophylactic effect in the patient to which/whom it is administered.

The term "administration", or a variant thereof (e.g. "administering"), means providing the active agent or active ingredient, alone or as part of a pharmaceutically acceptable composition, to the patient in whom/which the condition, symptom, or disease is to be treated or prevented or for which the likelihood of occurrence is to be reduced.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The practice of certain embodiments of the present invention will employ, unless indicated specifically to the contrary, conventional methods in microbiology, molecular biology, biochemistry, molecular genetics, cell biology, virology and immunology techniques that are within the skill of the art, and reference to several of which is made below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols* (*Methods in Molecular Biology*) (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

The term "isolated" means that the material is removed from its original environment (e.g., the natural environment if it is naturally occurring). For example, a naturally occurring tissue, cell, nucleic acid or polypeptide present in its original milieu in a living animal is not isolated, but the same tissue, cell, nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

Unless the context requires otherwise, throughout the present specification and claims, the word "comprise" and variations thereof, such as, "comprises" and "comprising" are to be construed in an open, inclusive sense, that is, as "including, but not limited to". By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

EXAMPLES

The present invention will be better understood with reference to the following examples. These examples are intended to representative of specific embodiments of the invention, and are not intended as limiting the scope of the invention.

I. Chemistry Examples

The MS data provided in the examples described below were obtained as followed: Mass spectrum: LC/MS Agilent 6110 (ESI) or a Waters Acquity SQD (ESI).

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative HPLC purifications were performed with a mass directed autopurification Fractionlynx from Waters equipped with a Xbridge™ Prep C18 OBD column 19×150 mm 5 µm, unless otherwise reported. All HPLC purifications 1.1. Synthesis of Intermediate Compounds Intermediate 1:
6-fluoro-1-(phenylsulfonyl)-1H-indole The title compound was prepared using the same procedure as reported (*Bioorg. Med. Chem.* 2011, 19, 4782-4795).

Intermediate 2:
3-bromo-6-fluoro-1-(phenylsulfonyl)-1H-indole

To a solution of 6-fluoro-1-(phenylsulfonyl)-1H-indole (Intermediate 1; 1.0 g; 3.6 mmol) in DCM (20 mL) at 0° C. was added a solution of bromine (0.64 g; 4.0 mmol) in DCM (20 mL) dropwise. The mixture was stirred at 0° C. for 0.5 h, then added saturated aqueous $Na_2S_2O_3$ (10 mL), and stirred at r.t. for 10 minute. The organic layer was separated and the aqueous layer was extracted with DCM (10 mL×2). The combined organic layers were washed with saturated aqueous $NaHCO_3$ (20 mL×2), water (20 mL×2), brine (20 mL), dried over anhydrous $Na_2SO_4$, filtered, and concentrated to afford 1.26 g (99%) of the title compound as a pink solid.

$^1$H NMR (400 MHz, DMSO-$d_6$) δ [ppm]: 8.21 (s, 1H), 8.13-8.11 (m, 2H), 7.83-7.73 (m, 2H), 7.66-7.62 (m, 2H), 7.52-7.49 (m, 1H), 7.30-7.26 (m, 1H).

Intermediate 3:
6-fluoro-3-iodo-1-(phenylsulfonyl)-1H-indole

The title compound was prepared using the same procedure as reported (WO2010/136491A1).

Intermediate 4: tert-butyl 4-(6-fluoro-1-(phenylsulfonyl)-1H-indol-3-yl)-1H-pyrazole-1-carboxylate To a solution of 6-fluoro-3-iodo-1-(phenylsulfonyl)-1H-indole (Intermediate 3; 535 mg; 1.33 mmol), tert-butyl 4-(4,4,5,5-tetramethyl-1,3,2-dioxaborolan-2-yl)-1H-pyrazole-1-carboxylate (588 mg; 2.0 mmol), $K_3PO_4$ (848 mg; 4.0 mmol) in dioxane (20 mL) and water (2 mL) was added Pd(dppf)Cl$_2$ (110 mg; 0.13 mmol) under nitrogen. The mixture was stirred at 90° C. overnight. The mixture was filtered through Celite, diluted with EtOAc (100 mL) and water (100 mL). The aqueous layer was extracted with EtOAc (50 mL×2). The combined organic layers were washed with brine (100 mL), dried over anhydrous $Na_2SO_4$, concentrated, and purified by a silica gel chromatography (petroleum ether/EtOAc=10/1-2/1) to afford 357 mg (61%) of the title compound as a yellow solid.

LC-MS: m/z 442.1 [M+H]$^+$.

Intermediate 5: 6-fluoro-1-(phenylsulfonyl)-3-(1H-pyrazol-4-yl)-1H-indole

To a solution of tert-butyl 4-(6-fluoro-1-(phenylsulfonyl)-1H-indol-3-yl)-1H-pyrazole-1-carboxylate (Intermediate 4; 310 mg; 0.70 mmol) in methanol (2 mL) was added saturated HCl in Et$_2$O (10 mL). The resulting mixture was stirred for 30 minutes. The reaction was concentrated to dryness under reduced pressure, diluted with water (10 mL), neutralized with saturated aqueous $NaHCO_3$, and extracted with EtOAc (10 mL×3). The combined organic layers were washed with brine (5 mL), dried over anhydrous $Na_2SO_4$, filtered, and concentrated to afford 234 mg (89%) of the title compound as a yellow solid.

$^1$H NMR (300 MHz, DMSO-$d_6$) δ [ppm]: 13.06 (s, 1H), 8.31 (s, 1H), 8.09 (s, 1H), 8.08-8.00 (m, 3H), 7.91 (dd, J=8.7, 5.4 Hz, 1H), 7.77 (dd, J=9.6, 2.3 Hz, 1H), 7.74-7.67 (m, 1H), 7.64-7.57 (m, 2H), 7.21 (dt, J=8.7, 2.4 Hz, 1H).

Intermediate 6: 6-fluoro-3-(1-methyl-1H-pyrazol-4-yl)-1-(phenylsulfonyl)-1H-indole A mixture of 3-bromo-6-fluoro-1-(phenylsulfonyl)-1H-indole (Intermediate 2; 1.0 g; 2.8 mmol), 1-methyl-4-(4,4,5,5-tetramethyl-1,3,2-dioxaborolan-2-yl)-1H-pyrazole (1.7 g; 8.4 mmol), KOAc (1.4 g; 14.0 mmol) and Pd(dppf)Cl$_2$.CH$_2$Cl$_2$ (0.15 g; 0.18 mmol) in DMF (25 mL) flushed with nitrogen was heated to 90° C. overnight. The mixture was filtered through Celite, diluted with EtOAc (10 mL) and water (10 mL). The aqueous layer was extracted with EtOAc (20 mL×3). The combined organic layers were washed with brine, dried over anhydrous $Na_2SO_4$, filtered, concentrated, and purified by a silica gel chromatography (petroleum ether/EtOAc=1/1) to afford 0.20 g (23%) of the title compound as a yellow solid.

$^1$H NMR (400 MHz, DMSO-$d_6$) δ [ppm]: 8.22 (s, 1H), 8.09-8.05 (m, 3H), 7.96 (s, 1H), 7.90-7.87 (m, 1H), 7.79-7.76 (m, 1H), 7.72-7.69 (m, 1H), 7.63-7.59 (m, 2H), 7.25-7.20 (m, 1H), 3.89 (s, 3H).

Intermediate 7: 4-(1H-pyrazol-1-yl)pyridine

The title compound was prepared using the same procedure as reported (*Tetrahedron Lett.* 2012, 53, 948-951).

Intermediate 8:
4-(4-bromo-1H-pyrazol-1-yl)pyridine

To a solution of 4-(1H-pyrazol-1-yl)pyridine (Intermediate 7; 1.1 g; 7.5 mmol) in acetic acid (10 mL) was added a solution of bromine (6 mL) in acetic acid (10 mL) dropwise. The reaction mixture was stirred for 4 hours, diluted with saturated aqueous $Na_2S_2O_3$ (20 mL), and extracted with DCM (10 mL×3). The combined organic layers were washed with saturated aqueous $NaHCO_3$ (20 mL), water (20 mL), brine (20 mL), dried over anhydrous $Na_2SO_4$, filtered, and concentrated to afford 936 mg (55%) of the title compound as a pink solid.

$^1$H NMR (400 MHz, DMSO-$d_6$) δ [ppm]: 9.03 (s, 1H), 8.68 (d, J=6.0 Hz, 2H), 8.02 (s, 1H), 7.86 (d, J=6.1 Hz, 2H).

Intermediate 9: 4-(4-(4,4,5,5-tetramethyl-1,3,2-dioxaborolan-2-yl)-1H-pyrazol-1-yl)pyridine A mixture of 4-(4-bromo-1H-pyrazol-1-yl)pyridine (Intermediate 8; 400 mg; 1.8 mmol), 4,4,4',4',5,5,5',5'-octamethyl-2,2'-bi(1,3,2-dioxaborolane (911 mg; 3.6 mmol), Pd(dppf)Cl$_2$ (147 mg; 0.2 mmol), KOAc (878 mg; 8.9 mmol) in 1,4-dioxane (40 mL) was stirred at 80° C. overnight under argon. The combined organic solution was washed with brine (20 mL), dried over anhydrous $Na_2SO_4$, filtered, and concentrated to afford the title compound as a yellow oil, which was used directly without further purification.

LC-MS: m/z 272.1 [M+H]$^+$.

Intermediate 10: 6-fluoro-1-(phenylsulfonyl)-3-(1-(pyridin-4-yl)-1H-pyrazol-4-yl)-1H-indole A mixture of 3-bromo-6-fluoro-1-(phenylsulfonyl)-1H-indole (Intermediate 2; 317 mg; 0.9 mmol) and 4-(4-(4,4,5,5- tetramethyl-1,3,2-dioxaborolan-2-yl)-1H-pyrazol-1-yl)pyridine (Intermediate 9; 485 mg; 1.80 mmol), Pd$_2$dba$_3$ (48 mg; 0.05 mmol) and X-phos (96 mg; 0.20 mmol), and K$_3$PO$_4$ (954 mg; 4.5 mmol) in 1,4-dioxane (8 mL) and water (1 mL) was flushed with argon and reacted at 125° C. for 25 minutes in a microwave reactor. The reaction mixture was filtered through Celite, washed with EtOAc (50 mL), concentrated, and purified by a silica gel chromatography (petroleum ether/EtOAc=1/1) to afford 363 mg (96%) of the title compound as a yellow solid.

$^1$H NMR (300 MHz, DMSO-d$_6$) δ [ppm]: 9.24 (s, 1H), 8.70 (s, 2H), 8.50 (s, 1H), 8.37 (s, 1H), 8.16 (dd, J=8.5, 5.3 Hz, 1H), 8.10 (d, J=7.6 Hz, 2H), 8.00 (d, J=5.6 Hz, 2H), 7.82 (d, J=9.7 Hz, 1H), 7.73 (d, J=7.3 Hz, 1H), 7.64 (t, J=7.6 Hz, 2H), 7.30 (t, J=9.0 Hz, 1H).

Intermediate 11: 3-(4-(4,4,5,5-tetramethyl-1,3,2-dioxaborolan-2-yl)-1H-pyrazol-1-yl)pyridine The title compound was prepared using the same procedure as reported (US2011/166143 A1).

Intermediate 12: 6-fluoro-1-(phenylsulfonyl)-3-(1-(pyridin-3-yl)-1H-pyrazol-4-yl)-1H-indole Following the general method as outlined in Intermediate 10, starting from 3-(4-(4,4,5,5-tetramethyl-1,3,2-dioxaborolan-2-yl)-1H-pyrazol-1-yl)pyridine (Intermediate 11; 485 mg; 1.80 mmol), 362 mg (96%) of the title compound was obtained as a brown solid after purification by a silica gel chromatography (petroleum ether/EtOAc=1/1).

LC-MS: m/z 419.1 [M+H]$^+$.

Intermediate 13: 2-(4-bromo-1H-pyrazol-1-yl)pyridine

The title compound was prepared using the same procedure as reported (*J. Med. Chem.* 2004, 47, 4645-4648).

Intermediate 14: 2-(4-(4,4,5,5-tetramethyl-1,3,2-dioxaborolan-2-yl)-1H-pyrazol-1-yl)pyridine A mixture of 2-(4-bromo-1H-pyrazol-1-yl)pyridine (Intermediate 13; 400 mg; 1.80 mmol), 4,4,4',4',5,5,5',5'-octamethyl-2,2'-bi(1,3,2-dioxaborolane (911 mg; 3.6 mmol), Pd(dppf)Cl$_2$ (147 mg; 0.2 mmol), KOAc (878 mg; 8.9 mmol) in 1,4-dioxane (40 mL) was stirred at 80° C. overnight under argon. The mixture was filtered through Celite and washed with EtOAc (50 mL). The combined organic solution was washed with brine (20 mL), dried over anhydrous Na$_2$SO$_4$, filtered, and concentrated to afford the title compound as a yellow oil, which was used directly without further purification.

LC-MS: m/z 272.1 [M+H]$^+$.

Intermediate 15: 6-fluoro-1-(phenylsulfonyl)-3-(1-(pyridin-2-yl)-1H-pyrazol-4-yl)-1H-indole Following the general method as outlined in Intermediate 10, starting from 2-(4-(4,4,5,5-tetramethyl-1,3,2-dioxaborolan-2-yl)-1H-pyrazol-1-yl)pyridine (Intermediate 14; 485 mg; 1.80 mmol), 234 mg (62%) of the title compound was obtained as a yellow solid after purification by a silica gel chromatography (petroleum ether/EtOAc=1/1).

LC-MS: m/z 419.1 [M+H]$^+$.

Intermediate 16: tert-butyl 4-(4-(6-fluoro-1-(phenylsulfonyl)-1H-indol-3-yl)-1H-pyrazol-1-yl)-piperidine-1-carboxylate and tert-butyl 4-(4-(6-fluoro-1H-indol-3-yl)-1H-pyrazol-1-yl)piperidine-1-carboxylate To a solution of 6-fluoro-1-(phenylsulfonyl)-3-(1H-pyrazol-4-yl)-1H-indole (Intermediate 5; 939 mg; 2.75 mmol) and Cs$_2$CO$_3$ (2.23 g; 6.84 mmol) in DMF (20 mL) was added tert-butyl 4-(methylsulfonyloxy)piperidine-1-carboxylate (1.00 g; 3.58 mmol) under nitrogen. The reaction mixture was stirred at 85° C. overnight, concentrated, and purified by a silica gel chromatography (petroleum ether/EtOAc=2/1) to afford 880 mg (61%) and 230 mg (22%) of the 15A and 15B as a yellow solid.

For 16A: LC-MS: m/z 469.1 [M+H-tBu]$^+$.

$^1$H NMR (400 MHz, DMSO-d$_6$) δ [ppm]: 8.39 (s, 1H), 8.09 (s, 1H), 8.04 (d, J=7.5 Hz, 2H), 7.99 (s, 1H), 7.94 (dd, J=8.8, 5.4 Hz, 1H), 7.76 (dd, J=9.8, 2.2 Hz, 1H), 7.70 (t, J=7.5 Hz, 1H), 7.60 (t, J=7.8 Hz, 2H), 7.21 (td, J=9.1, 2.3 Hz, 1H), 4.38 (dd, J=9.6, 5.7 Hz, 1H), 4.12-3.98 (m, 3H), 3.07-2.81 (m, 3H), 2.08-2.00 (m, 2H), 1.86 (td, J=12.1, 4.1 Hz, 2H), 1.43 (s, 9H).

For 16B: LC-MS: m/z 385.2 [M+H]$^+$.

$^1$H NMR (400 MHz, DMSO-d$_6$) δ [ppm]: 11.16 (s, 1H), 8.16 (s, 1H), 7.88-7.72 (m, 2H), 7.53 (d, J=2.3 Hz, 1H), 7.16 (dd, J=10.1, 2.3 Hz, 1H), 6.90 (td, J=9.7, 2.3 Hz, 1H), 4.45-4.29 (m, 1H), 4.13-3.96 (m, 2H), 3.07-2.87 (m, 3H), 2.08-1.98 (m, 2H), 1.91-1.75 (m, 2H), 1.40 (s, 9H).

Intermediate 17: 6-fluoro-1-(phenylsulfonyl)-3-(1-(piperidin-4-yl)-1H-pyrazol-4-yl)-1H-indole hydrochloride To a solution of tert-butyl 4-(4-(6-fluoro-1-(phenylsulfonyl)-1H-indol-3-yl)-1H-pyrazol-1-yl)piperidine-1-carboxylate (Intermediate 16A; 580 mg; 1.11 mmol) in dioxane (3 mL) was added conc. aqueous HCl (3 mL; 36%). The reaction mixture was stirred for 0.5 hour and concentrated afford 580 mg (>100%) of the title compound as a white solid.

LC-MS: m/z 425.1 [M+H]$^+$.

$^1$H NMR (400 MHz, DMSO-d$_6$) δ [ppm]: 8.37 (s, 1H), 8.13 (s, 1H), 8.05 (t, J=3.7 Hz, 3H), 7.92 (dd, J=8.8, 5.3 Hz, 1H), 7.77 (dd, J=9.8, 2.2 Hz, 1H), 7.71 (t, J=7.4 Hz, 1H), 7.61 (dd, J=9.7, 5.8 Hz, 2H), 7.23 (td, J=9.1, 2.2 Hz, 1H), 4.55-4.51 (m, 1H), 3.38-3.41 (m, 2H), 3.14-3.02 (m, 2H), 2.31-2.12 (m, 4H).

Intermediate 18: tert-butyl 2-(4-(6-fluoro-1-(phenylsulfonyl)-1H-indol-3-yl)-1H-pyrazol-1-yl)ethylcarbamate To a solution of 6-fluoro-1-(phenylsulfonyl)-3-(1H-pyrazol-4-yl)-1H-indole (Intermediate 5; 500 mg; 1.46 mmol) in DMF (30 mL) was added tert-butyl 2-bromoethylcarbamate (658 mg; 2.94 mmol) and Cs$_2$CO$_3$ (1.43 g; 4.39 mmol) and catalytic amount of tetrabutylammonium iodide (107 mg; 0.29 mmol) under nitrogen. The reaction mixture was stirred at 85° C. for 24 hours. Most of DMF was removed and the residue was diluted with EtOAc (100 mL), washed with water (50 ml×3), brine (50 mL), dried over anhydrous Na$_2$SO$_4$, filtered, concentrated, and purified by reversed phase flash chromatography to afford 500 mg (70%) of the title compound as a yellow solid.

LC-MS: m/z 485.2 [M+H]$^+$.

$^1$H NMR (400 MHz, DMSO-d$_6$) δ [ppm]: 8.26 (s, 1H), 8.11-8.01 (m, 3H), 7.99 (s, 1H), 7.93-7.85 (m, 1H), 7.77 (dd, J=10.1, 1.7 Hz, 1H), 7.69 (d, J=6.6 Hz, 1H), 7.60 (t, J=7.5 Hz, 2H), 7.22 (td, J=9.2, 2.5 Hz, 1H), 6.95 (s, 1H), 4.44 (t, J=4.9 Hz, 2H), 4.17 (t, J=6.5 Hz, 2H), 1.32 (s, 9H).

Intermediate 19: 2-(4-(6-fluoro-1-(phenylsulfonyl)-1H-indol-3-yl)-1H-pyrazol-1-yl)ethanamine hydrochloride To a solution of tert-butyl 2-(4-(6-fluoro-1-(phenylsulfonyl)-1H-indol-3-yl)-1H-pyrazol-1-yl)ethylcarbamate (260 mg; 0.54 mmol) in dioxane (5 mL) was added conc. aqueous HCl (5 mL; 36%). The reaction mixture was stirred for 1 hours and concentrated to afford 260 mg (68%) of the title compound as a yellow solid, which was used directly without further purification.
LC-MS: m/z 385.2 [M+H]$^+$.

Intermediate 20: tert-butyl 4-((4-(6-fluoro-1-(phenylsulfonyl)-1H-indol-3-yl)-1H-pyrazol-1-yl)methyl)piperidine-1-carboxylate To a solution of 6-fluoro-1-(phenylsulfonyl)-3-(1H-pyrazol-4-yl)-1H-indole (Intermediate 5; 1.20 g; 3.52 mmol) and Cs$_2$CO$_3$ (2.26 g; 6.94 mmol) in DMF (20 mL) was added tert-butyl 4-((methylsulfonyloxy)methyl)piperidine-1-carboxylate (1.32 g; 4.50 mmol) under nitrogen. The reaction mixture was stirred at 90° C. for 2 hours, cooled to r.t., added to water (200 mL) with vigorous stirring. The resulting solid was collected by vacuum filtration to afford 1.60 g (84%) of the title compound as a yellow solid.
$^1$H NMR (300 MHz, DMSO-d$_6$) δ [ppm]: 8.31 (s, 1H), 8.10 (s, 1H), 8.05 (d, J=7.4 Hz, 2H), 7.99 (s, 1H), 7.88 (dd, J=8.8, 5.3 Hz, 1H), 7.73 (dd, J=22.0, 7.7 Hz, 2H), 7.61 (t, J=7.5 Hz, 2H), 7.23 (s, 1H), 4.03 (dd, J=7.0, 3.6 Hz, 2H), 3.94 (s, 2H), 2.67 (s, 2H), 2.07 (s, 1H), 1.49 (d, J=12.7 Hz, 2H), 1.08 (d, J=12.0 Hz, 2H).

Intermediate 21: 6-fluoro-1-(phenylsulfonyl)-3-(1-(piperidin-4-ylmethyl)-1H-pyrazol-4-yl)-1H-indole To a solution of tert-butyl 4-((4-(6-fluoro-1-(phenylsulfonyl)-1H-indol-3-yl)-1H-pyrazol-1-yl)methyl)piperidine-1-carboxylate (Intermediate 20; 1.60 g; 2.97 mmol) in THF (10 mL) was added conc. aqueous HCl (5 mL; 36%). The reaction mixture was stirred for 1 hour and concentrated, neutralized with saturated aqueous Na$_2$CO$_3$ (500 mL), extracted with EtOAc (200 ml×2). The combined organic layers were dried over anhydrous Na$_2$SO$_4$, filtered, concentrated, and purified by reversed phase flash chromatography to afford 1.08 g (83%) of the title compound as a red oil.
$^1$H NMR (300 MHz, DMSO-d$_6$) δ [ppm]: 8.31 (s, 1H), 8.09 (s, 1H), 8.05 (d, J=7.6 Hz, 2H), 7.97 (s, 1H), 7.88 (s, 1H), 7.77 (d, J=10.0 Hz, 1H), 7.71 (s, 1H), 7.62 (d, J=7.5 Hz, 2H), 7.23 (s, 1H), 3.99 (d, J=7.1 Hz, 2H), 2.88 (s, 2H), 2.39 (s, 2H), 1.93 (s, 2H), 1.42 (d, J=14.5 Hz, 2H), 1.07 (d, J=7.0 Hz, 2H).

Intermediate 22: 3-(1-(2-bromoethyl)-1H-pyrazol-4-yl)-6-fluoro-1-(phenylsulfonyl)-1H-indole To a solution of 6-fluoro-1-(phenylsulfonyl)-3-(1H-pyrazol-4-yl)-1H-indole (Intermediate 5; 1.0 g; 2.93 mmol) in DMF (50 mL) was added NaH (176 mg; 4.4 mmol; 60%) at 0° C. under nitrogen. The reaction mixture was stirred at 0° C. for 1 hour, added 1,2-dibromoethane (0.83 g; 4.4 mmol), warmed to r.t. and stirred overnight. The mixture was poured into ice-water (50 mL) and extracted by EtOAc (50 mL×3). The combined organic layers was washed with brine (100 mL), dried over anhydrous Na$_2$SO$_4$, concentrated, and purified by a silica gel chromatography (petroleum ether/EtOAc=2/1) to afford 0.48 g (37%) of the title compound as a yellow solid.
$^1$H NMR (300 MHz, DMSO-d$_6$) δ [ppm]: 8.41 (s, 1H), 8.12 (s, 1H), 8.07-8.05 (m, 3H), 7.95-7.86 (m, 1H), 7.79-7.75 (m, 1H), 7.73-7.68 (m, 1H), 7.63-7.58 (m, 2H), 7.27-7.20 (m, 1H), 4.57-4.37 (t, 2H), 3.93-3.89 (t, 2H).

Intermediate 23: tert-butyl 3-(4-(6-fluoro-1-(phenylsulfonyl)-1H-indol-3-yl)-1H-pyrazol-1-yl)azetidine-1-carboxylate Following the general method as outlined in Intermediate 16, starting from 6-fluoro-1-(phenylsulfonyl)-3-(1H-pyrazol-4-yl)-1H-indole (Intermediate 5; 812 mg; 2.38 mmol) and tert-butyl 3-iodoazetidine-1-carboxylate (674 mg; 2.38 mmol), 1.19 g (100%) of the title compound was obtained as a yellow solid, which was used directly without further purification.
LC-MS: m/z 397 [M+H-Boc]$^+$.

Intermediate 24: 3-(1-(azetidin-3-yl)-1H-pyrazol-4-yl)-6-fluoro-1-(phenylsulfonyl)-1H-indole hydrochloride Following the general method as outlined in Intermediate 17, starting from tert-butyl 3-(4-(6-fluoro-1-(phenylsulfonyl)-1H-indol-3-yl)-1H-pyrazol-1-yl)azetidine-1-carboxylate (Intermediate 23; 1.32 g; 2.66 mmol), 1.30 g of the title compound was obtained as a brown solid, which was used directly without further purification.
LC-MS: m/z 397 [M+H]$^+$.

Intermediate 25: 1,5-dimethyl-4-(4,4,5,5-tetramethyl-1,3,2-dioxaborolan-2-yl)-1H-pyrazole and 1,3-dimethyl-4-(4,4,5,5-tetramethyl-1,3,2-dioxaborolan-2-yl)-1H-pyrazole A solution of 3-methyl-4-(4,4,5,5-tetramethyl-1,3,2-dioxaborolan-2-yl)-1H-pyrazole (0.60 g; 2.9 mmol) and K$_2$CO$_3$ (2.0 g; 14 mmol) in MeCN (20 mL) was stirred overnight under nitrogen and added iodomethane (1.0 mL; 16 mmol). The reaction mixture was stirred overnight, diluted with EtOAc (20 mL), filtered, and concentrated to afford 727 mg of an inseparable mixture of the title compounds as a light yellow solid.
LC-MS: m/z 223.1 [M+H]$^+$.

Intermediate 26: 3-(1,5-dimethyl-1H-pyrazol-4-yl)-6-fluoro-1-(phenylsulfonyl)-1H-indole and 3-(1,3-dimethyl-1H-pyrazol-4-yl)-6-fluoro-1-(phenylsulfonyl)-1H-indole Following the general method as outlined in Intermediate 4, starting from 1,5-dimethyl-4-(4,4,5,5-tetramethyl-1,3,2-dioxaborolan-2-yl)-1H-pyrazole and 1,3-dimethyl-4-(4,4,5,5-tetramethyl-1,3,2-dioxaborolan-2-yl)-1H-pyrazole (Intermediate 25; 670 mg; 3.02 mmol) and 6-fluoro-3-iodo-1-(phenylsulfonyl)-1H-indole (Intermediate 3; 807 mg; 2.01 mmol), 382 mg (51%) of an inseparable mixture of the title compounds as a light yellow solid.
LC-MS: m/z 370.1 [M+H]$^+$.

Intermediate 27: 5,6-difluoro-3-iodo-1H-indole

To a mixture of 5,6-difluoro-1H-indole (500 mg; 3.27 mmol) and KOH (458 mg; 8.18 mmol) in DMF (6.2 mL) was added a solution of iodine (837.5 mg; 3.3 mmol) in DMF (6.3 mL). The mixture was stirred at r.t. for 12 hours. It was poured into an ice-water mixture (60 mL) and extracted with EtOAc (20 mL×3). The combined organic layers was washed with brine (100 mL) and dried over anhydrous $Na_2SO_4$, filtered, concentrated to afford 930 mg (100%) of the title compound as a red solid. It was used to next step without further purification.

$^1$H NMR (400 MHz, DMSO-$d_6$) δ [ppm]: 11.68 (s, 1H), 7.61 (d, J=2.5 Hz, 1H), 7.47 (dd, J=11.0, 6.9 Hz, 1H), 7.21 (dd, J=10.8, 7.9 Hz, 1H).

Intermediate 28: 5,6-difluoro-3-iodo-1-(phenylsulfonyl)-1H-indole

To a solution of 5,6-difluoro-3-iodo-1H-indole (Intermediate 27; 930 mg; 3.33 mmol) in THF (20 mL) at 0° C. was added NaH (266.4 mg; 60%; 6.66 mmol) under nitrogen. The reaction mixture was stirred at r.t. for 15 minutes before a solution of benzenesulfonyl chloride (763.4 mg; 4.32 mmol) in THF (2 mL) was added dropwise. The reaction was stirred at r.t. for 12 hours, quenched with an ice-water mixture (60 mL) and extracted with EtOAc (30 mL×3). The combined organic layers were washed with brine (100 mL), dried over anhydrous $Na_2SO_4$, filtered, concentrated, and purified by a silica gel chromatography (petroleum ether/EtOAc=10/1-3/1) to afford 1.01 g (72%) of the title compound as a yellow solid.

$^1$H NMR (400 MHz, DMSO-$d_6$) δ [ppm]: 8.19 (s, 1H), 8.12 (d, J=7.9 Hz, 2H), 8.07-8.00 (m, 1H), 7.78-7.72 (m, 1H), 7.64 (t, J=8.0 Hz, 2H), 7.41 (dd, J=10.2, 7.8 Hz, 1H).

Intermediate 29: tert-butyl 4-(5,6-difluoro-1-(phenylsulfonyl)-1H-indol-3-yl)-1H-pyrazole-1-carboxylate To a solution of 5,6-difluoro-3-iodo-1-(phenylsulfonyl)-1H-indole (Intermediate 28; 300 mg; 0.716 mmol), tert-butyl 4-(4,4,5,5-tetramethyl-1,3,2-dioxaborolan-2-yl)-1H-pyrazole-1-carboxylate (273.6 mg; 0.93 mmol), $K_3PO_4$ (455 mg; 2.15 mmol) in dioxane (10 mL) and water (1 mL) was added Pd(dppf)Cl$_2$ (59 mg; 0.072 mmol) under argon. The reaction mixture was stirred at 90° C. for 12 hours. The mixture was filtered through Celite and washed with EtOAc (50 mL). The combined organic layers were washed with brine (100 mL), dried over anhydrous $Na_2SO_4$, concentrated, and purified by a silica gel chromatography (petroleum ether/EtOAc=1/1) to afford 203 mg (62%) of the title compound as a yellow solid.

$^1$H NMR (400 MHz, DMSO-$d_6$) δ [ppm]: 8.83 (s, 1H), 8.45 (s, 1H), 8.41 (d, J=0.6 Hz, 1H), 8.10 (dd, J=5.3, 3.4 Hz, 2H), 8.07-7.99 (m, 2H), 7.72 (d, J=7.4 Hz, 1H), 7.63 (t, J=7.8 Hz, 2H), 1.62 (s, 9H).

Intermediate 30: 5,6-difluoro-1-(phenylsulfonyl)-3-(1H-pyrazol-4-yl)-1H-indole hydrochloride To a solution of tert-butyl 4-(5,6-difluoro-1-(phenylsulfonyl)-1H-indol-3-yl)-1H-pyrazole-1-carboxylate (Intermediate 29; 203 mg; 0.44 mmol) in EtOAc (2 mL) was added HCl in EtOAc (4 M; 1 mL). The resulting mixture was stirred for 2 hours. The reaction mixture was concentrated to dryness under reduced pressure to afford 150 mg (88%) of the title compound as a red solid.

LC-MS: m/z 360.1 [M+H]$^+$.

$^1$H NMR (400 MHz, DMSO-$d_6$) δ [ppm]: 13.08 (s, 1H), 8.36 (s, 1H), 8.18 (s, 1H), 8.10-8.05 (m, 2H), 7.99 (m, 3H), 7.71 (dd, J=8.4, 6.5 Hz, 1H), 7.61 (t, J=7.7 Hz, 2H).

Intermediate 31: 2-(2-oxoimidazolidin-1-yl)ethyl methanesulfonate

To a solution of 1-(2-hydroxyethyl)imidazolidin-2-one (100 mg; 0.77 mmol) and Et$_3$N (81 mg; 0.80 mmol) in dry DCM (10 mL) was added MsCl (137 mg; 1.20 mmol) under nitrogen. The reaction mixture was stirred overnight, diluted with DCM (20 mL), washed with saturated aqueous $Na_2CO_3$, dried over anhydrous $Na_2SO_4$, concentrated to afford 72 mg (44%) of the title compound as a yellow oil, which was used directly without further purification.

Intermediate 32: benzyl 3-hydroxycyclobutanecarboxylate

NaBH$_4$ (215 mg; 5.68 mmol) was added to the solution of benzyl 3-oxocyclobutanecarboxylate (2.3 g; 11.3 mmol) in THF (30 mL) and MeOH (1.5 mL). The reaction mixture was stirred for 0.5 hour at 0° C., diluted with water (20 mL), and extracted with DCM (50 mL×2). The combined organic layers were dried over anhydrous $Na_2SO_4$, filtered, concentrated, and purified by reverse phase flash chromatography to afford 1.24 g (53%) of the title compound as a yellow oil.

$^1$H NMR (400 MHz, CDCl$_3$) δ [ppm]: 7.49-7.22 (m, 5H), 5.12 (d, J=4.1 Hz, 2H), 4.28-4.08 (m, 1H), 2.72-2.50 (m, 3H), 2.41-2.09 (m, 3H).

Intermediate 33: benzyl 3-((methylsulfonyl)oxy)cyclobutanecarboxylate

To a solution of benzyl 3-hydroxycyclobutanecarboxylate (Intermediate 32; 0.90 g; 4.4 mmol), Et$_3$N (1.20 mL; 8.6 mmol) in DCM (50 mL) was added MsCl (0.40 mL; 5.2 mmol) under nitrogen. The reaction mixture was stirred for 1 hour, quenched with water (20 mL), and extracted with DCM (50 mL×2). The combined organic layers were dried over anhydrous $Na_2SO_4$, filtered, and concentrated to afford 1.24 g (100%) of the title compound as a yellow oil, which was used directly without further purification.

$^1$H NMR (300 MHz, DMSO-$d_6$) δ [ppm]: 7.45-7.28 (m, 5H), 5.16-5.07 (m, 2H), 4.93 (t, J=7.4 Hz, 1H), 3.16 (s, 3H), 2.86 (dd, J=16.7, 8.5 Hz, 1H), 2.67 (dtd, J=10.2, 7.5, 2.8 Hz, 2H), 2.44-2.28 (m, 2H).

Intermediate 34A and B: trans- and cis-benzyl 3-(4-(6-fluoro-1-(phenylsulfonyl)-1H-indol-3-yl)-1H-pyrazol-1-yl)cyclobutanecarboxylate A mixture of benzyl 3-((methylsulfonyl)oxy)cyclobutanecarboxylate (Intermediate 33; 1.24 g; 4.36 mmol), 6-fluoro-1-(phenylsulfonyl)-3-(1H-pyrazol-4-yl)-1H-indole (Intermediate 5; 1.35 g; 3.95 mmol), and Cs$_2$CO$_3$ (2.59 g; 7.95 mmol) in DMF (20 mL) was stirred at 90° C. overnight under nitrogen, cooled to r.t., diluted with water (50 mL), and extracted with EtOAc (100 ml×2). The combined organic layers were dried over anhydrous $Na_2SO_4$, filtered, concentrated, and purified by a silica gel chromatography (petroleum ether/EtOAc=4/1) to afford 600 mg (29%) of Intermediate 34A and 500 mg (24%) of Intermediate 34B as colorless oils.

LC-MS: m/z 530 [M+H]$^+$.

Intermediate 35: trans-3-(4-(6-fluoro-1-(phenylsulfonyl)-1H-indol-3-yl)-1H-pyrazol-1-yl)cyclobutanecarboxylic acid A mixture of trans-benzyl 3-(4-(6-fluoro-1-(phenylsulfonyl)-1H-indol-3-yl)-1H-pyrazol-1-yl)cyclobutanecarboxylate (Intermediate 34A; 500 mg; 0.944 mmol) and Pd/C (50 mg) in MeOH (50 mL) was stirred overnight under a hydrogen balloon. The reaction mixture was filtered and the filtrate was concentrated and purified by reverse phase flash chromatography to afford 113 mg (27%) of the title compound as a yellow oil.
LC-MS: m/z 440 [M+H]$^+$.

Intermediate 36: cis-3-(4-(6-fluoro-1-(phenylsulfonyl)-1H-indol-3-yl)-1H-pyrazol-1-yl)cyclobutanecarboxylic acid Following the general method as outlined in Intermediate 35, starting from cis-benzyl 3-(4-(6-fluoro-1-(phenylsulfonyl)-1H-indol-3-yl)-1H-pyrazol-1-yl)cyclobutanecarboxylate (Intermediate 34B; 600 mg; 1.13 mmol), 440 mg (88%) of the title compound was obtained as a yellow oil, which was used directly without further purification.
LC-MS: m/z 440 [M+H]$^+$.

Intermediate 37: tert-butyl 3-((4-(6-fluoro-1-(phenylsulfonyl)-1H-indol-3-yl)-1H-pyrazol-1-yl)methyl)azetidine-1-carboxylate Following the general method as outlined in Intermediate 20, starting from 6-fluoro-1-(phenylsulfonyl)-3-(1H-pyrazol-4-yl)-1H-indole (Intermediate 5; 1.22 g; 3.56 mmol) and tert-butyl 3-(((methylsulfonyl)oxy)methyl)azetidine-1-carboxylate (1.40 g; 5.28 mmol), 1.37 g (76%) of the title compound as a yellow solid.
LC-MS: m/z 455.0 [M+H$^+$-tBu]$^+$.
$^1$H NMR (400 MHz, DMSO-d$_6$) δ [ppm]: 8.39 (s, 1H), 8.00-8.10 (m, 4H), 7.94-7.84 (m, 1H), 7.77 (d, J=9.3 Hz, 1H), 7.70 (dd, J=12.9, 6.3 Hz, 1H), 7.61 (t, J=7.6 Hz, 3H), 7.23 (dd, J=13.7, 4.9 Hz, 1H), 4.36 (d, J=7.1 Hz, 2H), 3.98-3.83 (m, 2H), 3.69-3.71 (m, 3H), 2.99-3.01 (m, 2H), 1.33 (s, 9H).

Intermediate 38: 3-(1-(azetidin-3-ylmethyl)-1H-pyrazol-4-yl)-6-fluoro-1-(phenylsulfonyl)-1H-indole To a solution of tert-butyl 3-((4-(6-fluoro-1-(phenylsulfonyl)-1H-indol-3-yl)-1H-pyrazol-1-yl)methyl)azetidine-1-carboxylate (Intermediate 37; 330 mg; 0.65 mmol) in DCM (10 mL) was added TFA (5 mL) dropwise. The reaction mixture was stirred for 0.5 hour and concentrated, neutralized with saturated aqueous Na$_2$CO$_3$ (50 mL), extracted with EtOAc (50 ml×2). The combined organic layers were dried over anhydrous Na$_2$SO$_4$, filtered, concentrated and purified by preparative TLC to afford 265 mg (100%) of the title compound as a brown solid.
LC-MS: m/z 411.0 [M+H]$^+$.

Intermediate 39:
3-iodo-6-(trifluoromethyl)-1H-indole

Following the general method as outlined in Intermediate 3, starting from 6-(trifluoromethyl)-1H-indole (0.97 g; 5.24 mmol), 1.60 g (98%) of the title compound was obtained as a red solid, which was used directly without further purification.
$^1$H NMR (400 MHz, DMSO-d$_6$) δ [ppm]: 11.95 (s, 1H), 7.79 (d, J=16.1 Hz, 2H), 7.49 (d, J=8.3 Hz, 1H), 7.40 (d, J=8.4 Hz, 1H).

Intermediate 40: 3-iodo-1-(phenylsulfonyl)-6-(trifluoromethyl)-1H-indole

Following the general method as outlined in Intermediate 28, starting from 3-iodo-6-(trifluoromethyl)-1H-indole (Intermediate 39; 1.60 g; 5.14 mmol), 1.06 g (45%) of the title compound was obtained as a yellow solid.
$^1$H NMR (400 MHz, DMSO-d$_6$) δ [ppm]: 8.39 (s, 1H), 8.20 (s, 1H), 8.09 (d, J=7.6 Hz, 2H), 7.78-7.68 (m, 2H), 7.66 (d, J=7.9 Hz, 2H), 7.64-7.58 (m, 1H).

Intermediate 41: tert-butyl 4-(1-(phenylsulfonyl)-6-(trifluoromethyl)-1H-indol-3-yl)-1H-pyrazole-1-carboxylate Following the general method as outlined in Intermediate 4, starting from 3-iodo-1-(phenylsulfonyl)-6-(trifluoromethyl)-1H-indole (Intermediate 40; 300 mg; 0.66 mmol) 0.40 g (94%) of the title compound was obtained as a black oil, which was used directly without further purification.
LC-MS: m/z 392.1 [M+H$^+$-Boc]$^+$.

Intermediate 42: 1-(phenylsulfonyl)-3-(1H-pyrazol-4-yl)-6-(trifluoromethyl)-1H-indole Following the general method as outlined in Intermediate 5, starting from tert-butyl 4-(1-(phenylsulfonyl)-6-(trifluoromethyl)-1H-indol-3-yl)-1H-pyrazole-1-carboxylate (Intermediate 41; 400 mg; 0.81 mmol), 300 mg (95%) of the title compound was obtained as a yellow oil, which was used directly without further purification.
LC-MS: m/z 392.1 [M+H$^+$]$^+$.

Intermediate 43: 2-(2-oxopyrrolidin-1-yl)ethyl methanesulfonate

Following the general method as outlined in Intermediate 31, starting from 1-(2-hydroxyethyl)pyrrolidin-2-one (500 mg; 3.87 mmol), 400 mg (50%) of the title compound as a yellow oil, which was used directly without further purification.

Intermediate 44: 3-(1-(6-chloropyridazin-3-yl)-1H-pyrazol-4-yl)-6-fluoro-1-(phenylsulfonyl)-1H-indole A mixture of 6-fluoro-1-(phenylsulfonyl)-3-(1H-pyrazol-4-yl)-1H-indole (Intermediate 5; 512 mg; 1.50 mmol), 3,6-dichloropyridazine (450 mg; 3.02 mmol) and K$_2$CO$_3$ (828 mg; 5.99 mmol) in MeCN (15.0 mL) was stirred at 100° C. for 16 hours under nitrogen. The reaction mixture was diluted with EtOAc (30 mL) and water (10 mL). The organic layer was separated, washed with brine (10 mL), dried over anhydrous Na$_2$SO$_4$, filtered, concentrated, and purified by a silica gel column chromatography (petroleum ether/EtOAc=4/1 to 2/1) to afford 620 mg (91%) of the title compound as a white solid.
LC-MS: m/z 454 [M+H]$^+$.
$^1$H NMR (400 MHz, DMSO-d$_6$) δ [ppm]: 9.33 (s, 1H), 8.59 (s, 1H), 8.43 (s, 1H), 8.33 (d, J=9.0 Hz, 1H), 8.14-8.03 (m, 4H), 7.80 (dd, J=9.6, 2.4 Hz, 1H), 7.74-7.69 (m, 1H), 7.67-7.59 (m, 2H), 7.26 (dt, J=9.0, 2.4 Hz, 1H).

Intermediate 45: tert-butyl 4-((4-(5,6-difluoro-1-(phenylsulfonyl)-1H-indol-3-yl)-1H-pyrazol-1-yl)methyl)piperidine-1-carboxylate Following the general method as outlined in Intermediate 20, starting from 5,6-difluoro-1-(phenylsulfonyl)-3-(1H-pyrazol-4-yl)-1H-indole hydrochloride (Intermediate 30; 300 mg; 0.76 mmol), 330 mg (78%) of the title compound was obtained as a yellow solid after purification by a silica gel chromatography(petroleum ether/EtOAc=5/1).
LC-MS: m/z 501.1 [M+H$^+$-tBu]$^+$.

Intermediate 46: 5,6-difluoro-1-(phenylsulfonyl)-3-(1-(piperidin-4-ylmethyl)-1H-pyrazol-4-yl)-1H-indole Following the general method as outlined in Intermediate 21, starting from tert-butyl 4-((4-(5,6-difluoro-1-(phenylsulfonyl)-1H-indol-3-yl)-1H-pyrazol-1-yl)methyl)piperidine-1-carboxylate (Intermediate 45; 330 mg; 0.59 mmol), 830 mg (>100%) of the title compound was obtained as a yellow solid, which was used directly without further purification.

LC-MS: m/z 457.1 [M+H$^+$]$^+$.

Intermediate 47: 3-(1-(1,4-dioxaspiro[4.5]decan-8-yl)-1H-pyrazol-4-yl)-6-fluoro-1-(phenylsulfonyl)-1H-indole Following the general method as outlined in Intermediate 16, starting from 6-fluoro-1-(phenylsulfonyl)-3-(1H-pyrazol-4-yl)-1H-indole (Intermediate 5; 600 mg; 1.76 mmol) and 1,4-dioxaspiro[4.5]decan-8-ylmethanesulfonate (498 mg; 2.11 mmol), 500 mg (59%) of the title compound was obtained as a white solid after purification by reverse phase flash chromatography.

LC-MS: m/z 482 [M+H]$^+$.

Intermediate 48: 4-(4-(6-fluoro-1-(phenylsulfonyl)-1H-indol-3-yl)-1H-pyrazol-1-yl)cyclohexanone To a solution of 3-(1-(1,4-dioxaspiro[4.5]decan-8-yl)-1H-pyrazol-4-yl)-6-fluoro-1-(phenylsulfonyl)-1H-indole (Intermediate 47; 500 mg; 1.04 mmol) in THF (20 mL) was added HCl (0.35 mL; 35%). The reaction mixture was stirred overnight, concentrated, and purified by reverse phase flash chromatography to afford 197 mg (43%) of the title compound as a white solid.

LC-MS: m/z 438 [M+H]$^+$.

Intermediate 49: trans-4-(4-(6-fluoro-1-(phenylsulfonyl)-1H-indol-3-yl)-1H-pyrazol-1-yl)cyclohexanol To a solution of 4-(4-(6-fluoro-1-(phenylsulfonyl)-1H-indol-3-yl)-1H-pyrazol-1-yl)cyclohexanone (Intermediate 48; 197 mg; 0.45 mmol) in MeOH (15 mL) was added NaBH$_4$ (34 mg; 0.90 mmol). The reaction mixture was stirred overnight, concentrated, and purified by preparative TLC (DCM/MeOH=20/1) to afford 32 mg (16%) of the title compound as a white solid.

$^1$H NMR (400 MHz, MeOH-d$_4$) δ [ppm]: 8.10 (s, 1H), 7.99 (dd, J=8.5, 1.1 Hz, 2H), 7.86 (d, J=11.3 Hz, 2H), 7.82-7.74 (m, 2H), 7.69-7.62 (m, 1H), 7.56 (t, J=7.7 Hz, 2H), 7.17-7.09 (m, 1H), 4.25 (dd, J=9.9, 5.8 Hz, 1H), 3.79-3.62 (m, 1H), 2.25-2.09 (m, 4H), 2.04-1.90 (m, 2H), 1.53 (dd, J=16.9, 6.0 Hz, 2H).

1.2. Synthesis of Final Compounds

Example 2

3-(1-(azetidin-3-yl)-1H-pyrazol-4-yl)-6-fluoro-1H-indole

Step 1: tert-butyl 3-(4-(6-fluoro-1H-indol-3-yl)-1H-pyrazol-1-yl)azetidine-1-carboxylate A mixture of 6-fluoro-1-(phenylsulfonyl)-3-(1H-pyrazol-4-yl)-1H-indole (Intermediate 5; 346 mg; 1.0 mmol), tert-butyl 3-iodoazetidine-1-carboxylate (283 mg; 1.0 mmol) and NaH (100 mg; 2.5 mmol; 60% w/w) in DMF (5 mL) was heated to 120° C. for 0.5 hour in a microwave reactor. The reaction mixture was added NaOH (100 mg; 2.50 mmol) in water (0.5 mL) and stirred for 0.5 hour at 85° C. The mixture was concentrated and purified by a silica gel chromatography (petroleum ether/EtOAc=1/1) to afford 220 mg (62%) of the title compound as a yellow solid.

LC-MS: m/z 357 [M+H]$^+$.

Step 2

To a solution of tert-butyl 3-(4-(6-fluoro-1H-indol-3-yl)-1H-pyrazol-1-yl)azetidine-1-carboxylate (Step 1; 220 mg; 0.62 mmol) in MeOH (10 mL) was added saturated HCl in Et$_2$O (5 mL). The mixture was stirred for 3 h, concentrated, and purified by preparative HPLC to afford 27.8 mg (18%) of the title compound as a white solid.

$^1$H NMR (400 MHz, DMSO-d$_6$) δ [ppm]: 11.20 (s, 1H), 8.23 (s, 1H), 7.86 (d, J=4.0 Hz, 1H), 7.78 (dd, J=8.7, 5.4 Hz, 1H), 7.56 (d, J=2.1 Hz, 1H), 7.17 (dd, J=10.1, 2.1 Hz, 1H), 7.01-6.80 (m, 1H), 5.31-5.11 (m, 1H), 3.97 (t, J=7.6 Hz, 2H), 3.73 (t, J=7.9 Hz, 2H), 2.96 (s, 1H). m.p. 205.6-206.7° C.

Example 3

1-(3-(4-(6-fluoro-1H-indol-3-yl)-1H-pyrazol-1-yl)azetidin-1-yl)ethanone

Step 1: 1-(3-(4-(6-fluoro-1-(phenylsulfonyl)-1H-indol-3-yl)-1H-pyrazol-1-yl)azetidin-1-yl)ethanone Following the general method as outlined in Example 89, starting from 3-(1-(azetidin-3-yl)-1H-pyrazol-4-yl)-6-fluoro-1-(phenylsulfonyl)-1H-indole hydrochloride (Intermediate 24; 350 mg; 0.81 mmol), 355 mg (100%) of the title compound was obtained as a brown solid, which was used directly without further purification.

LC-MS: m/z 439 [M+H]$^+$.

Step 2

Following the general method as outlined in Example 70, starting from 1-(3-(4-(6-fluoro-1-(phenylsulfonyl)-1H-indol-3-yl)-1H-pyrazol-1-yl)azetidin-1-yl)ethanone (Step 1; 355 mg; 0.81 mmol), 146 mg (61%) of the title compound was obtained as a yellow solid after purification by preparative HPLC.

$^1$H NMR (400 MHz, DMSO-d$_6$) δ [ppm]: 11.22 (s, 1H), 8.31 (s, 1H), 7.93 (s, 1H), 7.80 (dd, J=8.7, 5.5 Hz, 1H), 7.59 (d, J=2.4 Hz, 1H), 7.17 (dd, J=10.0, 2.3 Hz, 1H), 6.99-6.86 (m, 1H), 5.27 (d, J=5.4 Hz, 1H), 4.59 (t, J=8.4 Hz, 1H), 4.46 (dd, J=8.8, 5.5 Hz, 1H), 4.32 (t, J=9.0 Hz, 1H), 4.17 (dd, J=9.8, 5.4 Hz, 1H), 1.84 (s, 3H). m.p. 82.3-83.4° C.

Example 4

3-(4-(6-fluoro-1H-indol-3-yl)-1H-pyrazol-1-yl)azetidine-1-carboxamide

Step 1: 3-(4-(6-fluoro-1-(phenylsulfonyl)-1H-indol-3-yl)-1H-pyrazol-1-yl)azetidine-1-carboxamide A mixture of 3-(1-(azetidin-3-yl)-1H-pyrazol-4-yl)-6-fluoro-1-(phenylsulfonyl)-1H-indole hydrochloride (Intermediate 24; 350 mg; 0.81 mmol), Et$_3$N (0.34 ml; 2.44 mmol) and TMSNCO (121 mg; 1.05 mmol) was stirred for 1.5 hours. The reaction mixture was concentrated to afford 355 mg (100%) of the title compound as a brown solid, which was used directly without further purification.
LC-MS: m/z 440 [M+H]$^+$.

Step 2

Following the general method as outlined in Example 70, starting from 3-(4-(6-fluoro-1-(phenylsulfonyl)-1H-indol-3-yl)-1H-pyrazol-1-yl)azetidine-1-carboxamide (Step 1; 355 mg; 0.81 mmol), 90 mg (37%) of the title compound was obtained as a yellow solid after purification by preparative HPLC.
$^1$H NMR (400 MHz, DMSO-d$_6$) δ [ppm]: 11.21 (s, 1H), 8.24 (s, 1H), 7.92 (s, 1H), 7.79 (dd, J=8.7, 5.4 Hz, 1H), 7.58 (d, J=2.3 Hz, 1H), 7.17 (dd, J=10.1, 2.3 Hz, 1H), 6.97-6.86 (m, 1H), 6.00 (s, 2H), 5.28-5.14 (m, 1H), 4.24 (t, J=8.3 Hz, 2H), 4.15 (dd, J=8.6, 5.7 Hz, 2H). m.p. 263.5-264.2° C.

Example 5

3-(4-(6-fluoro-1H-indol-3-yl)-1H-pyrazol-1-yl)-N-methylazetidine-1-carboxamide

Step 1: 3-(4-(6-fluoro-1-(phenylsulfonyl)-1H-indol-3-yl)-1H-pyrazol-1-yl)-N-methylazetidine-1-carboxamide A mixture of CDI (62 mg; 0.38 mmol) and MeNH$_2$ (0.20 ml; 0.40 mmol; 2.0 M in THF) of THF (10 mL) was stirred for 1 hour and added a premixed mixture of 3-(1-(azetidin-3-yl)-1H-pyrazol-4-yl)-6-fluoro-1-(phenylsulfonyl)-1H-indole hydrochloride (Intermediate 24; 200 mg; 0.46 mmol) and Et$_3$N (0.10 ml; 0.72 mmol) in THF (2 mL) was stirred at rt for 10 min. The reaction mixture was stirred overnight and concentrated. The residue was diluted with EtOAc (50 mL), washed with water (20 mL), dried over anhydrous Na$_2$SO$_4$, filtered, and concentrated to afford 174 mg (100%) of the title compound as a yellow oil, which was used directly without further purification.
LC-MS: m/z 454 [M+H]$^+$.

Step 2

Following the general method as outlined in Example 70, starting from 3-(4-(6-fluoro-1-(phenylsulfonyl)-1H-indol-3-yl)-1H-pyrazol-1-yl)-N-methylazetidine-1-carboxamide (Step 1; 174 mg; 0.38 mmol), 61 mg (51%) of the title compound was obtained as a white solid after purification by preparative HPLC.
$^1$H NMR (400 MHz, DMSO-d$_6$) δ [ppm]: 11.22 (s, 1H), 8.25 (s, 1H), 7.91 (s, 1H), 7.79 (dd, J=9.0, 5.4 Hz, 1H), 7.58 (d, J=2.1 Hz, 1H), 7.17 (dd, J=10.0, 2.0 Hz, 1H), 6.91 (dd, J=13.2, 5.4 Hz, 1H), 6.39 (d, J=5.0 Hz, 1H), 5.22 (dd, J=9.3, 3.5 Hz, 1H), 4.23 (t, J=8.1 Hz, 2H), 4.19-4.12 (m, 2H), 2.58 (t, J=4.4 Hz, 3H). m.p. 69.3-70.1° C.

Example 6

3-(1-(azetidin-3-ylmethyl)-1H-pyrazol-4-yl)-6-fluoro-1H-indole

Following the general method as outlined in Example 70, starting from 3-(1-(azetidin-3-ylmethyl)-1H-pyrazol-4-yl)-6-fluoro-1-(phenylsulfonyl)-1H-indole (Intermediate 38; 265 mg; 0.65 mmol), 80 mg (46%) of the title compound was obtained as a white solid after purification by preparative HPLC.

LC-MS: m/z 271.1 [M+H]$^+$.
$^1$H NMR (400 MHz, MeOH-d$_4$) δ [ppm]: 8.03 (s, 1H), 7.86 (s, 1H), 7.72 (dd, J=8.7, 5.3 Hz, 1H), 7.43 (s, 1H), 7.12 (dd, J=9.9, 2.3 Hz, 1H), 6.90 (ddd, J=9.6, 8.8, 2.3 Hz, 1H), 4.48 (d, J=6.6 Hz, 2H), 4.13 (dt, J=19.1, 11.4 Hz, 3H), 3.51 (dd, J=14.1, 7.1 Hz, 1H).

Example 7

3-(4-(6-fluoro-1H-indol-3-yl)-1H-pyrazol-1-yl)propanamide

Step 1: 3-(4-(6-fluoro-1-(phenylsulfonyl)-1H-indol-3-yl)-1H-pyrazol-1-yl)propanamide A mixture of 6-fluoro-1-(phenylsulfonyl)-3-(1H-pyrazol-4-yl)-1H-indole (Intermediate 5; 225 mg; 0.66 mmol), 3-bromopropanamide (302 mg; 1.99 mmol), KI (20 mg; 0.12 mmol) and K$_2$CO$_3$ (274 mg; 1.98 mmol) in CH$_3$CN (20 mL) and DMF (10 mL) was stirred at 100° C. overnight. The reaction mixture was cooled to r.t., filtered, and concentrated to afford 272 mg (100%) of the title compound as a white solid, which was used directly without further purification.
LC-MS: m/z 413.1 [M+H]$^+$.

Step 2

Following the general method as outlined in Example 70, starting from 3-(4-(6-fluoro-1-(phenylsulfonyl)-1H-indol-3-yl)-1H-pyrazol-1-yl)propanamide (Step 1; 272 mg; 0.66 mmol), 150 mg (83%) of the title compound was obtained as a white solid after purification by preparative HPLC.
LC-MS: m/z 273.1 [M+H]$^+$.
$^1$H NMR (400 MHz, DMSO-d$_6$) δ [ppm]: 11.17 (s, 1H), 8.03 (s, 1H), 7.77 (s, 1H), 7.73 (dd, J=8.7, 5.4 Hz, 1H), 7.53 (d, J=2.2 Hz, 1H), 7.41 (s, 1H), 7.16 (dd, J=10.0, 2.3 Hz, 1H), 6.96-6.81 (m, 2H), 4.33 (t, J=7.0 Hz, 2H), 2.67 (t, J=7.0 Hz, 2H). m.p. 173.3-175.0° C.

Example 8

3-(4-(5,6-difluoro-1H-indol-3-yl)-1H-pyrazol-1-yl)propanamide

Step 1: 3-(4-(5,6-difluoro-1-(phenylsulfonyl)-1H-indol-3-yl)-1H-pyrazol-1-yl)propanamide Following the general method as outlined in Example 7, starting from 5,6-difluoro-1-(phenylsulfonyl)-3-(1H-pyrazol-4-yl)-1H-indole hydrochloride (Intermediate 30; 180 mg; 0.45 mmol), 600 mg (>100%) of the title compound as a white solid, which was used directly without further purification.
LC-MS: m/z 431.1 [M+H]$^+$.

Step 2

Following the general method as outlined in Example 70, starting from 3-(4-(5,6-difluoro-1-(phenylsulfonyl)-1H-indol-3-yl)-1H-pyrazol-1-yl)propanamide (Step 1; 500 mg), 34.5 mg (26%) of the title compound was obtained as a white solid after purification by reverse phase flash chromatography.
$^1$H NMR (400 MHz, DMSO-d$_6$) δ [ppm]: 11.26 (s, 1H), 8.09 (s, 1H), 7.78 (s, 1H), 7.71 (dd, J=11.6, 8.0 Hz, 1H), 7.61 (s, 1H), 7.39 (dd, J=11.2, 7.0 Hz, 2H), 6.89 (s, 1H), 4.33 (t, J=7.0 Hz, 2H), 2.67 (t, J=7.0 Hz, 2H).

$^{19}$F NMR (377 MHz, DMSO-d$_6$) δ [ppm]: −145.50 (d, J=22.2 Hz, 1H), −148.62 (d, J=22.1 Hz, 1H). m.p. 214.9-215.5° C.

Example 13

N-(2-(dimethylamino)ethyl)-3-(4-(6-fluoro-1H-indol-3-yl)-1H-pyrazol-1-yl)propanamide Following the general method as outlined in Example 39, starting from 3-(4-(6-fluoro-1H-indol-3-yl)-1H-pyrazol-1-yl)propanoic acid (Example 24; 110 mg; 0.40 mmol) and N,N-dimethylethylenediamine (0.08 mL; 0.8 mmol), 20 mg (15%) of the title product was obtained as a yellow solid purified by preparative HPLC.

$^1$H NMR (400 MHz, MeOH-d$_4$) δ [ppm]: 7.88 (s, 1H), 7.80 (s, 1H), 7.70 (d, J=14.0 Hz, 1H), 7.40 (s, 1H), 7.11 (d, J=7.6 Hz, 1H), 6.88 (dd, J=10.0, 8.4 Hz, 1H), 4.49 (t, J=6.5 Hz, 2H), 3.27 (t, J=6.9 Hz, 2H), 2.77 (t, J=6.5 Hz, 2H), 2.31 (t, J=6.9 Hz, 2H), 2.13 (s, 6H).

Example 14

3-(4-(6-fluoro-1H-indol-3-yl)-1H-pyrazol-1-yl)-N-methylpropanamide

Following the general method as outlined in Example 39, starting from 3-(4-(6-fluoro-1H-indol-3-yl)-1H-pyrazol-1-yl)propanoic acid (Example 24; 200 mg; 0.73 mmol), 43 mg (21%) of the title product was obtained as a yellow solid purified by preparative TLC (DCM/MeOH=10/1).

$^1$H NMR (400 MHz, DMSO-d$_6$) δ [ppm]: 11.17 (s, 1H), 8.02 (s, 1H), 7.88 (d, J=3.2 Hz, 1H), 7.79-7.70 (m, 2H), 7.53 (d, J=2.2 Hz, 1H), 7.16 (dd, J=10.1, 2.1 Hz, 1H), 6.95-6.87 (m, 1H), 4.35 (t, J=7.0 Hz, 2H), 2.67 (t, J=7.0 Hz, 2H), 2.57 (d, J=4.6 Hz, 3H). m.p. 185.3-186.0° C.

Example 15

3-(4-(6-fluoro-1H-indol-3-yl)-1H-pyrazol-1-yl)-N,N-dimethylpropanamide

Following the general method as outlined in Example 40, starting from 3-(4-(6-fluoro-1H-indol-3-yl)-1H-pyrazol-1-yl)propanoic acid (Example 24; 200 mg; 0.73 mmol), 40 mg (18%) of the title compound was obtained as a light-yellow solid after purification by preparative TLC (DCM/MeOH=30/1).

$^1$H NMR (300 MHz, DMSO-d$_6$) δ [ppm]: 11.16 (s, 1H), 8.08 (s, 1H), 7.81-7.69 (m, 2H), 7.53 (d, J=2.2 Hz, 1H), 7.16 (dd, J=10.1, 2.2 Hz, 1H), 6.91 (s, 1H), 4.35 (t, J=7.0 Hz, 2H), 2.97-2.87 (m, 5H), 2.82 (s, 3H). m.p. 157.2-158.1° C.

Example 16

3-(4-(6-fluoro-1H-indol-3-yl)-1H-pyrazol-1-yl)propanoic acid

Step 1: tert-butyl 3-(4-(6-fluoro-1-(phenylsulfonyl)-1H-indol-3-yl)-1H-pyrazol-1-yl)propanoate A mixture of 6-fluoro-1-(phenylsulfonyl)-3-(1H-pyrazol-4-yl)-1H-indole (Intermediate 5; 100 mg; 0.29 mmol), tert-butyl acrylate (77 mg; 0.60 mmol) and Cs$_2$CO$_3$ (293 mg; 0.90 mmol) in MeCN (10 mL) was stirring at 80° C. overnight under nitrogen. The reaction mixture was filtered to remove solid and concentrated to afford 112 mg (82%) of the title compound as a yellow solid, which was used directly without further purification.

LC-MS: m/z 470.1 [M+H]$^+$.

Step 2

Following the general method as outlined in Example 70, starting from tert-butyl 3-(4-(6-fluoro-1-(phenylsulfonyl)-1H-indol-3-yl)-1H-pyrazol-1-yl)propanoate (Step 1; 112 mg; 0.24 mmol), 62 mg (96%) of the title compound was obtained as a yellow solid after aqueous acid base extraction and concentration without further purification.

$^1$H NMR (400 MHz, DMSO-d$_6$) δ [ppm]: 12.38 (s, 1H), 11.17 (s, 1H), 8.08 (s, 1H), 7.80-7.70 (m, 2H), 7.53 (d, J=2.4 Hz, 1H), 7.16 (dd, J=10.0, 2.4 Hz, 1H), 6.96-6.86 (m, 1H), 4.35 (t, J=6.8 Hz, 2H), 2.84 (t, J=6.8 Hz, 2H).

Example 17

3-(4-(5,6-difluoro-1H-indol-3-yl)-1H-pyrazol-1-yl)propanoic acid

The title compound (28.6 mg; 22%) was obtained as a white solid after purification by reverse phase flash chromatography in step 2 of Example 55.

$^1$H NMR (400 MHz, DMSO-d$_6$) δ [ppm]: 11.28 (s, 1H), 8.12 (s, 1H), 7.77 (s, 1H), 7.71 (dd, J=11.7, 7.9 Hz, 1H), 7.60 (d, J=2.4 Hz, 1H), 7.38 (dd, J=11.2, 7.1 Hz, 1H), 4.31 (t, J=7.0 Hz, 2H), 2.73 (t, J=7.0 Hz, 3H).

$^{19}$F NMR (377 MHz, DMSO-d$_6$) δ [ppm]: −145.55 (d, J=22.1 Hz, 1H), −148.66 (d, J=22.3 Hz, 1H).

Example 18

1-(2-(4-(6-fluoro-1H-indol-3-yl)-1H-pyrazol-1-yl)ethyl)imidazolidin-2-one

Step 1: 1-(2-(4-(6-fluoro-1-(phenylsulfonyl)-1H-indol-3-yl)-1H-pyrazol-1-yl)ethyl)imidazolidin-2-one A mixture of 6-fluoro-1-(phenylsulfonyl)-3-(1H-pyrazol-4-yl)-1H-indole (Intermediate 5; 300 mg; 0.88 mmol), 2-(2-oxoimidazolidin-1-yl)ethyl methanesulfonate (Intermediate 31; 274 mg; 1.32 mmol), NaHCO$_3$ (403 mg; 4.80 mmol) in EtOH (10 mL) was stirred at 90° C. overnight. The reaction mixture was concentrated, diluted with EtOAc (30 mL), washed with water (30 mL), brine (30 mL), dried over anhydrous Na$_2$SO$_4$, filtered, and concentrated to afford 100 mg (25%) of the title compound as a yellow solid, which was used directly used without further purification.

LC-MS: m/z 454.1 [M+H]$^+$.

Step 2

Following the general method as outlined in Example 70, starting from 1-(2-(4-(6-fluoro-1-(phenylsulfonyl)-1H-indol-3-yl)-1H-pyrazol-1-yl)ethyl)imidazolidin-2-one (Step 1; 100 mg; 0.22 mmol), 24 mg (35%) of the title compound was obtained as a yellow solid after purification by preparative HPLC.

$^1$H NMR (400 MHz, DMSO-d$_6$) δ [ppm]: 11.18 (s, 1H), 8.14 (s, 1H), 7.84-7.71 (m, 2H), 7.55 (d, J=2.3 Hz, 1H), 7.16 (dd, J=10.1, 2.3 Hz, 1H), 6.91 (td, J=9.7, 2.4 Hz, 1H), 6.33 (s, 1H), 4.24 (t, J=6.1 Hz, 2H), 3.49 (t, J=6.1 Hz, 2H), 3.16 (s, 4H).

Example 19

6-fluoro-3-(1-(2-(4-methylpiperazin-1-yl)ethyl)-1H-pyrazol-4-yl)-1H-indole

Step 1: 6-fluoro-3-(1-(2-(4-methylpiperazin-1-yl)ethyl)-1H-pyrazol-4-yl)-1-(phenylsulfonyl)-1H-indole To a solution of 3-(1-(2-bromoethyl)-1H-pyrazol-4-yl)-6-fluoro-1-(phenylsulfonyl)-1H-indole (Intermediate 22; 100 mg; 0.22 mmol) in MeCN (10 mL) was added 1-methylpiperazine (44 mg; 0.44 mmol), $K_2CO_3$ (62 mg; 0.45 mmol), and NaI (33 mg; 0.22 mmol). The mixture was stirred at 80° C. for 4 hours, filtered, concentrated, and purified by preparative TLC (DCM/MeOH=10/1) to afford 70 mg (68%) of the title compound as a yellow solid.

$^1$H NMR (300 MHz, DMSO-$d_6$) δ [ppm]: 8.32 (s, 1H), 8.05-8.03 (m, 3H), 7.95 (s, 1H), 7.89-7.85 (m, 1H), 7.79-7.68 (m, 2H). 7.63-7.57 (m, 2H), 7.26-7.19 (m, 1H), 4.26-4.22 (t, 2H), 2.76-2.71 (t, 2H), 2.50-2.27 (m, 8H), 2.15 (s, 3H).

Step 2

Following the general method as outlined in Example 70, starting from 6-fluoro-3-(1-(2-(4-methylpiperazin-1-yl)ethyl)-1H-pyrazol-4-yl)-1-(phenylsulfonyl)-1H-indole (Step 1; 80 mg; 0.17 mmol), 31 mg (55%) of the title compound was obtained as a yellow solid after purification by preparative TLC (DCM/MeOH=10/1).

$^1$H NMR (300 MHz, DMSO-$d_6$) δ [ppm]: 11.25 (s, 1H), 8.13 (s, 1H), 7.75-7.72 (m, 2H), 7.54-7.53 (d, 1H), 7.19-7.15 (m, 1H), 6.94-6.87 (m, 1H), 4.28-4.24 (t, 2H), 2.92-2.52 (m, 8H), 2.52-2.50 (t, 2H), 2.49 (s, 3H).

Example 20

4-(2-(4-(6-fluoro-1H-indol-3-yl)-1H-pyrazol-1-yl)ethyl)morpholine

Step 1: 4-(2-(4-(6-fluoro-1-(phenylsulfonyl)-1H-indol-3-yl)-1H-pyrazol-1-yl)ethyl)morpholine Following the general method as outlined in Example 41 Step 1, starting from 6-fluoro-1-(phenylsulfonyl)-3-(1H-pyrazol-4-yl)-1H-indole (Intermediate 5; 250 mg; 0.73 mmol) and 4-(2-chloroethyl)-morpholine hydrochloride (272 mg; 1.46 mmol), 233 mg (70%) of the title compound was obtained as a brown solid after purification by a silica gel chromatography (petroleum ether/EtOAc=1/1).

$^1$H NMR (300 MHz, DMSO-$d_6$) δ [ppm]: 8.34 (s, 1H), 8.11-8.02 (m, 3H), 7.97 (s, 1H), 7.88 (dd, J=8.8, 5.3 Hz, 1H), 7.82-7.67 (m, 2H), 7.61 (t, J=7.5 Hz, 2H), 7.29-7.19 (m, 1H), 4.26 (t, J=6.6 Hz, 2H), 3.57-3.51 (m, 4H), 2.74 (dd, J=8.8, 4.4 Hz, 2H), 2.42 (s, 4H).

Step 2

Following the general method as outlined in Example 70, starting from 4-(2-(4-(6-fluoro-1-(phenylsulfonyl)-1H-indol-3-yl)-1H-pyrazol-1-yl)ethyl)morpholine (Step 1; 233 mg; 0.51 mmol), 91 mg (57%) of the title compound was obtained as a yellow solid after purification by preparative HPLC.

$^1$H NMR (300 MHz, DMSO-$d_6$) δ [ppm]: 11.17 (s, 1H), 8.12 (s, 1H), 7.82-7.69 (m, 2H), 7.54 (d, J=2.4 Hz, 1H), 7.17 (dd, J=10.1, 2.2 Hz, 1H), 6.98-6.84 (m, 1H), 4.26 (t, J=6.6 Hz, 2H), 3.62-3.51 (m, 4H), 2.75 (t, J=6.6 Hz, 2H), 2.47-2.38 (m, 4H). m.p. 144.2-1145.6° C.

Example 21

N-(2-(4-(6-fluoro-1H-indol-3-yl)-1H-pyrazol-1-yl)ethyl)acetamide

Step 1: N-(2-(4-(6-fluoro-1-(phenylsulfonyl)-1H-indol-3-yl)-1H-pyrazol-1-yl)ethyl)acetamide To the solution of 2-(4-(6-fluoro-1-(phenylsulfonyl)-1H-indol-3-yl)-1H-pyrazol-1-yl)ethanamine hydrochloride (Intermediate 19; 260 mg; 0.62 mmol) in pyridine (3 mL), was added $Ac_2O$ (2.00 mL; 2.13 mmol) under nitrogen. The reaction mixture was stirred overnight. The reaction mixture was concentrated and the residue was triturated with a small amount of EtOAc to afford 150 mg (52%) of the title compound as a red solid, which was used directly without further purification.

$^1$H NMR (400 MHz, DMSO-$d_6$) δ [ppm]: 8.31 (s, 1H), 8.09 (s, 1H), 8.05 (d, J=7.9 Hz, 2H), 8.02-7.94 (m, 2H), 7.91 (dd, J=8.7, 5.3 Hz, 1H), 7.77 (dd, J=9.9, 1.9 Hz, 1H), 7.71 (t, J=7.4 Hz, 1H), 7.61 (t, J=7.7 Hz, 2H), 7.23 (td, J=8.9, 1.9 Hz, 1H), 4.19 (t, J=6.2 Hz, 2H), 3.47 (q, J=5.9 Hz, 2H), 1.79 (s, 3H).

Step 2

Following the general method as outlined in Example 70, starting from N-(2-(4-(6-fluoro-1-(phenylsulfonyl)-1H-indol-3-yl)-1H-pyrazol-1-yl)ethyl)acetamide (Step 1; 150 mg; 0.35 mmol), 66 mg (66%) of the title compound was obtained as a white solid after purification by preparative HPLC.

LC-MS: m/z 287.2 [M+H]$^+$.

$^1$H NMR (400 MHz, DMSO-$d_6$) δ [ppm]: 11.17 (s, 1H), 8.08 (s, 1H), 8.01 (t, J=5.4 Hz, 1H), 7.80 (s, 1H), 7.77 (dd, J=8.7, 5.4 Hz, 1H), 7.54 (d, J=2.2 Hz, 1H), 7.16 (dd, J=10.1, 2.2 Hz, 1H), 6.98-6.82 (m, 1H), 4.18 (t, J=6.3 Hz, 2H), 3.47 (q, J=6.1 Hz, 2H), 1.80 (s, 3H). m.p. 179.5-180.8° C.

Example 22

1-(2-(4-(6-fluoro-1H-indol-3-yl)-1H-pyrazol-1-yl)ethyl)urea

Step 1: 1-(2-(4-(6-fluoro-1-(phenylsulfonyl)-1H-indol-3-yl)-1H-pyrazol-1-yl)ethyl)urea Following the general method as outlined in Example 4, starting from 2-(4-(6-fluoro-1-(phenylsulfonyl)-1H-indol-3-yl)-1H-pyrazol-1-yl)ethanamine hydrochloride (Intermediate 19; 100 mg; 0.24 mmol), 161 mg (>100%) of the title compound was obtained as a yellow solid, which used directly without further purification.

LC-MS: m/z 428.1 [M+H]$^+$.

Step 2

Following the general method as outlined in Example 70, starting from 1-(2-(4-(6-fluoro-1-(phenylsulfonyl)-1H-indol-3-yl)-1H-pyrazol-1-yl)ethyl)urea (Step 1; 161 mg), 41 mg (60%) of the title compound was obtained as a yellow solid after purification by preparative TLC (EtOAc).

$^1$H NMR (400 MHz, DMSO-$d_6$) δ [ppm]: 1.21 (s, 1H), 8.07 (s, 1H), 7.79 (s, 1H), 7.77 (dd, J=8.7, 5.5 Hz, 1H), 7.53 (d, J=2.3 Hz, 1H), 7.16 (dd, J=10.1, 2.3 Hz, 1H), 6.93-6.86 (m, 1H), 6.08 (t, J=6.0 Hz, 1H), 5.54 (s, 2H), 4.15 (t, J=6.1 Hz, 2H), 3.42 (dd, J=12.3, 6.1 Hz, 2H).

Example 23

1-(2-(4-(6-fluoro-1H-indol-3-yl)-1H-pyrazol-1-yl)ethyl)-3-methylurea

Step 1: 2-(4-(6-fluoro-1H-indol-3-yl)-1H-pyrazol-1-yl)ethanamine

Following the general method as outlined in Example 70, starting from 2-(4-(6-fluoro-1-(phenylsulfonyl)-1H-indol-3-yl)-1H-pyrazol-1-yl)ethanamine hydrochloride (Intermediate 19; 427 mg; 1.01 mmol), 169 mg (68%) of the title compound was obtained as a yellow oil after purification by preparative TLC (DCM/MeOH=20/1).
LC-MS: m/z 245.1 [M+H]$^+$.

Step 2

Following the general method as outlined in Example 5, starting from 2-(4-(6-fluoro-1H-indol-3-yl)-1H-pyrazol-1-yl)ethanamine (Step 1; 113 mg; 0.46 mmol), 21.4 mg (15%) of the title compound was obtained as a yellow solid after purification by preparative HPLC.
$^1$H NMR (400 MHz, DMSO-d$_6$) δ [ppm]: 11.15 (s, 1H), 8.06 (s, 1H), 7.79 (s, 1H), 7.76 (dd, J=8.7, 5.4 Hz, 1H), 7.75 (s, 1H), 7.53 (d, J=2.3 Hz, 1H), 7.16 (dd, J=10.0, 2.3 Hz, 1H), 6.90 (td, J=9.6, 2.3 Hz, 1H), 5.96 (t, J=5.7 Hz, 1H), 5.84 (d, J=4.5 Hz, 1H), 4.15 (t, J=6.2 Hz, 2H), 3.45 (q, J=6.1 Hz, 2H), 2.54 (d, J=4.7 Hz, 3H). m.p. 197.6-198.7° C.

Example 24

2-(4-(6-fluoro-1H-indol-3-yl)-1H-pyrazol-1-yl)-N-methylethanamine

To a slurry of LiAlH$_4$ (100 mg; 2.64 mmol) in THF (4 mL) was added a solution of tert-butyl 2-(4-(6-fluoro-1-(phenylsulfonyl)-1H-indol-3-yl)-1H-pyrazol-1-yl)ethylcarbamate (Intermediate 18; 300 mg; 0.62 mmol) in THF (6 mL) dropwise under argon. The reaction mixture was stirred at r.t. overnight and then at reflux for 4 hours. The reaction was added sequentially water (0.1 mL), 10% aqueous NaOH (0.2 mL), water (5 mL), filtered and washed with EtOAc. The filtrate was extracted with EtOAc (30 mL×2). The combined organic layers were dried over anhydrous Na$_2$SO$_4$, filtered, concentrated, and purified by a silica gel chromatography (DCM/MeOH=20/1) to afford the 94 mg (62%) of title compound as a yellow solid.
LC-MS: m/z 259 [M+H]$^+$.
$^1$H NMR (400 MHz, DMSO-d$_6$) δ [ppm]: 11.15 (s, 1H), 8.08 (s, 1H), 7.77 (s, 1H), 7.76-7.73 (m, 1H), 7.53 (d, J=2.4 Hz, 1H), 7.16 (dd, J=10.1, 2.4 Hz, 1H), 6.93-6.87 (m, 1H), 4.19 (t, J=6.4 Hz, 2H), 2.90 (t, J=6.4 Hz, 2H), 2.30 (s, 3H). m.p. 94.2-95.2° C.

Example 25

N-(2-(4-(6-fluoro-1H-indol-3-yl)-1H-pyrazol-1-yl)ethyl)methanesulfonamide

Step 1: N-(2-(4-(6-fluoro-1-(phenylsulfonyl)-1H-indol-3-yl)-1H-pyrazol-1-yl)ethyl)methanesulfonamide To the solution of 2-(4-(6-fluoro-1-(phenylsulfonyl)-1H-indol-3-yl)-1H-pyrazol-1-yl)ethanamine hydrochloride (Intermediate 19; 228 mg; 0.54 mmol) and DMAP (3 mg; 0.02 mmol) in pyridine (4 mL), was added MsCl (0.07 mL; 0.90 mmol) under nitrogen at 0° C. The reaction was warmed to r.t. and stirred overnight. The reaction mixture was concentrated and the residue was diluted with EtOAc (20 mL), washed with aqueous HCl (10 mL; 1 M), water (10 mL), brine (10 mL). The organic layer was dried over anhydrous Na$_2$SO$_4$, filtered, and concentrated to afford 300 mg of the title compound as a yellow solid, which was used directly without further purification.
LC-MS: m/z 460.8 [M–H]$^-$.

Step 2

Following the general method as outlined in Example 70, starting from N-(2-(4-(6-fluoro-1-(phenylsulfonyl)-1H-indol-3-yl)-1H-pyrazol-1-yl)ethyl)methanesulfonamide (Step 1; 300 mg; 0.65 mmol), 54 mg (26%) of the title compound was obtained as a yellow solid after purification by preparative TLC (DCM/MeOH=10/1).
LC-MS: m/z 323.1 [M+H]$^+$.
$^1$H NMR (400 MHz, DMSO-d$_6$) δ [ppm]: 8.00 (s, 1H), 7.83 (s, 1H), 7.74-7.68 (m, 1H), 7.41 (s, 1H), 7.09 (dd, J=8.0, 1.9 Hz, 1H), 6.88 (m, 1H), 4.34 (t, J=6.0 Hz, 2H), 3.57 (q, J=6.0 Hz, 2H), 2.85 (s, 3H).

Example 26

2-(4-(6-fluoro-1H-indol-3-yl)-1H-pyrazol-1-yl)ethanol

Step 1: 2-(4-(6-fluoro-1-(phenylsulfonyl)-1H-indol-3-yl)-1H-pyrazol-1-yl)ethanol A solution of 6-fluoro-1-(phenylsulfonyl)-3-(1H-pyrazol-4-yl)-1H-indole (Intermediate 5; 1.20 mg; 0.35 mmol), 2-bromoethanol (157 mg; 1.26 mmol) and K$_2$CO$_3$ (145 mg; 1.05 mmol) in MeCN (4 mL) was heated to 165° C. for 1 h in a microwave reactor. The reaction mixture was filtered and washed with MeCN. The combined filtrate was concentrated and purified by preparative TLC (petroleum ether/EtOAc=1/1) to afford 41 mg (30%) of the title compound as a yellow semi-solid.
$^1$H NMR (400 MHz, CDCl$_3$) δ [ppm]: 7.90 (d, J=7.6 Hz, 2H), 7.75 (m, 3H), 7.56 (m, 3H), 7.46 (t, J=7.7 Hz, 2H), 7.03 (td, J=8.9, 2.3 Hz, 1H), 4.31 (m, 2H), 4.05 (m, 2H).

Step 2

Following the general method as outlined in Example 70, starting from 2-(4-(6-fluoro-1-(phenylsulfonyl)-1H-indol-3-yl)-1H-pyrazol-1-yl)ethanol (Step 1; 61 mg; 0.16 mmol), 17 mg (44%) of the title compound was obtained as a yellow solid after purification by preparative TLC (petroleum ether/EtOAc=1/1).
$^1$H NMR (400 MHz, MeOH-d$_4$) δ [ppm]: 7.85 (s, 1H), 7.69 (s, 1H), 7.59 (dd, J=8.7, 5.3 Hz, 1H), 7.28 (s, 1H), 6.98 (dd, J=9.9, 2.3 Hz, 1H), 6.76 (td, J=9.5, 2.3 Hz, 1H), 4.18 (t, J=5.4 Hz, 2H), 3.83 (t, J=5.4 Hz, 2H). m.p. 140.2-140.8° C.

Example 27

6-fluoro-3-(1-(2-(piperazin-1-yl)ethyl)-1H-pyrazol-4-yl)-1H-indole

Step 1: 6-fluoro-1-(phenylsulfonyl)-3-(1-(2-(piperazin-1-yl)ethyl)-1H-pyrazol-4-yl)-1H-indole Following the general method as outlined in Example 28, starting from 3-(1-(2-bromoethyl)-1H-pyrazol-4-yl)-6- fluoro-1-(phenylsulfonyl)-1H-indole (Intermediate 22; 100 mg; 0.22 mmol) and piperazine (38 mg; 0.44 mmol), 68 mg (68%) of the title compound was obtained as a yellow solid after purification by preparative TLC (DCM/MeOH=10/1).

$^1$H NMR (400 MHz, DMSO-$d_6$) δ [ppm]: 8.32 (s, 1H), 8.08-8.04 (m, 3H), 7.96 (s, 1H), 7.89-7.85 (m, 1H), 7.78-7.75 (m, 1H). 7.72-7.68 (m, 1H), 7.62-7.58 (m, 2H), 7.25-7.20 (m, 1H), 4.26-4.23 (t, 2H), 2.77-2.72 (m, 6H), 2.43 (s, 4H).

Step 2

Following the general method as outlined in Example 70, starting from 6-fluoro-1-(phenylsulfonyl)-3-(1-(2-(piperazin-1-yl)ethyl)-1H-pyrazol-4-yl)-1H-indole (Step 1; 80 mg; 0.18 mmol), 33 mg (60%) of the title compound was obtained as a yellow solid after purification by preparative TLC (DCM/MeOH=10/1).

$^1$H NMR (400 MHz, DMSO-$d_6$) δ [ppm]: 11.20 (s, 1H), 8.117-8.116 (d, 1H), 7.76-7.73 (m, 2H), 7.539-7.533 (d, 1H), 7.18-7.15 (dd, 1H). 6.93-6.88 (m, 1H), 4.25-4.22 (t, 2H), 2.77-2.72 (m, 6H), 2.44-2.43 (d, 4H).

Example 28

1-(4-(2-(4-(6-fluoro-1H-indol-3-yl)-1H-pyrazol-1-yl) ethyl)piperazin-1-yl)ethanone Step 1: 1 (4 (2 (4 (6 fluoro-1-(phenylsulfonyl)-1H-indol-3-yl)-1H-pyrazol-1-yl)ethyl)piperazin-1-yl) ethanone Following the general method as outlined in Example 89, starting from 6-fluoro-1-(phenylsulfonyl)-3-(1-(2-(piperazin-1-yl)ethyl)-1H-pyrazol-4-yl)-1H-indole (Example 29 Step 1; 138 mg; 0.30 mmol), 140 mg (94%) of the title compound was obtained as a yellow oil, which was used directly without further purification.

LC-MS: m/z 496.2 [M+H]$^+$.

Step 2

Following the general method as outlined in Example 70, starting from 1-(4-(2-(4-(6-fluoro-1-(phenylsulfonyl)-1H-indol-3-yl)-1H-pyrazol-1-yl)ethyl)piperazin-1-yl)ethanone (Step 1; 140 mg; 0.28 mmol), 80 mg (81%) of the title compound was obtained as a yellow solid after purification by preparative TLC (DCM/MeOH=20/1).

LC-MS: m/z 356.2 [M+H]$^+$.

$^1$H NMR (400 MHz, MeOH-$d_4$) δ [ppm]: 7.87 (s, 1H), 7.67 (s, 1H), 7.58 (dd, J=8.7, 5.3 Hz, 1H), 7.28 (s, 1H), 6.98 (dd, J=9.9, 2.3 Hz, 1H), 6.76 (td, J=9.3, 2.3 Hz, 1H), 4.23 (t, J=6.4 Hz, 2H), 3.52-3.31 (m, 4H), 2.77 (t, J=6.4 Hz, 2H), 2.48-2.31 (m, 4H), 1.96 (s, 3H).

$^{19}$F NMR (377 MHz, MeOH-$d_4$) δ [ppm]: −124.26 (s, 1H).

Example 29

3-(1-(azetidin-3-yl)-1H-pyrazol-4-yl)-6-fluoro-1H-indole

Step 1: 6-fluoro-1-(phenylsulfonyl)-3-(1-(2-(pyrrolidin-1-yl)ethyl)-1H-pyrazol-4-yl)-1H-indole To a solution of 6-fluoro-1-(phenylsulfonyl)-3-(1H-pyrazol-4-yl)-1H-indole (Intermediate 5; 240 mg; 0.70 mmol) and Cs$_2$CO$_3$ (688 mg; 2.11 mmol) in DMF (20 mL) was added 1-(2-chloroethyl)-pyrrolidine (186 mg; 1.39 mmol).

The reaction mixture was stirred at 65° C. for 2 hours, cooled to r.t., diluted with 10% aqueous NH$_4$Cl (20 mL), and extracted with EtOAc (20 mL×3). The combined organic layers were washed with water (20 mL), brine (20 mL), dried over Na$_2$SO$_4$ anhydrous, and concentrated to afford 300 mg (98%) of the title compound as a yellow solid, which was used directly without further purification.

LC-MS: m/z 439.2 [M+H]$^+$.

Step 2

Following the general method as outlined in Example 70, starting from 6-fluoro-3-(1-(2-(methylsulfonyl)ethyl)-1H-pyrazol-4-yl)-1-(phenylsulfonyl)-1H-indole (Step 1; 300 mg; 0.68 mmol), 170 mg (84%) of the title compound was obtained as a brown semi-solid after recrystallization from MeOH and petroleum ether.

$^1$H NMR (400 MHz, MeOH-$d_4$) δ [ppm]: 8.09 (s, 1H), 7.90 (s, 1H), 7.74 (dd, J=8.7, 5.3 Hz, 1H), 7.45 (s, 1H), 7.12 (dd, J=9.8, 2.3 Hz, 1H), 6.90 (td, J=9.5, 2.3 Hz, 1H), 4.59 (t, J=6.0 Hz, 2H), 3.62 (t, J=6.0 Hz, 2H), 3.25 (s, 4H), 2.05 (m, 4H).

Example 30

1-(2-(4-(6-fluoro-1H-indol-3-yl)-1H-pyrazol-1-yl) ethyl)pyrrolidin-2-one

Step 1: 1-(2-(4-(6-fluoro-1-(phenylsulfonyl)-1H-indol-3-yl)-1H-pyrazol-1-yl)ethyl)pyrrolidin-2-one A mixture of 6-fluoro-1-(phenylsulfonyl)-3-(1H-pyrazol-4-yl)-1H-indole (Intermediate 5; 443 mg; 1.30 mmol), 2-(2-oxopyrrolidin-1-yl)ethyl methanesulfonate (Intermediate 43; 400 mg; 1.93 mmol), Cs$_2$CO$_3$ (1.30 g; 3.99 mmol) in DMF (10 mL) was stirred at 90° C. overnight. The reaction mixture was diluted with water (40 mL) and extracted with EtOAc (40 mL×3). The combined organic layers were washed with brine (30 mL), dried over anhydrous Na$_2$SO$_4$, filtered, and concentrated to afford 285 mg (48%) of the title compound as a brown solid, which was used directly used without further purification.

LC-MS: m/z 453.1 [M+H]$^+$.

Step 2

Following the general method as outlined in Example 70, starting from 1-(2-(4-(6-fluoro-1-(phenylsulfonyl)-1H-indol-3-yl)-1H-pyrazol-1-yl)ethyl)pyrrolidin-2-one (Step 1; 285 mg; 0.63 mmol), 23 mg (12%) of the title compound was obtained as a brown solid after purification by preparative HPLC.

$^1$H NMR (400 MHz, DMSO-$d_6$) δ [ppm]: 11.23 (s, 1H), 8.14 (s, 1H), 7.87-7.72 (m, 2H), 7.55 (s, 1H), 7.17 (d, J=9.2 Hz, 1H), 6.91 (t, J=8.8 Hz, 1H), 4.27 (t, J=9.5 Hz, 2H), 3.61 (d, J=4.5 Hz, 2H), 3.13 (t, J=6.7 Hz, 2H), 2.23-2.09 (m, 2H), 1.84 (dd, J=14.0, 7.3 Hz, 2H).

Example 31

6-fluoro-3-(1-(2-(methylsulfonyl)ethyl)-1H-pyrazol-4-yl)-1H-indole

Step 1: 6-fluoro-3-(1-(2-(methylsulfonyl)ethyl)-1H-pyrazol-4-yl)-1-(phenylsulfonyl)-1H-indole A mixture of 6-fluoro-1-(phenylsulfonyl)-3-(1H-pyrazol-4-yl)-1H-indole (Intermediate 5; 210 mg; 0.62 mmol), methyl vinyl sulfone (654 mg; 6.16 mmol) and Et$_3$N (0.26 mL; 1.85 mmol) in methanol (15 mL) was heated at 130° C. for 0.5 h in a microwave reactor. The reaction mixture was cooled to r.t., concentrated to give a residue which was triturated with MeOH (2 mL) to afford 160 mg (58%) of the title product as a white solid.

LC-MS: m/z 448.0 [M+H]$^+$.

$^1$H NMR (400 MHz, DMSO-d$_6$) δ [ppm]: 8.44 (s, 1H), 8.13 (s, 1H), 8.06 (dd, J=6.0, 2.7 Hz, 3H), 7.89 (dd, J=8.8, 5.3 Hz, 1H), 7.78 (dd, J=9.8, 2.2 Hz, 1H), 7.71 (t, J=7.5 Hz, 1H), 7.61 (t, J=7.7 Hz, 2H), 7.25 (td, J=9.1, 2.3 Hz, 1H), 4.59 (t, J=6.9 Hz, 2H), 3.75 (t, J=6.9 Hz, 2H), 2.91 (s, 3H).

Step 2

Following the general method as outlined in Example 70, starting from 6-fluoro-3-(1-(2-(methylsulfonyl)ethyl)-1H-pyrazol-4-yl)-1-(phenylsulfonyl)-1H-indole (Step 1; 160 mg; 0.36 mmol), 70 mg (63%) of the title compound was obtained as a yellow solid after purification by preparative TLC (EtOAc).

LC-MS: m/z 308.1 [M+H]$^+$.

$^1$H NMR (400 MHz, MeOH-d$_4$) δ [ppm]: 7.94 (s, 1H), 7.75 (s, 1H), 7.59 (dd, J=8.7, 5.3 Hz, 1H), 7.30 (s, 1H), 6.98 (dd, J=9.8, 2.1 Hz, 1H), 6.77 (td, J=9.7, 2.3 Hz, 1H), 4.59 (t, J=6.5 Hz, 2H), 3.64 (t, J=6.5 Hz, 2H), 2.67 (s, 3H). m.p. 153.3-155.1° C.

Example 32

5,6-difluoro-3-(1-(2-(methylsulfonyl)ethyl)-1H-pyrazol-4-yl)-1H-indole

Step 1: 5,6-difluoro-3-(1-(2-(methylsulfonyl)ethyl)-1H-pyrazol-4-yl)-1-(phenylsulfonyl)-1H-indole Following the general method as outlined in Example 31, starting from 5,6-difluoro-1-(phenylsulfonyl)-3-(1H-pyrazol-4-yl)-1H-indole hydrochloride (Intermediate 30; 320 mg; 0.81 mmol), 186 mg (49%) of the title product was obtained as a white solid.

LC-MS: m/z 466.1 [M+H]$^+$.

$^1$H NMR (400 MHz, DMSO-d$_6$) δ [ppm]: 8.47 (s, 1H), 8.21 (s, 1H), 8.05-8.07 (m, 3H), 8.04-7.98 (m, 1H), 7.94 (dd, J=10.8, 7.8 Hz, 1H), 7.72 (t, J=7.4 Hz, 1H), 7.61 (t, J=7.8 Hz, 2H), 4.58 (t, J=6.9 Hz, 2H), 3.75 (t, J=6.9 Hz, 2H), 2.91 (s, 3H).

Step 2

Following the general method as outlined in Example 70, starting from 6-fluoro-3-(1-(2-(methylsulfonyl)ethyl)-1H-pyrazol-4-yl)-1-(phenylsulfonyl)-1H-indole (Step 1; 185 mg; 0.40 mmol), 77 mg (60%) of the title compound was obtained as a yellow solid after purification by preparative HPLC.

LC-MS: m/z 326.1 [M+H]$^+$.

$^1$H NMR (400 MHz, MeOH-d$_4$) δ [ppm]: 11.30 (s, 1H), 8.27 (s, 1H), 7.86 (s, 1H), 7.75 (dd, J=11.6, 8.0 Hz, 1H), 7.65 (d, J=2.4 Hz, 1H), 7.40 (dd, J=11.2, 7.1 Hz, 1H), 4.58 (t, J=6.9 Hz, 2H), 3.76 (t, J=6.9 Hz, 2H), 2.89 (s, 3H). m.p. 170.6-171.9° C.

Example 35

3-(4-(6-fluoro-1H-indol-3-yl)-1H-pyrazol-1-yl)-2-methylpropanamide

Step 1: methyl 3-(4-(6-fluoro-1-(phenylsulfonyl)-1H-indol-3-yl)-1H-pyrazol-1-yl)-2-methylpropanoate Following the general method as outlined in Example 6 Step 1, starting from 6-fluoro-1-(phenylsulfonyl)-3-(1H-pyrazol-4-yl)-1H-indole (Intermediate 5; 683 mg; 2.00 mmol) and methyl 2-methyl-3-((methylsulfonyl)oxy)propanoate (588 mg; 3.00 mmol), 341 mg (39%) of the title compound was obtained as a colorless oil after purification by a silica gel chromatography (petroleum ether/EtOAc=3/1 to 2/1).

LC-MS: m/z 442.1 [M+H]$^+$.

Step 2: 3-(4-(6-fluoro-1-(phenylsulfonyl)-1H-indol-3-yl)-1H-pyrazol-1-yl)-2-methylpropanoic acid Following the general method as outlined in Example 6 Step 2, starting from methyl 3-(4-(6-fluoro-1-(phenylsulfonyl)-1H-indol-3-yl)-1H-pyrazol-1-yl)-2-methylpropanoate (Step 1; 341 mg; 0.77 mmol), 329 mg (100%) of the title compound was obtained as a yellow oil, which was used directly without further purification.

LC-MS: m/z 428.1 [M+H]$^+$.

Step 3: 3-(4-(6-fluoro-1-(phenylsulfonyl)-1H-indol-3-yl)-1H-pyrazol-1-yl)-2-methylpropanamide Following the general method as outlined in Example 40 Step 1, starting from 3-(4-(6-fluoro-1-(phenylsulfonyl)-1H-indol-3-yl)-1H-pyrazol-1-yl)-2-methylpropanoic acid (Step 2; 329 mg; 0.77 mmol), 328 mg (100%) of the title compound was obtained as a yellow oil, which was used directly without further purification.

LC-MS: m/z 427.1 [M+H]$^+$.

Step 4

Following the general method as outlined in Example 70, starting from 3-(4-(6-fluoro-1-(phenylsulfonyl)-1H-indol-3-yl)-1H-pyrazol-1-yl)-2-methylpropanamide (Step 3; 328 mg; 0.77 mmol), 84 mg (38%) of the racemic title compound was obtained as a white solid after purification by preparative HPLC.

The product of Example 67 (26.4 mg) was obtained as the first eluting enantiomer after chiral preparative HPLC (Chiralpak IA column, 250 mm×20 mm 5 µm; mobile phase: hexane/isopropyl alcohol/Et$_2$NH 80/20/0.3; flow: 12 mL/min).

Chiral purity (HPLC; Chiralpak IA 250 mm×4.6 mm 5 µm; Mobile phase: Hexane/IPA 70/30; flow: 1.0 mL/min; UV detaction at 230 nm; Retention time 6.10 min): 98.6% e.e.

Optical rotation: [α]$^{254}{}_D$=−7.0 (c=0.01, MeOH/MeCN=1/1).

LC-MS: m/z 287.1 [M+H]$^+$.

$^1$H NMR (400 MHz, MeOH-d$_4$) δ [ppm]: 8.11 (s, 1H), 8.01 (d, J=4.7 Hz, 1H), 7.90 (dd, J=8.7, 5.4 Hz, 1H), 7.60 (s, 1H), 7.31 (dd, J=9.9, 2.1 Hz, 1H), 7.14-7.04 (m, 1H), 4.67 (dd, J=13.8, 8.4 Hz, 2H), 4.40 (dd, J=13.7, 6.2 Hz, 2H), 3.44-3.19 (m, 3H), 1.41 (dd, J=13.8, 6.5 Hz, 3H). m.p. 184.5-185.5° C.

Example 36

3-(4-(6-fluoro-1H-indol-3-yl)-1H-pyrazol-1-yl)-2-methylpropanamide

The title compound (second eluting enantiomer, 20.6 mg) was isolated from the chiral preparative HPLC as described in Example 35.

Chiral purity (HPLC; Chiralpak IA 250 mm×4.6 mm 5 μm; Mobile phase: Hexane/IPA 70/30; flow: 1.0 mL/min; UV detaction at 230 nm; Retention time 7.39 min): 93.9% e.e.

Optical rotation $[\alpha]^{254}_D$=+0.3 (c=0.01, MeOH/MeCN=1/1).

LC-MS: m/z 287.1 [M+H]$^+$.

$^1$H NMR (400 MHz, MeOH-d$_4$) δ [ppm]: 11.16 (s, 1H), 8.01 (s, 1H), 7.78 (s, 1H), 7.72 (dd, J=8.7, 5.3 Hz, 1H), 7.53 (d, J=2.3 Hz, 1H), 7.40 (s, 1H), 7.16 (dd, J=10.0, 2.3 Hz, 1H), 6.94-6.87 (m, 1H), 6.86 (s, 1H), 4.32 (dd, J=13.5, 7.5 Hz, 1H), 4.03 (dd, J=13.4, 7.1 Hz, 1H), 2.92 (q, J=14.2, 7.1 Hz, 1H), 1.01 (d, J=7.0 Hz, 3H). m.p. 184.5-185.5° C.

Example 38

2-(4-(6-fluoro-1H-indol-3-yl)-1H-pyrazol-1-yl)acetamide

Step 1: 2-(4-(6-fluoro-1-(phenylsulfonyl)-1H-indol-3-yl)-1H-pyrazol-1-yl)acetamide Following the general method as outlined in Example 41, starting from 6-fluoro-1-(phenylsulfonyl)-3-(1H-pyrazol-4-yl)-1H-indole (Intermediate 5; 250 mg; 0.73 mmol), K$_2$CO$_3$ (274 mg; 1.98 mmol), and 2-bromoacetamide (274 mg; 1.99 mmol) and MeCN (20 mL), 241 mg (83%) of the title compound was obtained as a white solid after filtration and concentration.

LC-MS: m/z 399.1 [M+H]$^+$.

Step 2

Following the general method as outlined in Example 70, starting from 2-(4-(6-fluoro-1-(phenylsulfonyl)-1H-indol-3-yl)-1H-pyrazol-1-yl)acetamide (Step 1; 241 mg; 0.60 mmol), 13 mg (8%) of the title compound was obtained as a light yellow solid after purification by preparative TLC (DCM/MeOH=5/1).

$^1$H NMR (400 MHz, MeOH-d$_4$) δ [ppm]: 68.02 (s, 1H), 7.87 (s, 1H), 7.74 (dd, J=8.7, 5.4 Hz, 1H), 7.44 (s, 1H), 7.11 (m, 1H), 6.89 (t, J=8.0 Hz, 1H), 4.95 (s, 2H).

Example 39

2-(4-(6-fluoro-1H-indol-3-yl)-1H-pyrazol-1-yl)-N-methylacetamide

To a solution of 2-(4-(6-fluoro-1H-indol-3-yl)-1H-pyrazol-1-yl)acetic acid (Example 6; 120 mg; 0.46 mmol) in THF (25 mL) was added HATU (350 mg; 0.92 mmol) and Et$_3$N (279 mg; 2.76 mmol) under nitrogen. The reaction mixture was stirred for 10 minutes before methylamine (0.5 mL; 1.0 mmol; 2 M in THF) was added dropwise. The reaction mixture was stirred at r.t. overnight, diluted with water (20 mL) and extracted with EtOAc (20 mL×3). The combined organic layers were concentrated, and purified by preparative TLC (EtOAc) to afford 33 mg (26%) of the title product as a white solid.

$^1$H NMR (400 MHz, DMSO-d$_6$) δ [ppm]: 11.18 (s, 1H), 8.09 (s, 1H), 7.96 (m, 1H), 7.81 (s, 1H), 7.74 (dd, J=9.0, 5.5 Hz, 1H), 7.56 (d, J=2.2 Hz, 0H), 7.17 (dd, J=10.1, 2.3 Hz, 1H), 6.92 (td, J=9.7, 2.3 Hz, 1H), 4.79 (s, 2H), 2.63 (d, J=4.6 Hz, 3H). m.p. 259.2-260.1° C.

Example 40

2-(4-(6-fluoro-1H-indol-3-yl)-1H-pyrazol-1-yl)-N,N-dimethylacetamide

Following the general method as outlined in Example 39, starting from 2-(4-(6-fluoro-1H-indol-3-yl)-1H-pyrazol-1-yl)acetic acid (Example 6; 120 mg; 0.46 mmol) and dimethylamine (0.5 mL; 1.0 mmol; 2 M in THF), 22 mg (17%) of the title compound was obtained as a white solid after purification by preparative TLC (EtOAc).

$^1$H NMR (300 MHz, DMSO-d$_6$) δ [ppm]: 11.18 (s, 1H), 8.01 (s, 1H), 7.73 (m, 2H), 7.56 (d, J=2.4 Hz, 1H), 7.17 (dd, J=10.0, 2.3 Hz, 1H), 6.91 (td, J=9.7, 2.3 Hz, 1H), 5.12 (s, 2H), 3.06 (s, 3H), 2.87 (s, 3H). m.p. 250.9-251.4° C.

Example 41

2-(4-(6-fluoro-1H-indol-3-yl)-1H-pyrazol-1-yl)acetic acid

Step 1: ethyl 2-(4-(6-fluoro-1-(phenylsulfonyl)-1H-indol-3-yl)-1H-pyrazol-1-yl)acetate To a solution of 6-fluoro-1-(phenylsulfonyl)-3-(1H-pyrazol-4-yl)-1H-indole (Intermediate 5; 1.00 g; 2.93 mmol) and K$_2$CO$_3$ (1.30 g; 9.41 mmol) in DMF (40 mL) was added ethyl bromoacetate (1.50 g; 8.98 mmol). The mixture was stirred at 70° C. for 2 hours, cooled to r.t., diluted with 10% aqueous NH$_4$Cl (20 mL) and extracted with EtOAc (20 mL×3). The combined organic layers were washed with water (20 mL), brine (20 mL), dried over anhydrous Na$_2$SO$_4$, filtered, and concentrated to afford 1.10 g (88%) of the title compound as a yellow solid, which was used directly without further purification.

$^1$H NMR (300 MHz, DMSO-d$_6$) δ [ppm]: 8.36 (s, 1H), 8.15 (s, 1H), 8.05 (m, 3H), 7.78 (m, 3H), 7.61 (t, J=7.6 Hz, 2H), 7.24 (td, J=9.1, 2.3 Hz, 1H), 5.10 (s, 2H), 4.17 (q, J=7.1 Hz, 2H), 1.22 (t, J=7.1 Hz, 3H).

Step 2

Following the general method as outlined in Example 70, starting from ethyl 2-(4-(6-fluoro-1-(phenylsulfonyl)-1H-indol-3-yl)-1H-pyrazol-1-yl)acetate (Step 1; 1.10 g; 2.57 mmol), 673 mg (100%) of the title compound was obtained as a white solid.

$^1$H NMR (400 MHz, DMSO-d$_6$) δ [ppm]: 13.07 (d, J=1.7 Hz, 1H), 11.28 (s, 1H), 8.12 (s, 1H), 7.81 (s, 1H), 7.73 (dd, J=8.7, 5.4 Hz, 1H), 7.57 (d, J=2.3 Hz, 1H), 7.18 (dd, J=9.8, 2.2 Hz, 1H), 6.92 (td, J=9.8, 2.3 Hz, 1H), 4.98 (s, 2H).

Example 42 methyl 2-(4-(6-fluoro-1H-indol-3-yl)-1H-pyrazol-1-yl)acetate

To a solution of 2-(4-(6-fluoro-1H-indol-3-yl)-1H-pyrazol-1-yl)acetic acid (Example 6; 100 mg; 0.39 mmol) in MeOH (10 mL) was added concentrated sulfuric acid (0.02 mL; 0.39 mmol). The mixture was stirred at 85° C. overnight, cooled to r.t., poured into water, extracted with EtOAc (10 mL×3). The combined organic layers were washed with brine, dried over anhydrous $Na_2SO_4$, concentrated, and purified by preparative TLC (petroleum ether/EtOAc=1/1) to afford 33 mg (31%) of the title compound as a white solid.

$^1$H NMR (400 MHz, DMSO-$d_6$) δ [ppm]: δ 11.21 (s, 1H), 8.14 (s, 1H), 7.84 (s, 1H), 7.73 (dd, J=8.4, 5.5 Hz, 1H), 7.58 (d, J=1.9 Hz, 1H), 7.18 (dd, J=9.8, 1.7 Hz, 1H), 6.98-6.87 (m, 1H), 5.10 (s, 2H), 3.70 (s, 3H).

Example 43

6-fluoro-3-(1-(piperidin-4-ylmethyl)-1H-pyrazol-4-yl)-1H-indole

Following the general method as outlined in Example 70, starting from 6-fluoro-1-(phenylsulfonyl)-3-(1-(piperidin-4-ylmethyl)-1H-pyrazol-4-yl)-1H-indole (Intermediate 21; 350 mg; 0.80 mmol), 37.2 mg (16%) of the title compound was obtained as a yellow solid after purification by reverse phase flash chromatography.

$^1$H NMR (400 MHz, DMSO-$d_6$) δ [ppm]: 11.16 (d, J=5.4 Hz, 1H), 8.07 (s, 1H), 7.83-7.72 (m, 2H), 7.53 (d, J=2.0 Hz, 1H), 7.16 (dd, J=10.1, 1.9 Hz, 1H), 6.95-6.85 (m, 1H), 3.98 (d, J=7.0 Hz, 2H), 3.44-3.35 (m, 1H), 2.90 (d, J=11.6 Hz, 2H), 2.40 (t, J=11.0 Hz, 2H), 1.91 (d, J=3.1 Hz, 1H), 1.49-1.39 (m, 2H), 1.13-1.04 (m, 2H). m.p. 106.3-107.5° C.

Example 44

5,6-difluoro-3-(1-(piperidin-4-ylmethyl)-1H-pyrazol-4-yl)-1H-indole

Following the general method as outlined in Example 70, starting from 5,6-difluoro-1-(phenylsulfonyl)-3-(1-(piperidin-4-ylmethyl)-1H-pyrazol-4-yl)-1H-indole (Intermediate 46; 830 mg), 34.8 mg (19%) of the title compound was obtained as a white solid after purification by reverse phase flash chromatography.

LC-MS: m/z 317.1 [M+H$^+$]$^+$.

$^1$H NMR (400 MHz, DMSO-$d_6$) δ [ppm]: 11.33 (s, 1H), 8.15 (s, 1H), 7.80 (s, 1H), 7.74 (dd, J=11.6, 8.0 Hz, 1H), 7.62 (s, 1H), 7.40 (dd, J=11.2, 7.1 Hz, 1H), 4.00 (d, J=7.1 Hz, 2H), 3.17 (s, 2H), 2.99 (d, J=12.2 Hz, 2H), 1.99 (ddd, J=11.5, 9.3, 5.6 Hz, 1H), 1.49 (d, J=15.3 Hz, 2H), 1.18 (qd, J=12.5, 4.2 Hz, 2H). m.p. 167.1-168.9° C.

Example 45

6-fluoro-3-(1-(2,2,2-trifluoroethyl)piperidin-4-yl)methyl)-1H-pyrazol-4-yl)-1H-indole Step 1: 6-fluoro-1-(phenylsulfonyl)-3-(1-((1-(2,2,2-trifluoroethyl)piperidin-4-yl)methyl)-1H-pyrazol-4-yl)-1H-indole A mixture of 6-fluoro-1-(phenylsulfonyl)-3-(1-(piperidin-4-ylmethyl)-1H-pyrazol-4-yl)-1H-indole (Intermediate 21; 277 mg; 0.63 mmol), Et$_3$N (0.40 mL; 2.87 mmol) and 2,2,2-trifluoroethyl trifluoromethanesulfonate (147 mg; 0.63 mmol) in toluene (40 mL) was stirred at 80° C. overnight. The reaction mixture was concentrated and purified by reverse phase flash chromatography to afford 275 mg (84%) of the title compound as a yellow oil.

LC-MS: m/z 521 [M+H]$^+$.

Step 2

Following the general method as outlined in Example 70, starting from 6-fluoro-1-(phenylsulfonyl)-3-(1-((1-(2,2,2-trifluoroethyl)piperidin-4-yl)methyl)-1H-pyrazol-4-yl)-1H-indole (Step 1; 275 mg; 0.53 mmol), 135 mg (67%) of the title compound was obtained as a yellow solid after purification by preparative HPLC.

$^1$H NMR (400 MHz, DMSO-$d_6$) δ [ppm]: 11.16 (s, 1H), 8.08 (s, 1H), 7.82-7.71 (m, 1H), 7.53 (s, 1H), 7.16 (dd, J=10.1, 2.3 Hz, 1H), 7.01-6.85 (m, 1H), 4.02 (d, J=7.1 Hz, 2H), 3.12 (dt, J=20.6, 6.9 Hz, 2H), 2.99-2.84 (m, 2H), 2.42-2.22 (m, 2H), 1.84 (ddd, J=7.3, 5.4, 2.8 Hz, 1H), 1.48 (d, J=10.6 Hz, 2H), 1.26 (ddd, J=14.0, 10.7, 2.5 Hz, 2H).

Example 46

6-fluoro-3-(1-((1-(2-fluoroethyl)piperidin-4-yl)methyl)-1H-pyrazol-4-yl)-1H-indole Step 1: 6-fluoro-3-(1-((1-(2-fluoroethyl)piperidin-4-yl)methyl)-1H-pyrazol-4-yl)-1-(phenylsulfonyl)-1H-indole Following the general method as outlined in Example 81, starting from 6-fluoro-1-(phenylsulfonyl)-3-(1-(piperidin-4-ylmethyl)-1H-pyrazol-4-yl)-1H-indole (Intermediate 21; 111 mg; 0.25 mmol) and 1-bromo-2-fluoroethane (64 mg; 0.50 mmol), 122 mg (100%) of the title compound was obtained as a yellow oil, which was used directly without further purification.

LC-MS: m/z 485 [M+H]$^+$.

Step 2

Following the general method as outlined in Example 70, starting from 6-fluoro-3-(1-((1-(2-fluoroethyl)piperidin-4-yl)methyl)-1H-pyrazol-4-yl)-1-(phenylsulfonyl)-1H-indole (Step 1; 122 mg; 0.25 mmol), 16.5 mg (19%) of the title compound was obtained as a white solid after purification by preparative HPLC.

$^1$H NMR (400 MHz, MeOH-$d_4$) δ [ppm]: 7.90 (s, 1H), 7.79 (s, 1H), 7.77-7.69 (m, 1H), 7.40 (s, 1H), 7.11 (dd, J=9.9, 2.3 Hz, 1H), 6.95-6.83 (m, 1H), 4.66-4.45 (m, 2H), 4.07 (d, J=7.2 Hz, 2H), 2.99 (d, J=11.9 Hz, 2H), 2.78-2.58 (m, 2H), 2.08 (td, J=11.9, 2.2 Hz, 2H), 1.94 (ddd, J=11.5, 7.6, 4.0 Hz, 1H), 1.60 (d, J=12.9 Hz, 2H), 1.39 (qd, J=12.6, 3.7 Hz, 2H).

Example 47

2-(4-((4-(6-fluoro-1H-indol-3-yl)-1H-pyrazol-1-yl)methylpiperidin-1-yl)ethanol

Step 1: 2-(4-((4-(6-fluoro-1-(phenylsulfonyl)-1H-indol-3-yl)-1H-pyrazol-1-yl)methyl)piperidin-1-yl)ethanol Following the general method as outlined in Example 81, starting from 6-fluoro-1-(phenylsulfonyl)-3-(1-(piperidin-4-ylmethyl)-1H-pyrazol-4-yl)-1H-indole (Intermediate 21; 200 mg; 0.46 mmol), 200 mg (91%) of the title compound was obtained as a yellow oil, which was used directly without further purification.

LC-MS: m/z 483 [M+H]$^+$.

Step 2

Following the general method as outlined in Example 70, starting from 2-(4-((4-(6-fluoro-1-(phenylsulfonyl)-1H-indol-3-yl)-1H-pyrazol-1-yl)methyl)piperidin-1-yl)ethanol (Step 1; 200 mg; 0.41 mmol), 5.2 mg (4%) of the title compound was obtained as a white solid after purification by preparative HPLC.

$^1$H NMR (400 MHz, MeOH-d$_4$) δ [ppm]: 7.82 (s, 1H), 7.67 (s, 1H), 7.58 (dd, J=8.7, 5.3 Hz, 1H), 7.28 (s, 1H), 6.98 (dd, J=9.9, 2.3 Hz, 1H), 6.87-6.70 (m, 1H), 3.98 (d, J=7.1 Hz, 2H), 3.58 (t, J=6.1 Hz, 2H), 2.90 (d, J=11.9 Hz, 2H), 2.43 (t, J=6.1 Hz, 2H), 2.06-1.93 (m, 2H), 1.86 (ddd, J=11.7, 7.7, 4.1 Hz, 1H), 1.52 (d, J=13.0 Hz, 2H), 1.37-1.19 (m, 2H).

Example 48

1,1,1-trifluoro-3-(4-((4-(6-fluoro-1H-indol-3-yl)-1H-pyrazol-1-yl)methyl)piperidin-1-yl)propan-2-ol Step 1: 1,1,1-trifluoro-3-(4-((4-(6-fluoro-1-(phenylsulfonyl)-1H-indol-3-yl)-1H-pyrazol-1-yl)methyl)piperidin-1-yl)propan-2-ol A mixture of 6-fluoro-1-(phenylsulfonyl)-3-(1-(piperidin-4-ylmethyl)-1H-pyrazol-4-yl)-1H-indole (Intermediate 21; 111 mg; 0.25 mmol), K$_2$CO$_3$ (35 mg; 0.25 mmol) and 2-(trifluoromethyl)oxirane (142 mg; 1.27 mmol) in DMF (10 mL) was stirred overnight under nitrogen. The reaction mixture was added water (20 mL) and extracted with EtOAc (50 mL×2). The combined organic layers were dried over anhydrous Na$_2$SO$_4$, filtered, concentrated, and purified by reverse phase flash chromatograph to afford 65 mg (47%) of the title compound as a yellow solid.

LC-MS: m/z 551 [M+H]$^+$.

Step 2

Following the general method as outlined in Example 70, starting from 1,1,1-trifluoro-3-(4-((4-(6-fluoro-1-(phenylsulfonyl)-1H-indol-3-yl)-1H-pyrazol-1-yl)methyl)piperidin-1-yl)propan-2-ol (Step 1; 65 mg; 0.12 mmol), 16.5 mg (34%) of the title compound was obtained as a white solid after purification by reverse phase flash chromatography.

$^1$H NMR (400 MHz, MeOH-d$_4$) δ [ppm]: 7.73 (s, 1H), 7.64 (s, 1H), 7.54 (dd, J=8.7, 5.3 Hz, 1H), 7.24 (s, 1H), 6.96 (dd, J=9.9, 2.3 Hz, 1H), 6.73 (ddd, J=9.6, 8.9, 2.3 Hz, 1H), 4.05-3.93 (m, 1H), 3.90 (d, J=7.2 Hz, 2H), 2.83 (dd, J=15.1, 12.2 Hz, 2H), 2.51-2.36 (m, 2H), 2.06-1.88 (m, 2H), 1.77 (ddt, J=15.1, 7.6, 3.7 Hz, 1H), 1.43 (d, J=13.0 Hz, 2H), 1.34-1.16 (m, 2H).

Example 49

2-(4-((4-(6-fluoro-1H-indol-3-yl)-1H-pyrazol-1-yl)methyl)piperidin-1-yl)acetic acid Step 1: ethyl 2-(4-((4-(6-fluoro-1-(phenylsulfonyl)-1H-indol-3-yl)-1H-pyrazol-1-yl)methyl)piperidin-1-yl)acetate Following the general method as outlined in Example 41, starting from 6-fluoro-1-(phenylsulfonyl)-3-(1-(piperidin-4-ylmethyl)-1H-pyrazol-4-yl)-1H-indole (Intermediate 21; 185 mg; 0.42 mmol), 330 mg of the title compound was obtained as a yellow oil after purification by reverse phase flash chromatography.

LC-MS: m/z 525 [M+H]$^+$.

Step 2

Following the general method as outlined in Example 70, starting from ethyl 2-(4-((4-(6-fluoro-1-(phenylsulfonyl)-1H-indol-3-yl)-1H-pyrazol-1-yl)methyl)piperidin-1-yl)acetate (Step 1; 330 mg; 0.63 mmol), 190 mg (85%) of the title compound was obtained as a yellow solid after purification by reverse phase flash chromatography.

$^1$H NMR (400 MHz, DMSO-d$_6$) δ [ppm]: 11.28 (s, 1H), 8.08 (s, 1H), 7.85-7.69 (m, 2H), 7.53 (d, J=2.3 Hz, 1H), 7.17 (dd, J=10.1, 2.3 Hz, 1H), 6.90 (td, J=9.5, 2.4 Hz, 1H), 4.02 (d, J=7.0 Hz, 2H), 2.99 (d, J=11.3 Hz, 2H), 2.87 (s, 2H), 2.16 (t, J=10.8 Hz, 2H), 1.86 (ddd, J=10.9, 6.1, 3.6 Hz, 1H), 1.49 (d, J=11.5 Hz, 2H), 1.44-1.21 (m, 2H). m.p. 120.3-121.5° C.

Example 50

4-(4-((4-(6-fluoro-1H-indol-3-yl)-1H-pyrazol-1-yl)methyl)piperidin-1-yl)-4-oxobutanoic acid Step 1: methyl 4-(4-((4-(6-fluoro-1-(phenylsulfonyl)-1H-indol-3-yl)-1H-pyrazol-1-yl)methyl)piperidin-1-yl)-4-oxobutanoate Following the general method as outlined in Example 83, starting from 6-fluoro-1-(phenylsulfonyl)-3-(1-(piperidin-4-ylmethyl)-1H-pyrazol-4-yl)-1H-indole (Intermediate 21; 202 mg; 0.46 mmol) and monomethyl succinate (165 mg; 0.92 mmol), 220 mg (86%) of the title compound was obtained as a yellow oil after purification by reverse phase flash chromatography.

LC-MS: m/z 553 [M+H]$^+$.

Step 2

Following the general method as outlined in Example 70, starting from methyl 4-(4-((4-(6-fluoro-1-(phenylsulfonyl)-1H-indol-3-yl)-1H-pyrazol-1-yl)methyl)piperidin-1-yl)-4-oxobutanoate (Step 1; 220 mg; 0.40 mmol), 69 mg (44%) of the title compound was obtained as a yellow solid after purification by preparative HPLC.

$^1$H NMR (400 MHz, MeOH-d$_4$) δ [ppm]: 8.01 (s, 1H), 7.86 (s, 1H), 7.76 (dd, J=8.7, 5.3 Hz, 1H), 7.46 (d, J=3.5 Hz, 1H), 7.15 (dd, J=9.9, 2.3 Hz, 1H), 7.01-6.85 (m, 1H), 4.60 (d, J=13.3 Hz, 1H), 4.14 (dd, J=19.8, 10.6 Hz, 3H), 3.23-3.06 (m, 1H), 2.78-2.62 (m, 3H), 2.55 (t, J=7.2 Hz, 2H), 2.39-2.20 (m, 1H), 1.72 (t, J=14.9 Hz, 2H), 1.46-1.15 (m, 2H). m.p. 79.2-80.1° C.

Example 51

1-(4-((4-(6-fluoro-1H-indol-3-yl)-1H-pyrazol-1-yl)methyl)piperidin-1-yl)ethanone Step 1: 1-(4-((4-(6-fluoro-1-(phenylsulfonyl)-1H-indol-3-yl)-1H-pyrazol-1-yl)methyl)piperidin-1-yl)ethanone Following the general method as outlined in Example 89, starting from 6-fluoro-1-(phenylsulfonyl)-3-(1-(piperidin-4-ylmethyl)-1H-pyrazol-4-yl)-1H-indole (Intermediate 21; 365 mg; 0.83 mmol), 400 mg (100%) of the title compound was obtained as a yellow solid, which was used directly without further purification.

LC-MS: m/z 481 [M+H]$^+$.

Step 2

Following the general method as outlined in Example 70, starting from 1-(4-((4-(6-fluoro-1-(phenylsulfonyl)-1H-indol-3-yl)-1H-pyrazol-1-yl)methyl)piperidin-1-yl)ethanone (Step 1; 400 mg; 0.83 mmol), 37.4 mg (13%) of the title compound was obtained as a yellow solid after purification by preparative HPLC.

$^1$H NMR (400 MHz, DMSO-d$_6$) δ [ppm]: δ 11.21 (d, J=5.7 Hz, 1H), 8.09 (s, 1H), 7.80-7.71 (m, 2H), 7.54 (d, J=2.4 Hz, 1H), 7.16 (dd, J=10.1, 2.3 Hz, 1H), 6.96-6.86 (m, 1H), 4.34 (dd, J=9.0, 6.9 Hz, 1H), 4.04 (d, J=7.1 Hz, 2H), 3.79 (d, J=13.3 Hz, 1H), 3.05-2.92 (m, 2H), 2.16-2.05 (m, 1H), 1.97 (s, 3H), 1.54 (m, 2H), 1.10 (m, 2H).

Example 52

3-(1-((1-cyclopropylpiperidin-4-yl)methyl)-1H-pyrazol-4-yl)-6-fluoro-1H-indole

Step 1: 3-(1-((1-cyclopropylpiperidin-4-yl)methyl)-1H-pyrazol-4-yl)-6-fluoro-1-(phenylsulfonyl)-1H-indole A mixture of 6-fluoro-1-(phenylsulfonyl)-3-(1-(piperidin-4-ylmethyl)-1H-pyrazol-4-yl)-1H-indole (Intermediate 21; 277 mg; 0.63 mmol), HOAc (121 mg; 2.01 mmol), (1-ethoxycyclopropoxy)trimethylsilane (220 mg; 1.26 mmol) and NaBH$_3$CN (60 mg; 0.95 mmol) in DCM/MeOH/THF (10 ml/1 ml/15 ml) was stirred at 70° C. overnight. The reaction mixture was added saturated aqueous NH$_4$Cl (20 mL), extracted with EtOAc (50 mL×2). The combined organic layers were dried over anhydrous Na$_2$SO$_4$, filtered, concentrated, and purified by reverse phase flash chromatography to afford 137 mg (45%) of the title compound as a yellow oil.

LC-MS: m/z 479 [M+H]$^+$.

Step 2

Following the general method as outlined in Example 70, starting from 3-(1-((1-cyclopropylpiperidin-4-yl)methyl)-1H-pyrazol-4-yl)-6-fluoro-1-(phenylsulfonyl)-1H-indole (Step 1; 137 mg; 0.29 mmol), 17 mg (18%) of the title compound was obtained as a white solid after purification by preparative HPLC.

$^1$H NMR (400 MHz, MeOH-d$_4$) δ [ppm]: 7.80 (s, 1H), 7.67 (s, 1H), 7.58 (dd, J=8.7, 5.3 Hz, 1H), 7.28 (s, 1H), 6.98 (dd, J=9.9, 2.3 Hz, 1H), 6.77 (ddd, J=9.6, 8.9, 2.4 Hz, 1H), 3.96 (d, J=7.1 Hz, 2H), 2.94 (d, J=11.9 Hz, 2H), 2.10 (td, J=12.0, 2.4 Hz, 2H), 1.93 (s, 1H), 1.58-1.43 (m, 3H), 1.20 (dd, J=12.5, 3.3 Hz, 2H), 0.44-0.25 (m, 4H).

Example 53

6-fluoro-3-(1-((1-methylpiperidin-4-yl)methyl)-1H-pyrazol-4-yl)-1H-indole

The title compound (40.7 mg; 16%) was obtained as a yellow solid after purification by reverse phase flash chromatography in step 2 of Example 21.

$^1$H NMR (400 MHz, DMSO-d$_6$) δ [ppm]: 11.16 (s, 1H), 8.08 (s, 1H), 7.81-7.70 (m, 2H), 7.53 (d, J=1.8 Hz, 1H), 7.16 (dd, J=10.0, 1.8 Hz, 1H), 6.91 (td, J=10.0, 2.1 Hz, 1H), 4.01 (d, J=7.1 Hz, 2H), 2.73 (d, J=11.5 Hz, 2H), 2.12 (s, 3H), 1.79 (m, 3H), 1.47 (d, J=11.7 Hz, 2H), 1.30-1.17 (m, 2H). m.p. 166.3-169.7° C.

Example 54

6-fluoro-3-(1-((1-(methylsulfonyl)piperidin-4-yl)methyl)-1H-pyrazol-4-yl)-1H-indole Step 1: 6-fluoro-3-(1-((1-(methylsulfonyl)piperidin-4-yl)methyl)-1H-pyrazol-4-yl)-1-(phenylsulfonyl)-1H-indole Following the general method as outlined in Example 25, starting from 6-fluoro-1-(phenylsulfonyl)-3-(1-(piperidin-4-ylmethyl)-1H-pyrazol-4-yl)-1H-indole (Intermediate 21; 276 mg; 0.63 mmol), 300 mg (92%) of the title compound was obtained as a yellow solid, which was used directly without further purification.

LC-MS: m/z 517 [M+H]$^+$.

Step 2

Following the general method as outlined in Example 70, starting from 6-fluoro-3-(1-((1-(methylsulfonyl)piperidin-4-yl)methyl)-1H-pyrazol-4-yl)-1-(phenylsulfonyl)-1H-indole (Step 1; 300 mg; 0.58 mmol), 150 mg (69%) of the title compound was obtained as a white solid after purification by preparative HPLC.

$^1$H NMR (400 MHz, DMSO-d$_6$) δ [ppm]: 11.17 (s, 1H), 8.10 (s, 1H), 7.79 (s, 1H), 7.75 (dd, J=8.6, 5.4 Hz, 1H), 7.54 (d, J=2.2 Hz, 1H), 7.16 (dd, J=10.1, 2.3 Hz, 1H), 6.99-6.83 (m, 1H), 4.08 (d, J=7.1 Hz, 2H), 3.55 (d, J=12.0 Hz, 2H), 2.83 (s, 3H), 2.76-2.61 (m, 2H), 2.07-1.91 (m, 1H), 1.64 (dd, J=8.3, 4.7 Hz, 2H), 1.28 (ddd, J=23.3, 11.8, 3.1 Hz, 2H). m.p. 82.3-83.1° C.

Example 58

6-fluoro-3-(1-((tetrahydro-2H-pyran-4-yl)methyl)-1H-pyrazol-4-yl)-1H-indole

Step 1: 6-fluoro-1-(phenylsulfonyl)-3-(1-((tetrahydro-2H-pyran-4-yl)methyl)-1H-pyrazol-4-yl)-1H-indole Following the general method as outlined in Intermediate 20, starting from 6-fluoro-1-(phenylsulfonyl)-3-(1H-pyrazol-4-yl)-1H-indole (Intermediate 5; 305 mg; 0.89 mmol) and (tetrahydro-2H-pyran-4-yl)methyl methanesulfonate (226 mg; 1.16 mmol), 398 mg of the title compound was obtained as a white solid, which was used directly without further purification.

LC-MS: m/z 440 [M+H]$^+$.

Step 2

Following the general method as outlined in Example 70, starting from 6-fluoro-1-(phenylsulfonyl)-3-(1-((tetrahydro-2H-pyran-4-yl)methyl)-1H-pyrazol-4-yl)-1H-indole (Step 1; 398 mg; 0.90 mmol), 102 mg (38%) of the title compound was obtained as a white solid after purification by preparative HPLC.

LC-MS: m/z 300.1 [M+H]$^+$.

$^1$H NMR (400 MHz, DMSO-d$_6$) δ [ppm]: 11.16 (s, 1H), 8.09 (s, 1H), 7.78 (s, 1H), 7.75 (dd, J=8.7, 5.4 Hz, 1H), 7.54 (d, J=2.3 Hz, 1H), 7.16 (dd, J=10.0, 2.2 Hz, 1H), 6.91 (td, J=9.3, 2.3 Hz, 1H), 4.03 (d, J=7.1 Hz, 2H), 3.84 (dd, J=11.2, 2.8 Hz, 2H), 3.26 (td, J=11.6, 1.8 Hz, 2H), 2.17-2.03 (m, 1H), 1.44 (d, J=11.3 Hz, 2H), 1.27 (qd, J=12.2, 4.4 Hz, 2H). m.p. 138.9-139.6° C.

Example 59

4-(4-(6-fluoro-1H-indol-3-yl)-1H-pyrazol-1-yl)methyl)tetrahydro-2H-pyran-4-ol

Step 1: 4-((4-(6-fluoro-1-(phenylsulfonyl)-1H-indol-3-yl)-1H-pyrazol-1-yl)methyl)tetrahydro-2H-pyran-4-ol The mixture of $K_2CO_3$ (221 mg; 1.6 mmol) and 1,6-dioxaspiro[2.5]octane (106 mg; 0.93 mmol) and 6-fluoro-1-(phenylsulfonyl)-3-(1H-pyrazol-4-yl)-1H-indole (Intermediate 5; 300 mg; 0.88 mmol) in DMF(2 ml) was stirred at 80° C. for 12 hours. The mixture was poured into ice-water (20 mL) and extracted with EtOAc (30 mL×3). The combined organic layers were dried over anhydrous $Na_2SO_4$, filtered, concentrated, and purified by a silica gel chromatography (solvent ration) to afford 300 mg (75%) of the title compound as a yellow solid.

LC-MS: m/z 456.1 [M+H]$^+$.

Step 2

Following the general method as outlined in Example 70, starting from 4-((4-(6-fluoro-1-(phenylsulfonyl)-1H-indol-3-yl)-1H-pyrazol-1-yl)methyl)tetrahydro-2H-pyran-4-ol (Step 1; 300 mg; 0.66 mmol), 50 mg (24%) of the title compound was obtained as a white solid after purification by preparative HPLC.

$^1$H NMR (400 MHz, MeOH-d$_4$) δ [ppm]: 7.97 (s, 1H), 7.81 (s, 1H), 7.72 (dd, J=8.7, 5.3 Hz, 1H), 7.42 (s, 1H), 7.11 (dd, J=9.9, 2.3 Hz, 1H), 6.94-6.85 (m, 1H), 4.21 (s, 2H), 3.87-3.69 (m, 4H), 1.87-1.70 (m, 2H), 1.47 (dd, J=13.9, 1.8 Hz, 2H).

$^{19}$F NMR (377 MHz, MeOH-d$_4$) δ [ppm]: −124.51 (s, 1H). m.p. 213.5-214.5° C.

Example 60

4-(4-(6-fluoro-1H-indol-3-yl)-1H-pyrazol-1-yl)methyl)tetrahydro-2H-thiopyran 1,1-dioxide Following the general method as outlined in Intermediate 20, starting from 6-fluoro-1-(phenylsulfonyl)-3-(1H-pyrazol-4-yl)-1H-indole (Intermediate 5; 92 mg; 0.27 mmol) and (1,1-dioxidotetrahydro-2H-thiopyran-4-yl)methyl methanesulfonate (100 mg; 0.41 mmol), 30 mg (32%) of the title compound was obtained as a yellow solid after purification by preparative TLC (DCM/MeOH=20/1).

LC-MS: m/z 348.1[M+H]$^+$.

$^1$H NMR (400 MHz, MeOH-d$_4$) δ [ppm]: 8.00 (s, 1H), 7.83 (s, 1H), 7.72 (dd, J=8.8, 5.3 Hz, 1H), 7.42 (s, 1H), 7.11 (dd, J=10.0, 2.3 Hz, 1H), 6.94-6.83 (m, 1H), 4.19 (d, J=7.2 Hz, 2H), 3.23-3.03 (m, 4H), 2.36-2.26 (m, 2H), 2.11-1.99 (m, 2H), 1.95-1.80 (m, 2H).

$^{19}$F NMR (377 MHz, MeOH-d$_4$) δ [ppm]: −124.28. m.p. 193.1-194.1° C.

Example 61 cis-3-(4-(6-fluoro-1H-indol-3-yl)-1H-pyrazol-1-yl)cyclobutanecarboxamide

Step 1: cis-3-(4-(6-fluoro-1-(phenylsulfonyl)-1H-indol-3-yl)-1H-pyrazol-1-yl)cyclobutanecarboxamide A mixture of cis-3-(4-(6-fluoro-1-(phenylsulfonyl)-1H-indol-3-yl)-1H-pyrazol-1-yl)cyclobutanecarboxylic acid (Intermediate 36; 100 mg; 0.23 mmol), Et$_3$N (0.13 mL; 0.93 mmol), NH$_4$Cl (24 mg; 0.45 mmol) and HATU (173 mg; 0.45 mmol) in THF (5 mL) was stirred for 1 hour. The reaction mixture was added water (20 mL) and extracted with EtOAc (50 mL×2). The combined organic layers were dried over anhydrous Na$_2$SO$_4$, filtered, and concentrated to afford 98 mg (98%) of the title compound as a white solid, which was used directly without further purification.

LC-MS: m/z 439 [M+H]$^+$.

Step 2

Following the general method as outlined in Example 70, starting from cis-3-(4-(6-fluoro-1-(phenylsulfonyl)-1H-indol-3-yl)-1H-pyrazol-1-yl)cyclobutanecarboxamide (Step 1; 195 mg; 0.44 mmol), 14.9 mg (11%) of the title compound was obtained as a white solid after purification by preparative TLC (DCM/MeOH=10/1).

$^1$H NMR (400 MHz, DMSO-d$_6$) δ [ppm]: 11.18 (s, 1H), 8.13 (s, 1H), 7.82 (s, 1H), 7.77 (dd, J=8.8, 5.4 Hz, 1H), 7.56 (d, J=2.4 Hz, 1H), 7.33 (s, 1H), 7.16 (dd, J=10.1, 2.3 Hz, 1H), 6.95-6.83 (m, 2H), 4.77 (dd, J=12.5, 4.6 Hz, 1H), 2.83-2.72 (m, 1H), 2.69-2.54 (m, 4H). m.p. 225.7-226.3° C.

Example 62 trans-3-(4-(6-fluoro-1H-indol-3-yl)-1H-pyrazol-1-yl)cyclobutanecarboxamide

Step 1: trans-3-(4-(6-fluoro-1-(phenylsulfonyl)-1H-indol-3-yl)-1H-pyrazol-1-yl)cyclobutanecarboxamide Following the general method as outlined in Example 61, starting from trans-3-(4-(6-fluoro-1-(phenylsulfonyl)-1H-indol-3-yl)-1H-pyrazol-1-yl)cyclobutanecarboxylic acid (Intermediate 34; 63 mg; 0.14 mmol), 63 mg (100%) of the title compound was obtained as a white solid, which was used directly without further purification.

LC-MS: m/z 439 [M+H]$^+$.

Step 2

Following the general method as outlined in Example 70, starting from trans-3-(4-(6-fluoro-1-(phenylsulfonyl)-1H-indol-3-yl)-1H-pyrazol-1-yl)cyclobutanecarboxamide (Step 1; 63 mg; 0.14 mmol), 6.2 mg (15%) of the title compound was obtained as a white solid after purification by preparative TLC (DCM/MeOH=9/1).

$^1$H NMR (400 MHz, MeOH-d$_4$) δ [ppm]: 7.94 (d, J=5.7 Hz, 1H), 7.77 (d, J=3.9 Hz, 1H), 7.64 (dd, J=8.7, 5.2 Hz, 1H), 7.33 (s, 1H), 7.02 (dd, J=9.8, 2.2 Hz, 1H), 6.81 (ddd, J=9.6, 8.8, 2.3 Hz, 1H), 5.14-4.99 (m, 1H), 3.16 (qd, J=8.3, 3.9 Hz, 1H), 2.81 (tdd, J=9.8, 7.9, 2.3 Hz, 2H), 2.74-2.61 (m, 2H). m.p. 198.4-199.2° C.

Example 63 cis-3-(4-(6-fluoro-1H-indol-3-yl)-1H-pyrazol-1-yl)-N-methylcyclobutanecarboxamide

Step 1: cis-3-(4-(6-fluoro-1-(phenylsulfonyl)-1H-indol-3-yl)-1H-pyrazol-1-yl)-N-methylcyclobutanecarboxamide Following the general method as outlined in Example 61, starting from cis-3-(4-(6-fluoro-1-(phenylsulfonyl)-1H-indol-3-yl)-1H-pyrazol-1-yl)cyclobutanecarboxylic acid (Intermediate 36; 100 mg; 0.23 mmol), and MeNH$_2$ (0.23 mL; 0.46 mmol; 2.0 M in THF), 100 mg (96%) of the title compound was obtained as a yellow oil, which was used directly without further purification.

LC-MS: m/z 453 [M+H]$^+$.

Step 2

Following the general method as outlined in Example 70, starting from cis-3-(4-(6-fluoro-1-(phenylsulfonyl)-1H-indol-3-yl)-1H-pyrazol-1-yl)-N-methylcyclobutanecarboxamide (Step 1; 200 mg; 0.44 mmol), 32.6 mg (24%) of the title compound was obtained as a white solid after purification by preparative TLC (DCM/MeOH=10/1).

$^1$H NMR (400 MHz, DMSO-d$_6$) δ [ppm]: 11.18 (s, 1H), 8.12 (s, 1H), 7.89-7.70 (m, 3H), 7.56 (d, J=2.4 Hz, 1H), 7.16 (dd, J=10.0, 2.3 Hz, 1H), 6.99-6.82 (m, 1H), 4.84-4.71 (m, 1H), 2.77 (dd, J=17.7, 8.8 Hz, 1H), 2.66-2.59 (m, 8H). m.p. 173.7-174.6° C.

Example 64 trans-3-(4-(6-fluoro-1H-indol-3-yl)-1H-pyrazol-1-yl)-N-methylcyclobutanecarboxamide Step 1: trans-3-(4-(6-fluoro-1-(phenylsulfonyl)-1H-indol-3-yl)-1H-pyrazol-1-yl)-N-methylcyclobutanecarboxamide Following the general method as outlined in Example 67, starting from trans-3-(4-(6-fluoro-1-(phenylsulfonyl)-1H-indol-3-yl)-1H-pyrazol-1-yl)cyclobutanecarboxylic acid (Intermediate 34; 50 mg; 0.11 mmol), 52 mg (100%) of the title compound was obtained as a yellow oil, which was used directly without further purification.

LC-MS: m/z 453 [M+H]$^+$.

Step 2

Following the general method as outlined in Example 70, starting from trans-3-(4-(6-fluoro-1-(phenylsulfonyl)-1H-indol-3-yl)-1H-pyrazol-1-yl)-N-methylcyclobutanecarboxamide (Step 1; 52 mg; 0.11 mmol), 20 mg (56%) of the title compound was obtained as a yellow solid after purification by preparative TLC (DCM/MeOH=9/1).

$^1$H NMR (400 MHz, DMSO-d$_6$) δ [ppm]: 11.17 (s, 1H), 8.20 (s, 1H), 7.80 (dt, J=8.8, 5.2 Hz, 3H), 7.53 (d, J=2.4 Hz, 1H), 7.16 (dd, J=10.0, 2.3 Hz, 1H), 7.00-6.82 (m, 1H), 5.12-4.99 (m, 1H), 3.03 (dd, J=9.1, 4.8 Hz, 1H), 2.77-2.66 (m, 2H), 2.63 (d, J=4.6 Hz, 3H), 2.61-2.54 (m, 2H). m.p. 177.8-178.4° C.

Example 65 cis-3-(4-(6-fluoro-1H-indol-3-yl)-1H-pyrazol-1-yl)cyclobutanecarboxylic acid

The title compound was obtained (10.4 mg; 8%) as a yellow solid after purification by preparative TLC (DCM/MeOH=10/1) in step 2 of Example 40.

$^1$H NMR (400 MHz, DMSO-d$_6$) δ [ppm]: 12.50-12.20 (m, 1H), 11.24 (d, J=11.9 Hz, 1H), 8.16 (s, 1H), 7.84 (s, 1H), 7.78 (dd, J=8.7, 5.4 Hz, 1H), 7.56 (d, J=2.4 Hz, 1H), 7.16 (dd, J=10.0, 2.3 Hz, 1H), 6.91 (ddd, J=9.7, 8.8, 2.4 Hz, 1H), 4.88-4.73 (m, 1H), 3.01-2.84 (m, 1H), 2.75-2.58 (m, 4H). m.p. 220.4-221.7° C.

Example 66 trans-3-(4-(6-fluoro-1H-indol-3-yl)-1H-pyrazol-1-yl)cyclobutanecarboxylic acid

The title compound was obtained (2.2 mg; 5%) as a yellow solid after purification by preparative TLC (DCM/MeOH=9/1) in step 2 of example 44.

$^1$H NMR (400 MHz, MeOH-d$_4$) δ [ppm]: 7.90 (s, 1H), 7.73 (s, 1H), 7.60 (dd, J=8.8, 5.3 Hz, 1H), 7.29 (s, 1H), 6.98 (dd, J=9.9, 2.4 Hz, 1H), 6.83-6.70 (m, 1H), 5.11-4.95 (m, 1H), 3.17-3.05 (m, 1H), 2.81 (ddd, J=12.5, 10.1, 8.0 Hz, 2H), 2.75-2.62 (m, 2H).

Example 69 trans-4-(4-(6-fluoro-1H-indol-3-yl)-1H-pyrazol-1-yl)cyclohexanol

Following the general method as outlined in Example 70, starting from trans-4-(4-(6-fluoro-1-(phenylsulfonyl)-1H-indol-3-yl)-1H-pyrazol-1-yl)cyclohexanol (Intermediate 49; 32 mg; 0.073 mmol), 15 mg (69%) of the title compound was obtained as a white solid after purification by preparative TLC (DCM/MeOH=20/1).

$^1$H NMR (400 MHz, MeOH-d$_4$) δ [ppm]: 7.96 (s, 1H), 7.78 (s, 1H), 7.71 (dd, J=8.7, 5.3 Hz, 1H), 7.40 (s, 1H), 7.10 (dd, J=9.9, 2.3 Hz, 1H), 6.98-6.78 (m, 1H), 4.33-4.19 (m, 1H), 3.71 (ddd, J=11.0, 6.7, 4.3 Hz, 1H), 2.26-2.07 (m, 4H), 1.99 (dt, J=12.1, 6.7 Hz, 2H), 1.63-1.42 (m, 2H). m.p. 189.7-190.5° C.

Example 70

6-fluoro-3-(1H-pyrazol-4-yl)-1H-indole

To a solution of 6-fluoro-1-(phenylsulfonyl)-3-(1H-pyrazol-4-yl)-1H-indole (Intermediate 5; 183 mg; 0.54 mmol) in MeOH (20 mL) was added a solution of NaOH (142 mg; 3.55 mmol) in water (1 mL). The reaction mixture was stirred at 85° C. for 4 h, concentrated, diluted with H$_2$O (5 mL), and extracted with Et$_2$O (10 mL×3). The combined organic layers were washed with water (10 mL×2), brine (10 mL), dried over anhydrous Na$_2$SO$_4$, filtered, and concentrated. The crude product was purified by preparative HPLC. 39 mg (36%) of the title compound was obtained as a white solid.

$^1$H NMR (400 MHz, DMSO-d$_6$) δ [ppm]: 12.81 (s, 1H), 11.15 (s, 1H), 8.07 (s, 1H), 7.83-7.74 (m, 2H), 7.54-7.53 (m, 1H), 7.17-7.14 (m, 1H), 6.92-6.85 (m, 1H). m.p. 152.3-156.5° C.

Example 71

5,6-difluoro-3-(1H-pyrazol-4-yl)-1H-indole

Following the general method as outlined in Example 70, starting from 5,6-difluoro-1-(phenylsulfonyl)-3-(1H-pyrazol-4-yl)-1H-indole hydrochloride (Intermediate 30; 150 mg; 0.39 mmol), 10 mg (12%) of the title compound was obtained as a white solid after purification by reverse phase flash chromatography.

¹H NMR (400 MHz, DMSO-d₆) δ [ppm]: 12.88 (s, 1H), 11.31 (s, 1H), 8.02 (s, 2H), 7.76 (dd, J=10.8, 8.4 Hz, 1H), 7.64 (s, 1H), 7.40 (dd, J=10.9, 7.2 Hz, 1H). m.p. 163.1-165.5° C.

Example 72

3-(1H-pyrazol-4-yl)-6-(trifluoromethyl)-1H-indole

Following the general method as outlined in Example 70, starting from 1-(phenylsulfonyl)-3-(1H-pyrazol-4-yl)-6-(trifluoromethyl)-1H-indole (Intermediate 42; 200 mg; 0.51 mmol), 65 mg (50%) of the title compound was obtained as a white solid after purification by preparative TLC (DCM/MeOH=9/1).

¹H NMR (400 MHz, DMSO-d₆) δ [ppm]: 13.05-12.74 (m, 1H), 11.57 (s, 1H), 8.14 (s, 1H), 7.99 (d, J=8.3 Hz, 1H), 7.89 (s, 1H), 7.81 (d, J=2.4 Hz, 1H), 7.74 (s, 1H), 7.32 (dd, J=8.4, 1.4 Hz, 1H).

¹⁹F NMR (377 MHz, DMSO) δ: −58.77 (s, 1H). m.p. 185.4-186.6° C.

Example 73

6-fluoro-3-(1-methyl-H-pyrazol-4-yl)-1H-indole

Following the general method as outlined in Example 70, starting from 6-fluoro-3-(1-methyl-1H-pyrazol-4-yl)-1-(phenylsulfonyl)-1H-indole (Intermediate 6; 218 mg; 0.61 mmol), 65 mg (49%) of the title compound was obtained as a white solid after purification by preparative HPLC.

¹H NMR (400 MHz, DMSO-d₆) δ [ppm]: 11.19 (s, 1H), 8.07 (s, 1H), 7.76-7.73 (m, 2H), 7.54-7.53 (m, 1H), 7.18-7.15 (m, 1H), 6.93-6.88 (m, 1H), 3.87 (s, 3H). m.p. 187.7-188.4° C.

Example 74

3-(1,5-dimethyl-1H-pyrazol-4-yl)-6-fluoro-1H-indole and 3-(1,3-dimethyl-1H-pyrazol-4-yl)-6-fluoro-1H-indole Following the general method as outlined in Example 70, starting from 3-(1,5-dimethyl-1H-pyrazol-4-yl)-6-fluoro-1-(phenylsulfonyl)-1H-indole and 3-(1,3-dimethyl-1H-pyrazol-4-yl)-6-fluoro-1-(phenylsulfonyl)-1H-indole (Intermediate 26; 382 mg; 1.03 mmol), 17 mg (7%) of the title compound were obtained as a white solid after purification by preparative HPLC and preparative chiral HPLC (Chiralpak AD-H column, eluting with Hexane/isopropyl alcohol/diethylamine 80/20/0.3, first eluting product).

¹H NMR (400 MHz, MeOH-d₄) δ [ppm]: 7.63 (s, 1H), 7.42 (dd, J=8.7, 5.3 Hz, 1H), 7.14 (s, 1H), 6.98 (dd, J=9.9, 2.3 Hz, 1H), 6.78-6.69 (m, 1H), 3.78 (s, 3H), 2.20 (s, 3H).

Example 75

3-(1,3-dimethyl-1H-pyrazol-4-yl)-6-fluoro-1H-indole

The Title Compound (26 mg; 11%) was obtained as the second-eluting product in the preparative chiral HPLC of Example 74.

¹H NMR (400 MHz, MeOH-d₄) δ [ppm]: 7.57 (s, 1H), 7.48 (dd, J=8.7, 5.3 Hz, 1H), 7.21 (s, 1H), 7.11 (dd, J=9.9, 2.2 Hz, 1H), 6.88-6.82 (m, 1H), 3.88 (s, 3H), 2.36 (s, 3H).

Example 78

6-fluoro-3-(1-(piperidin-4-yl)-1H-pyrazol-4-yl)-1H-indole

To a solution of tert-butyl 4-(4-(6-fluoro-1H-indol-3-yl)-1H-pyrazol-1-yl)piperidine-1-carboxylate (Intermediate 16B; 230 mg; 0.60 mmol) in dioxane (3 mL) was added conc. aqueous HCl (3 mL; 36%). The reaction mixture was stirred for 0.5 hour and concentrated to dryness, neutralized with saturated aqueous NaHCO₃ (50 mL), extracted with EtOAc (50 ml×2). The combined organic layers were dried over anhydrous Na₂SO₄, filtered, concentrated. The residue was purified by preparative TLC (DCM/MeOH=10/1) to afford 70 mg (41%) of the title compound as a yellow solid.

LC-MS: m/z 285.2 [M+H]⁺.

¹H NMR (400 MHz, MeOH-d₄) δ [ppm]: 8.02 (s, 1H), 7.85 (s, 1H), 7.71 (dd, J=8.7, 5.3 Hz, 1H), 7.42 (s, 1H), 7.10 (dd, J=9.8, 2.1 Hz, 1H), 6.88 (td, J=9.4, 2.3 Hz, 1H), 4.59 (ddd, J=15.2, 10.3, 4.7 Hz, 1H), 3.58 (d, J=13.1 Hz, 2H), 3.23 (td, J=12.7, 3.9 Hz, 2H), 2.46-2.17 (m, 4H). m.p. 240.1-241.8° C.

Example 79

2-(4-(4-(6-fluoro-1H-indol-3-yl)-1H-pyrazol-1-yl)piperidin-1-yl)ethanol

Step 1: 2-(4-(4-(6-fluoro-1-(phenylsulfonyl)-1H-indol-3-yl)-1H-pyrazol-1-yl)piperidin-1-yl)ethanol To a mixture of 6-fluoro-1-(phenylsulfonyl)-3-(1-(piperidin-4-yl)-1H-pyrazol-4-yl)-1H-indole hydrochloride (Intermediate 17; 210 mg; 0.46 mmol), K₂CO₃ (189 mg; 1.37 mmol) and KI (3 mg; 0.018 mmol) in DMF (5 mL) was added 2-bromoethanol (115 mg; 0.92 mmol) under nitrogen. The reaction mixture was stirred at 100° C. for 15 hours, concentrated, and purified by preparative TLC (DCM/MeOH=10/1) to afford 148 mg (69%) of the title compound as a white solid.

LC-MS: m/z 469.1 [M+H]⁺.

¹H NMR (400 MHz, DMSO-d₆) δ [ppm]: 8.40 (s, 1H), 8.11 (s, 1H), 8.07-7.99 (m, 3H), 7.94 (dd, J=8.8, 5.3 Hz, 1H), 7.76 (dd, J=9.9, 2.1 Hz, 1H), 7.71 (t, J=7.6 Hz, 1H), 7.61 (t, J=7.7 Hz, 2H), 7.22 (td, J=9.1, 2.2 Hz, 1H), 4.45-4.27 (m, 1H), 3.81-3.58 (m, 2H), 3.05-2.66 (m, 6H), 2.09-2.63 (m, 4H).

Step 2

Following the general method as outlined in Example 70, starting from 2-(4-(4-(6-fluoro-1-(phenylsulfonyl)-1H-indol-3-yl)-1H-pyrazol-1-yl)piperidin-1-yl)ethanol (Step 1; 148 mg; 0.32 mmol), 36 mg (35%) of the title compound was obtained as a yellow solid after purification by preparative HPLC.

LC-MS: m/z 329.2 [M+H]⁺.

¹H NMR (400 MHz, DMSO-d₆) δ [ppm]: 11.17 (s, 1H), 8.12 (s, 1H), 7.83-7.71 (m, 2H), 7.53 (d, J=2.0 Hz, 1H), 7.16 (dd, J=10.1, 2.2 Hz, 1H), 6.90 (td, J=9.4, 2.2 Hz, 1H), 4.13 (dd, J=14.9, 7.7 Hz, 1H), 3.53 (t, J=6.3 Hz, 2H), 2.99 (d, J=11.4 Hz, 2H), 2.44 (t, J=6.3 Hz, 2H), 2.20-2.10 (m, 2H), 1.99-2.01 (m, 4H).

Example 80

4-(4-(4-(6-fluoro-1H-indol-3-yl)-1H-pyrazol-1-yl)piperidin-1-yl)-4-oxobutanoic acid Step 1: methyl 4-(4-(4-(6-fluoro-1-(phenylsulfonyl)-1H-indol-3-yl)-1H-pyrazol-1-yl)piperidin-1-yl)-4-oxobutanoate Following the general method as outlined in Example 83, starting from 6-fluoro-1-(phenylsulfonyl)-3-(1-(piperidin-4- yl)-1H-pyrazol-4-yl)-1H-indole hydrochloride (Intermediate 17; 400 mg; 0.86 mmol) and succinic acid monomethyl ester (249 mg; 1.88 mmol) in DMF (10 mL), 506 mg of the title compound was obtained as a yellow oil after purification by a silica gel chromatography (EA).

LC-MS: m/z 539.1 [M+H]$^+$.

Step 2

Following the general method as outlined in Example 70, starting from 4-(4-(4-(6-fluoro-1-(phenylsulfonyl)-1H-indol-3-yl)-1H-pyrazol-1-yl)piperidin-1-yl)-4-oxobutanoate (Step 1; 506 mg), 82.2 mg (22.8%) of the title compound was obtained as a white solid after purification by preparative HPLC.

LC-MS: m/z 385.1 [M+H]$^+$.

$^1$H NMR (400 MHz, MeOH-d$_4$) δ [ppm]: 8.02 (s, 1H), 7.81 (s, 1H), 7.72 (dd, J=8.7, 5.3 Hz, 1H), 7.41 (s, 1H), 7.10 (dd, J=9.8, 2.3 Hz, 1H), 6.93-6.84 (m, 1H), 4.69 (d, J=14.1 Hz, 1H), 4.52 (td, J=11.5, 5.9 Hz, 1H), 4.21 (d, J=15.6 Hz, 1H), 2.90 (d, J=10.6 Hz, 2H), 2.76 (dd, J=15.2, 6.9 Hz, 2H), 2.63 (t, J=6.5 Hz, 2H), 2.21 (d, J=20.6 Hz, 2H), 2.15-1.96 (m, 2H). m.p. 226-228° C.

Example 81

1-(4-(4-(6-fluoro-1H-indol-3-yl)-1H-pyrazol-1-yl)piperidin-1-yl)-3-methoxypropan-1-one Step 1: 1-(4-(4-(6-fluoro-1-(phenylsulfonyl)-1H-indol-3-yl)-1H-pyrazol-1-yl)piperidin-1-yl)-3-methoxypropan-1-one Following the general method as outlined in Example 83, starting from 6-fluoro-1-(phenylsulfonyl)-3-(1-(piperidin-4-ylmethyl)-1H-pyrazol-4-yl)-1H-indole (Intermediate 21; 382 mg; 0.87 mmol) and 3-methoxypropanoic acid (180 mg; 1.73 mmol), 620 mg of the title compound was obtained as a yellow oil after purification by a silica gel chromatography (EtOAc).

LC-MS: m/z 511 [M+H]$^+$.

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)-3-methoxypropan-1-one (Step 1; 440 mg), 30 mg (13%) of the title compound was obtained as a white solid after purification by preparative HPLC.

$^1$H NMR (400 MHz, DMSO-d$_6$) δ [ppm]: 11.16 (s, 1H), 8.15 (s, 1H), 7.82-7.76 (m, 2H), 7.53 (d, J=2.3 Hz, 1H), 7.16 (dd, J=10.0, 2.3 Hz, 1H), 6.90 (td, J=9.6, 2.4 Hz, 1H), 4.47 (dd, J=23.4, 12.3 Hz, 2H), 4.02 (d, J=14.4 Hz, 1H), 3.58 (t, J=6.6 Hz, 2H), 3.24 (s, 3H), 3.18 (d, J=12.4 Hz, 1H), 2.75 (t, J=12.7 Hz, 1H), 2.63 (t, J=6.6 Hz, 2H), 2.07 (t, J=13.4 Hz, 2H), 1.87 (ddd, J=46.6, 12.2, 4.7 Hz, 2H).

Example 82

1-(4-(4-(6-fluoro-1H-indol-3-yl)-1H-pyrazol-1-yl)piperidin-1-yl)propan-1-one

Step 1: 1-(4-(4-(6-fluoro-1-(phenylsulfonyl)-1H-indol-3-yl)-1H-pyrazol-1-yl)piperidin-1-yl)propan-1-one Following the general method as outlined in Example 89, starting from 6-fluoro-1-(phenylsulfonyl)-3-(1-(piperidin-4-yl)-1H-pyrazol-4-yl)-1H-indole hydrochloride (Intermediate 17; 370 mg; 0.80 mmol) and propionyl chloride (179 mg; 1.93 mmol), 310 mg (80%) of the title compound was obtained as a yellow oil, which was used directly without further purification.

LC-MS: m/z 481 [M+H]$^+$.

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)propan-1-one (Step 1; 310 mg; 0.65 mmol), 50 mg (23%) of the title compound was obtained as a white solid after purification by preparative HPLC.

$^1$H NMR (400 MHz, DMSO-d$_6$) δ [ppm]: 11.16 (s, 1H), 8.15 (s, 1H), 7.79 (q, J=5.6 Hz, 2H), 7.53 (d, J=2.4 Hz, 1H), 7.16 (dd, J=10.1, 2.3 Hz, 1H), 6.93-6.86 (m, 1H), 4.56-4.39 (m, 2H), 3.98 (d, J=14.1 Hz, 1H), 3.19 (t, J=12.0 Hz, 1H), 2.74 (t, J=11.5 Hz, 1H), 2.38 (q, J=7.4 Hz, 2H), 2.07 (t, J=13.6 Hz, 2H), 1.99-1.75 (m, 2H), 1.02 (t, J=7.4 Hz, 3H). m.p. 200-202° C.

Example 83

2-(dimethylamino)-1-(4-(4-(6-fluoro-1H-indol-3-yl)-1H-pyrazol-1-yl)piperidin-1-yl)ethanone Step 1: 2-(dimethylamino)-1-(4-(4-(6-fluoro-1-(phenylsulfonyl)-1H-indol-3-yl)-1H-pyrazol-1-yl)piperidin-1-yl)ethanone To a solution of (dimethylamino)acetic acid (165 mg; 1.60 mmol), HATU (608 mg; 1.60 mmol), and DIPEA (619 mg; 4.80 mmol) in THF (25 mL) was added 6-fluoro-1-(phenylsulfonyl)-3-(1-(piperidin-4-yl)-1H-pyrazol-4-yl)-1H-indole hydrochloride (Intermediate 17; 368 mg; 0.80 mmol) under nitrogen. The reaction mixture was stirred overnight, concentrated, dealed with saturated aqueous NaHCO$_3$ (50 mL), extracted with EtOAc (50 ml×2). The combined organic layers were dried over anhydrous Na$_2$SO$_4$, filtered, concentrated and purified by a silica gel chromatography (DCM/MeOH=20/1) to afford 400 mg (100%) of the title compound as a yellow oil.

LC-MS: m/z 510.1 [M+H]$^+$.

Step 2

Following the general method as outlined in Example 70, starting from 2-(dimethylamino)-1-(4-(4-(6-fluoro-1-(phenylsulfonyl)-1H-indol-3-yl)-1H-pyrazol-1-yl)piperidin-1-yl)ethanone (Step 1; 400 mg; 0.80 mmol), 80 mg (27%) of the title compound was obtained as a white solid after purification by preparative HPLC.

LC-MS: m/z 370.2 [M+H]$^+$.

$^1$H NMR (400 MHz, MeOH-d$_4$) δ [ppm]: 7.99 (d, J=4.4 Hz, 1H), 7.81 (s, 1H), 7.71 (dd, J=8.8, 5.3 Hz, 1H), 7.40 (s, 1H), 7.15-7.05 (m, 1H), 6.96-6.79 (m, 1H), 4.69 (dd, J=15.4, 5.1 Hz, 1H), 4.51 (tt, J=11.2, 4.1 Hz, 1H), 4.25 (d, J=13.2 Hz, 1H), 3.25-3.37 (m, 1H), 2.89 (m, 1H), 2.19-2.16 (m, 2H), 2.16-1.89 (m, 2H). m.p. 193.7-196.1° C.

Example 84

1-(4-(4-(6-fluoro-1H-indol-3-yl)-1H-pyrazol-1-yl)piperidin-1-yl)-2-hydroxyethanone

Step 1: 2-(4-(4-(6-fluoro-1-(phenylsulfonyl)-1H-indol-3-yl)-1H-pyrazol-1-yl)piperidin-1-yl)-2-oxoethyl acetate Following the general method as outlined in Example 89, starting from 6-fluoro-1-(phenylsulfonyl)-3-(1-(piperidin-4-yl)-1H-pyrazol-4-yl)-1H-indole hydrochloride (Intermediate 17; 368 mg; 0.80 mmol) and 2-chloro-2-oxoethyl acetate (165 mg; 1.21 mmol), 421 mg (100%) of the title compound was obtained as a yellow solid, which was used directly without further purification.
LC-MS: m/z 525.0 [M+H]$^+$.
$^1$H NMR (400 MHz, DMSO-$d_6$) δ [ppm]: 8.38 (s, 1H), 8.13-7.98 (m, 4H), 7.93 (dd, J=8.8, 5.3 Hz, 1H), 7.76 (dd, J=9.8, 2.0 Hz, 1H), 7.70 (t, J=7.4 Hz, 1H), 7.60 (t, J=7.7 Hz, 2H), 7.22 (td, J=9.1, 2.1 Hz, 1H), 4.83 (s, 2H), 4.48 (ddd, J=11.6, 9.9, 4.0 Hz, 1H), 4.40 (dd, J=13.4, 1.1 Hz, 1H), 3.90-3.77 (m, 1H), 3.21 (dd, J=12.9, 12.4 Hz, 1H), 2.89-2.75 (m, 1H), 2.09 (s, 3H), 2.08-1.72 (m, 4H).

Step 2

Following the general method as outlined in Example 70, starting from 2-(4-(4-(6-fluoro-1-(phenylsulfonyl)-1H-indol-3-yl)-1H-pyrazol-1-yl)piperidin-1-yl)-2-oxoethyl acetate (Step 1; 421 mg; 0.80 mmol), 26 mg (9%) of the title compound was obtained as a white solid after purification by preparative HPLC.
LC-MS: m/z 343.1 [M+H]$^+$.
$^1$H NMR (400 MHz, DMSO-$d_6$) δ [ppm]: 11.18 (s, 1H), 8.15 (s, 1H), 7.78 (d, J=9.0 Hz, 2H), 7.54 (s, 1H), 7.16 (d, J=10.0 Hz, 1H), 6.90 (t, J=9.0 Hz, 1H), 4.56 (m, 1H), 4.51-4.41 (m, 2H), 4.13 (s, 2H), 3.80-3.84 (m, 1H), 3.21-3.07 (m, 1H), 2.88-2.74 (m, 1H), 2.14-1.71 (m, 5H). m.p. 99.9-102.1° C.

Example 85

1-(4-(4-(6-fluoro-1H-indol-3-yl)-1H-pyrazol-1-yl)piperidin-1-yl)-2-methoxyethanone

Step 1: 1-(4-(4-(6-fluoro-1-(phenylsulfonyl)-1H-indol-3-yl)-1H-pyrazol-1-yl)piperidin-1-yl)-2-methoxyethanone Following the general method as outlined in Example 83, starting from 6-fluoro-1-(phenylsulfonyl)-3-(1-(piperidin-4-ylmethyl)-1H-pyrazol-4-yl)-1H-indole (Intermediate 21; 188 mg; 0.43 mmol) and 2-methoxyacetic acid (41 mg; 0.46 mmol), 260 mg of the title compound was obtained as a yellow oil after purification by a silica gel chromatography (EtOAc).
LC-MS: m/z 497 [M+H]$^+$.

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)-2-methoxyethanone (Step 1; 260 mg), 10 mg (7%) of the title compound was obtained as a white solid after purification by preparative HPLC.
$^1$H NMR (400 MHz, DMSO-$d_6$) δ [ppm]: 11.18 (s, 1H), 8.15 (s, 1H), 7.79 (q, J=5.3 Hz, 2H), 7.54 (d, J=1.9 Hz, 1H), 7.16 (dd, J=10.1, 2.3 Hz, 1H), 6.90 (td, J=9.7, 2.3 Hz, 1H), 4.46 (t, J=11.3 Hz, 2H), 4.20-4.08 (m, 2H), 3.90 (d, J=12.9 Hz, 1H), 3.31 (s, 3H), 3.21-3.13 (m, 1H), 2.79 (t, J=12.0 Hz, 1H), 2.08 (m, 2H), 1.91 (m, 2H).

Example 86

1-(4-(4-(6-fluoro-1H-indol-3-yl)-1H-pyrazol-1-yl)piperidin-1-yl)-2-methylpropan-1-one

Step 1: 1-(4-(4-(6-fluoro-1-(phenylsulfonyl)-1H-indol-3-yl)-1H-pyrazol-1-yl)piperidin-1-yl)-2-methylpropan-1-one Following the general method as outlined in Example 83, starting from 6-fluoro-1-(phenylsulfonyl)-3-(1-(piperidin-4-yl)-1H-pyrazol-4-yl)-1H-indole hydrochloride (Intermediate 17; 271 mg; 0.59 mmol) and isobutyric acid (104 mg; 1.18 mmol) in DMF (15 mL), 277 mg (90%) of the title compound was obtained as a yellow oil after purification by a silica gel chromatography (DCM/MeOH=20/1).
LC-MS: m/z 495.1 [M+H]$^+$.

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)-2-methylpropan-1-one (Step 1; 277 mg; 0.56 mmol), 31 mg (16%) of the title compound was obtained as a white solid after purification by preparative HPLC.
LC-MS: m/z 355.1 [M+H]$^+$.
$^1$H NMR (400 MHz, DMSO-$d_6$) δ [ppm]: 11.17 (s, 1H), 8.16 (s, 1H), 7.87-7.70 (m, 2H), 7.54 (d, J=2.4 Hz, 1H), 7.16 (dd, J=10.1, 2.3 Hz, 1H), 6.90 (td, J=9.6, 2.4 Hz, 1H), 4.60-4.35 (m, 2H), 4.14-3.92 (m, 1H), 3.22 (dd, J=13.3, 12.7 Hz, 1H), 2.93 (dt, J=13.5, 6.7 Hz, 1H), 2.69-2.76 (dd, J=20.8, 8.3 Hz, 1H), 2.08-2.15 (m, 2H), 1.98-1.67 (m, 2H), 1.03 (dd, J=9.4, 7.3 Hz, 6H). m.p. 210.2-211° C.

Example 87

1-(4-(4-(6-fluoro-1H-indol-3-yl)-1H-pyrazol-1-yl)piperidin-1-yl)-2,2-dimethylpropan-1-one

Step 1: 1-(4-(4-(6-fluoro-1-(phenylsulfonyl)-1H-indol-3-yl)-1H-pyrazol-1-yl)piperidin-1-yl)-2,2-dimethylpropan-1-one Following the general method as outlined in Example 89, starting from 6-fluoro-1-(phenylsulfonyl)-3-(1-(piperidin-4-yl)-1H-pyrazol-4-yl)-1H-indole hydrochloride (Intermediate 17; 200 mg; 0.47 mmol) and pivaloyl chloride (0.12 mL; 0.98 mmol), 250 mg (>100%) of the title compound was obtained as a yellow solid, which was used directly without further purification.
LC-MS: m/z 509 [M+H]$^+$.

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)-2,2-dimethylpropan-1-one (Step 1; 250 mg), 99 mg (54%) of the title compound was obtained as a white solid after purification by preparative HPLC.

LC-MS: m/z 369.1 [M+H]+.

$^1$H NMR (400 MHz, DMSO-d$_6$) δ [ppm]: 11.16 (s, 1H), 8.17 (s, 1H), 7.82-7.77 (m, 2H), 7.54 (d, J=2.4 Hz, 1H), 7.16 (dd, J=10.1, 2.3 Hz, 1H), 7.00-6.80 (m, 1H), 4.52-4.36 (m, 3H), 2.99 (t, J=12.7 Hz, 2H), 2.16-1.97 (m, 2H), 1.95-1.75 (m, 2H), 1.24 (s, 9H).

19F NMR (377 MHz, DMSO-d$_6$) δ [ppm]: −122.09 (s, 1H). m.p. 231-232° C.

Example 88 cyclopropyl(4-(4-(6-fluoro-1H-indol-3-yl)-1H-pyrazol-1-yl)piperidin-1-yl)methanone Step 1: cyclopropyl(4-(4-(6-fluoro-1-(phenylsulfonyl)-1H-indol-3-yl)-1H-pyrazol-1-yl)piperidin-1-yl)methanone Following the general method as outlined in Example 83, starting from 6-fluoro-1-(phenylsulfonyl)-3-(1-(piperidin-4-yl)-1H-pyrazol-4-yl)-1H-indole hydrochloride (Intermediate 17; 300 mg; 0.65 mmol) and cyclopropanecarboxylic acid (122 mg; 1.42 mmol) in DMF (6 mL), 345 mg of the title compound was obtained as a yellow oil, which was used directly without further purification.

LC-MS: m/z 493.1 [M+H]+.

Step 2

Following the general method as outlined in Example 70, starting from cyclopropyl(4-(4-(6-fluoro-1-(phenylsulfonyl)-1H-indol-3-yl)-1H-pyrazol-1-yl)piperidin-1-yl)methanone (Step 1; 345 mg), 118 mg (47.9%) of the title compound was obtained as a white solid after purification by preparative HPLC.

LC-MS: m/z 353.1 [M+H]+.

$^1$H NMR (400 MHz, DMSO-d$_6$) δ [ppm]: 11.16 (s, 1H), 8.17 (s, 1H), 7.86-7.76 (m, 2H), 7.54 (d, J=1.9 Hz, 1H), 7.17 (dd, J=10.1, 2.3 Hz, 1H), 6.95-6.82 (m, 1H), 4.54-4.43 (m, 2H), 4.39 (s, 1H), 3.32 (d, J=24.6 Hz, 1H), 2.78 (s, 1H), 2.12 (s, 1H), 2.09-1.98 (m, 2H), 1.90 (d, J=37.4 Hz, 2H), 0.73 (d, J=7.9 Hz, 4H). m.p. 190.7-191.4° C.

Example 89

1-(4-(4-(6-fluoro-1H-indol-3-yl)-1H-pyrazol-1-yl)piperidin-1-yl)ethanone

Step 1: 1-(4-(4-(6-fluoro-1-(phenylsulfonyl)-1H-indol-3-yl)-1H-pyrazol-1-yl)piperidin-1-yl)ethanone To a solution of 6-fluoro-1-(phenylsulfonyl)-3-(1-(piperidin-4-yl)-1H-pyrazol-4-yl)-1H-indole hydrochloride (Intermediate 17; 290 mg), Et$_3$N (0.23 mL; 1.65 mmol) in DCM (20 mL) was added acetyl chloride (87 mg; 1.1 mmol) dropwise under nitrogen. The reaction mixture was stirred for 1 h and concentrated to afford 256 mg (100%) of the title compound as a white solid, which was used directly without further purification.

LC-MS: m/z 467.1 [M+H]+.

$^1$H NMR (400 MHz, DMSO-d$_6$) δ [ppm]: 8.39 (s, 1H), 8.10 (s, 1H), 8.04 (d, J=7.6 Hz, 2H), 7.99 (s, 1H), 7.94 (dd, J=8.7, 5.4 Hz, 1H), 7.76 (dd, J=9.8, 2.3 Hz, 1H), 7.71 (t, J=7.4 Hz, 1H), 7.61 (t, J=7.8 Hz, 2H), 7.22 (td, J=9.1, 2.3 Hz, 1H), 4.43-4.49 (m, 2H), 3.86-3.95 (m, 1H), 3.27-3.19 (m, 1H), 2.78-2.69 (m, 1H), 2.05 (s, 3H), 2.02-1.77 (m, 4H).

Step 2

Following the general method as outlined in Example 70, starting from 1-(4-(4-(6-fluoro-1-(phenylsulfonyl)-1H-indol-3-yl)-1H-pyrazol-1-yl)piperidin-1-yl)ethanone (Step 1; 250 mg; 0.54 mmol), 80 mg (45%) of the title compound was obtained as a yellow solid after purification by preparative HPLC.

LC-MS: m/z 327.2 [M+H]+.

$^1$H NMR (400 MHz, DMSO-d$_6$) δ [ppm]: 11.16 (s, 1H), 8.16 (s, 1H), 7.85-7.74 (m, 2H), 7.54 (d, J=2.2 Hz, 1H), 7.16 (dd, J=10.0, 2.2 Hz, 1H), 6.90 (td, J=9.7, 2.3 Hz, 1H), 4.55-4.34 (m, 2H), 3.92-3.95 (m, 1H), 3.18-3.25 (m, 1H), 2.70-2.76 (m, 1H), 2.06 (s, 3H), 2.13-1.71 (m, 4H). m.p. 183.2-184.5° C.

Example 90

4-(4-(6-fluoro-1H-indol-3-yl)-1H-pyrazol-1-yl)-N,N-dimethylpiperidine-1-carboxamide The title compound was obtained (15 mg; 8%) as a white solid after purification by reverse phase flash chromatography in step 2 of Example 75.

LC-MS: m/z 356.2 [M+H]+.

$^1$H NMR (400 MHz, DMSO-d$_6$) δ [ppm]: 11.16 (s, 1H), 8.15 (s, 1H), 7.93-7.63 (m, 2H), 7.54 (d, J=2.3 Hz, 1H), 7.16 (dd, J=10.1, 2.3 Hz, 1H), 6.98-6.74 (m, 1H), 4.42-4.27 (m, 1H), 3.67 (d, J=13.2 Hz, 2H), 2.88 (t, J=11.1 Hz, 2H), 2.77 (s, 6H), 2.07-1.85 (m, 4H). m.p. 223.0-224.6° C.

Example 91

6-fluoro-3-(1-(1-methylpiperidin-4-yl)-1H-pyrazol-4-yl)-1H-indole

Step 1: 6-fluoro-3-(1-(1-methylpiperidin-4-yl)-1H-pyrazol-4-yl)-1-(phenylsulfonyl)-1H-indole To a solution of 6-fluoro-1-(phenylsulfonyl)-3-(1-(piperidin-4-yl)-1H-pyrazol-4-yl)-1H-indole hydrochloride (Intermediate 17; 290 mg), Et$_3$N (55 mg; 0.55 mmol)cOH (1 drop), and 37% aqueous HCHO (89 mg; 1.1 mmol) in MeOH (10 mL) was added NaBH(OAc)$_3$ (233 mg; 1.05 mmol). The reaction mixture was stirred for 16 h and concentrated. The residue was dissolved in DCM (20 mL) and washed with saturated NaHCO$_3$ (20 mL). The organic layer was dried over anhydrous Na$_2$SO$_4$, filtered, and concentrated to afford 270 mg (>100%) of the title compound as a white solid.

LC-MS: m/z 439.2 [M+H]+.

$^1$H NMR (400 MHz, CDCl$_3$) δ [ppm]: 7.90 (d, J=7.6 Hz, 2H), 7.70-7.80 (m, 3H), 7.63-7.53 (m, 3H), 7.47 (t, J=7.7 Hz, 2H), 7.05 (td, J=8.9, 2.3 Hz, 1H), 4.25 (dd, J=9.5, 5.2 Hz, 1H), 3.09-3.13 (m, 2H), 2.43 (s, 3H), 2.39-2.21 (m, 6H).

Step 2

Following the general method as outlined in Example 70, starting from 6-fluoro-3-(1-(1-methylpiperidin-4-yl)-1H-pyrazol-4-yl)-1-(phenylsulfonyl)-1H-indole (Step 1; 240 mg), 58 mg (37%) of the title compound was obtained as a white solid after purification by preparative HPLC.

LC-MS: m/z 299.2 [M+H]+.

¹H NMR (400 MHz, DMSO-d₆) δ [ppm]: 11.16 (s, 1H), 8.12 (s, 1H), 7.76-7.80 (m, 2H), 7.53 (d, J=2.3 Hz, 1H), 7.16 (dd, J=10.1, 2.3 Hz, 1H), 6.90 (td, J=9.6, 2.3 Hz, 1H), 4.12 (dd, J=13.3, 7.5 Hz, 1H), 2.85-2.88 (m, 2H), 2.21 (s, 3H), 2.14-1.90 (m, 6H). m.p. 222.8-223.7° C.

Example 107

6-fluoro-3-(1-(pyridazin-3-yl)-1H-pyrazol-4-yl)-1H-indole

Step 1: 6-fluoro-1-(phenylsulfonyl)-3-(1-(pyridazin-3-yl)-1H-pyrazol-4-yl)-1H-indole A mixture of 3-(1-(6-chloropyridazin-3-yl)-1H-pyrazol-4-yl)-6-fluoro-1-(phenylsulfonyl)-1H-indole (Intermediate 44; 180 mg; 0.40 mmol), Pd/C (10 mg) and Et₃N (40 mg; 0.40 mmol) was stirred for 0.5 hour at r.t. under a hydrogen balloon. The reaction mixture was filtered, concentrated, and purified by a silica gel chromatography (petroleum ether/EtOAc=5/1 to 3/1) to afford 100 mg (60%) of the title compound as a white solid.

¹H NMR (400 MHz, DMSO-d₆) δ [ppm]: 9.37 (s, 1H), 9.24 (d, 1H, J=4.4 Hz), 8.55 (s, 1H), 8.42 (s, 1H), 8.27 (d, 1H, J=8.8 Hz), 8.11-8.05 (m, 3H), 7.95-7.92 (m, 1H), 7.80 (d, 1H, J=10.0 Hz), 7.74-7.70 (m, 1H), 7.65-7.61 (m, 1H), 7.25 (t, 1H, J=5.6 Hz).

Step 2

Following the general method as outlined in Example 70, starting from 6-fluoro-1-(phenylsulfonyl)-3-(1-(pyridazin-3-yl)-1H-pyrazol-4-yl)-1H-indole (Step 1; 83 mg; 0.20 mmol), 50 mg (90%) of the title compound was obtained as a white solid after purification by a silica gel chromatography (petroleum ether/EtOAc=4/1 to 2/1).

¹H NMR (400 MHz, DMSO-d₆) δ [ppm]: 11.3 (br, 1H), 9.20 (d, 1H, J=4.8 Hz), 9.12 (s, 1H), 8.40 (s, 1H), 8.26 (d, 1H, J=8.8 Hz), 7.93-7.89 (m, 2H), 7.85 (s, 1H), 7.22 (d, 1H, J=10.0 Hz), 6.96 (t, 1H, J=9.6 Hz).

Example 108

3-(1-(6-chloropyridazin-3-yl)-1H-pyrazol-4-yl)-6-fluoro-1H-indole

A mixture of 3-(1-(6-chloropyridazin-3-yl)-1H-pyrazol-4-yl)-6-fluoro-1-(phenylsulfonyl)-1H-indole (Intermediate 44; 226 mg; 0.50 mmol) in THF (20 mL) was added NaOH (80 mg; 2.0 mmol). The reaction mixture was stirred at 75° C. for 16 hours, concentrated, and purified by preparative HPLC to afford 45 mg (28%) of the title compound as a yellow solid.

¹H NMR (400 MHz, DMSO-d₆) δ [ppm]: 12.3 (br, 1H), 9.08 (s, 1H), 8.44 (s, 1H), 8.31 (d, 1H, J=8.8 Hz), 8.08 (d, 1H, J=9.2 Hz), 7.94-7.90 (m, 1H), 7.87 (s, 1H), 7.22 (d, 1H, J=10.4 Hz), 7.00-6.84 (m, 1H).

Example 109

6-(4-(6-fluoro-1H-indol-3-yl)-1H-pyrazol-1-yl)pyridazin-3-amine

Step 1: N-(2,4-dimethoxybenzyl)-6-(4-(6-fluoro-1-(phenylsulfonyl)-1H-indol-3-yl)-1H-pyrazol-1-yl)pyridazin-3-amine A mixture of 3-(1-(6-chloropyridazin-3-yl)-1H-pyrazol-4-yl)-6-fluoro-1-(phenylsulfonyl)-1H-indole (Intermediate 44; 136 mg; 0.30 mmol) and 2,4-dimethoxybenzylamine (100 mg; 0.60 mmol) in NMP (2 mL) was stirred at 200° C. for 2 hours under a microwave reactor. The reaction mixture was diluted with EtOAc (30 mL), washed water (10 mL), brine (10 mL), dried over anhydrous Na₂SO₄, filtered, concentrated, and purified by a silica gel column chromatography (petroleum ether/EtOAc=4/1 to 2/1) to afford 120 mg (68%) of the title compound as a white solid.

¹H NMR (300 MHz, DMSO-d₆) δ [ppm]: 9.09 (s, 1H), 8.35 (d, 1H, J=13.2 Hz), 8.09 (d, 2H, J=6.9 Hz), 8.02-7.97 (m, 1H), 7.88 (d, 1H, J=9.3 Hz), 7.81 (d, 1H, J=9.9 Hz), 7.70 (d, 1H, J=5.7 Hz), 7.64-7.59 (m, 2H), 7.34-7.30 (m, 1H), 7.24 (d, 1H, J=11.7 Hz), 7.12 (d, 1H, J=9.3 Hz), 4.48 (s, 2H), 3.82 (s, 3H), 3.74 (s, 3H).

Step 2: N-(2,4-dimethoxybenzyl)-6-(4-(6-fluoro-1H-indol-3-yl)-1H-pyrazol-1-yl)pyridazin-3-amine Following the general method as outlined in Example 70, starting from N-(2,4-dimethoxybenzyl)-6-(4-(6-fluoro-1-(phenylsulfonyl)-1H-indol-3-yl)-1H-pyrazol-1-yl)pyridazin-3-amine (145 mg; 0.25 mmol), 80 mg (73%) of the title compound was obtained as a white solid after purification by a silica gel column chromatography (petroleum ether/EtOAc=4/1 to 2/1).

¹H NMR (400 MHz, DMSO-d₆) δ [ppm]: 11.34 (br, 1H), 8.85 (s, 1H), 8.21 (s, 1H), 8.23 (d, 1H, J=9.2 Hz), 7.89-7.84 (m, 2H), 7.76 (s, 1H), 7.28-7.25 (m, 2H), 7.22-7.19 (m, 2H), 7.11 (d, 1H, J=10.0 Hz), 6.99-6.94 (m, 1H), 6.58 (s, 1H), 6.50-6.47 (m, 1H), 4.48 (s, 2H), 3.83 (s, 3H), 3.73 (s, 3H).

Step 3

A mixture of N-(2,4-dimethoxybenzyl)-6-(4-(6-fluoro-1H-indol-3-yl)-1H-pyrazol-1-yl)pyridazin-3-amine (80 mg; 0.18 mmol) and anisole (2.0 mL) in TFA (2.0 mL) was stirred at 120° C. for 2 hours in a microwave reactor. The reaction mixture was concentrated, and purified by a silica gel column chromatography (PE/EtOAc=4/1 to 2/1) to afford 30 mg (57%) of the title compound as a yellow solid.

¹H NMR (400 MHz, DMSO-d₆) δ [ppm]: 11.34 (br, 1H), 8.85 (s, 1H), 8.21 (s, 1H), 8.23 (d, 1H, 11.39 (br, 1H), 8.79 (s, 1H), 8.32 (s, 1H), 8.23 (d, 1H, J=9.2 Hz), 7.88-7.84 (m, 1H), 7.81 (s, 1H), 7.39 (d, 1H, J=10.0 Hz), 7.21 (d, 1H, J=10.0 Hz), 6.99-6.94 (m, 1H).

Example 110

6-fluoro-3-(1-(pyridazin-4-yl)-1H-pyrazol-4-yl)-1H-indole

Step 1: 3-(1-(3,6-dichloropyridazin-4-yl)-1H-pyrazol-4-yl)-6-fluoro-1-(phenylsulfonyl)-1H-indole To a solution of 6-fluoro-1-(phenylsulfonyl)-3-(1H-pyrazol-4-yl)-1H-indole (Intermediate 5; 200 mg; 0.59 mmol) in MeCN (10 mL) was added 3,4,6-trichloropyridazine (97 mg; 0.529 mmol) and K₂CO₃ (146 mg; 1.06 mmol) under nitrogen. The mixture was stirred at 85° C. for 24 hours, diluted with EtOAc (100 mL), washed with water (50 mL×3), brine (50 mL), dried over anhydrous Na₂SO₄, filtered, concentrated, and purified by reversed phase flash chromatography to afford 100 mg (39%) of the title compound a the yellow solid.

LC-MS: m/z 488 [M+H]⁺.

¹H NMR (400 MHz, CDCl₃) δ [ppm]: 8.77 (s, 1H), 8.15 (s, 1H), 8.12 (s, 1H), 7.96 (s, 1H), 7.94 (s, 1H), 7.80 (dd, J=10.0, 2.4 Hz, 1H), 7.76 (s, 1H), 7.63-7.56 (m, 2H), 7.54-7.48 (m, 2H), 7.12 (td, J=8.8, 2.4 Hz, 1H).

Step 2: 6-fluoro-1-(phenylsulfonyl)-3-(1-(pyridazin-4-yl)-1H-pyrazol-4-yl)-1H-indole A mixture of 3-(1-(3,6-dichloropyridazin-4-yl)-1H-pyrazol-4-yl)-6-fluoro-1-(phenylsulfonyl)-1H-indole (Step 1; 80 mg; 0.16 mmol) and Pd/C (30 mg; 10%) in MeOH (15 mL) was stirred for 1 hour under a hydrogen balloon. The reaction mixture was filtered and concentrated to afford 50 mg (64%) of the title compound as a yellow solid, which was used directly without further purification.
LC-MS: m/z 420 [M+H]$^+$.

Step 3

Following the general method as outlined in Example 70, starting from 6-fluoro-1-(phenylsulfonyl)-3-(1-(pyridazin-4-yl)-1H-pyrazol-4-yl)-1H-indole (Step 2; 50 mg; 0.12 mmol), 13 mg (39%) of the title compound was obtained as a white solid after purification by reverse phase flash chromatography.
$^1$H NMR (400 MHz, DMSO-d$_6$) δ [ppm]: 11.51 (s, 1H), 9.95 (d, J=2.8 Hz, 1H), 9.28 (d, J=5.2 Hz, 1H), 9.16 (s, 1H), 8.40 (s, 1H), 8.20-8.17 (m, 1H), 8.07-8.03 (m, 1H), 7.83 (d, J=2.4 Hz, 1H), 7.23 (dd, J=10, 2.4 Hz, 1H), 6.99 (dt, J=8.8, 2.4 Hz 1H).

Example 111

6-fluoro-3-(1-(pyridin-2-yl)-1H-pyrazol-4-yl)-1H-indole

Following the general method as outlined in Example 70, starting from 6-fluoro-1-(phenylsulfonyl)-3-(1-(pyridin-2-yl)-1H-pyrazol-4-yl)-1H-indole (Intermediate 15; 230 mg; 0.55 mmol), 17.2 mg (11%) of the title compound was obtained as a yellow solid after purification by preparative HPLC.
$^1$H NMR (400 MHz, MeOH-d$_4$) δ [ppm]: 8.75 (s, 1H), 8.36 (d, J=4.9 Hz, 1H), 7.99 (s, 1H), 7.85 (m, 2H), 7.69 (dd, J=8.7, 5.2 Hz, 1H), 7.44 (s, 1H), 7.20 (dd, J=8.5, 3.2 Hz, 1H), 7.02 (dd, J=9.8, 2.3 Hz, 1H), 6.82 (td, J=9.3, 2.3 Hz, 1H). m.p. 171.3-172.5° C.

Example 112

6-fluoro-3-(1-(pyridin-3-yl)-1H-pyrazol-4-yl)-1H-indole

Following the general method as outlined in Example 70, starting from 6-fluoro-1-(phenylsulfonyl)-3-(1-(pyridin-3-yl)-1H-pyrazol-4-yl)-1H-indole (Intermediate 12; 362 mg; 0.87 mmol), 63 mg (26%) of the title compound was obtained as a yellow solid after purification by preparative HPLC.
$^1$H NMR (400 MHz, DMSO-d$_6$) δ [ppm]: 11.38 (s, 1H), 9.25 (d, J=2.2 Hz, 1H), 8.98 (s, 1H), 8.53 (d, J=4.2 Hz, 1H), 8.36 (d, J=8.0 Hz, 1H), 8.25 (s, 1H), 8.03 (dd, J=8.6, 5.5 Hz, 1H), 7.77 (d, J=1.7 Hz, 1H), 7.57 (dd, J=8.2, 4.7 Hz, 1H), 7.23 (dd, J=10.0, 2.0 Hz, 1H), 6.98 (m, 1H). m.p. 203.0-204.6° C.

Example 113

6-fluoro-3-(1-(pyridin-4-yl)-1H-pyrazol-4-yl)-1H-indole

Following the general method as outlined in Example 70, starting from 6-fluoro-1-(phenylsulfonyl)-3-(1-(pyridin-4-yl)-1H-pyrazol-4-yl)-1H-indole (Intermediate 10; 363 mg; 0.87 mmol), 146 mg (60%) of the title compound was obtained as a yellow solid after purification by preparative HPLC.
$^1$H NMR (400 MHz, DMSO-d$_6$) δ [ppm]: 11.40 (d, 1H, J=1.6 Hz), 9.04 (s, 1H), 8.66 (d, 2H, J=4.7 Hz), 8.30 (s, 1H), 8.02 (m, 3H), 7.80 (s, 1H), 7.23 (d, 1H, J=9.5 Hz), 6.99 (t, 1H, J=8.8 Hz). m.p.>280° C.

II. Biology Examples

II.1. Assay for TDO2 Enzymatic Activity Determination

In certain preferred embodiments, the compounds of the present invention inhibit (e.g., decrease in a statistically significant manner relative to an appropriate control) the enzymatic activity of human TDO2 when the compounds are contacted with TDO2, for instance, under conditions and for a time sufficient for TDO2 activity to be manifest in the absence of the inhibitor.

To measure the TDO2 activity, the reaction mixture contained (final concentrations) potassium phosphate buffer (50 mM, pH 7.5), ascorbic acid (0.25 M), methylene blue (0.125 µM), catalase (40 units/mL, from bovine liver, Sigma), and human recombinant TDO2 enzyme (prepared as described in Dolusic et al. *J. Med. Chem.*; 2011, 54, 5320-5334; 0.9 µg) without or with the compounds of the present invention embodiments at the indicated concentrations (total volume 112.5 µL). The reaction was initiated by the addition of 37.5 µL of L-Trp (final concentration 1 mM) at room temperature. The reaction was conducted at room temperature during one hour and stopped by the addition of 30 µL of 30% (w/v) trichloroacetic acid.

To convert N-formylkynurenine into kynurenine, the reaction mixture was incubated at 65° C. for 30 min. Then 150 µL of the reaction mixture was mixed with 120 µL, of 2.5% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of certain embodiments of the compounds of the present invention. Data were fitted using the Prism software (GraphPad Software, Inc.).

The biological activity of representative Examples is summarized in the following table (*: 10 µM<IC$_{50}$<100 µM; : 1 µM<IC$_{50}$<10 µM; *: IC$_{50}$<1 µM):

| Example number | IC$_{50}$ |
| --- | --- |
| 2 | *** |
| 3 | ** |
| 4 | ** |
| 5 | ** |
| 6 | *** |
| 7 | *** |
| 8 | ** |
| 13 | ** |
| 14 | ** |
| 15 | ** |
| 16 | ** |
| 17 | * |
| 18 | ** |
| 19 | ** |
| 20 | ** |

-continued

| Example number | IC$_{50}$ |
|---|---|
| 21 | ** |
| 22 | ** |
| 23 | ** |
| 24 | *** |
| 25 | ** |
| 26 | *** |
| 27 | ** |
| 28 | * |
| 29 | ** |
| 30 | ** |
| 31 | ** |
| 32 | ** |
| 35 | ** |
| 36 | ** |
| 38 | ** |
| 39 | ** |
| 40 | ** |
| 41 | * |
| 42 | ** |
| 43 | *** |
| 44 | ** |
| 45 | ** |
| 46 | *** |
| 47 | *** |
| 48 | *** |
| 49 | ** |
| 50 | * |
| 51 | ** |
| 52 | *** |
| 53 | *** |
| 54 | ** |
| 58 | ** |
| 59 | ** |
| 60 | ** |
| 61 | ** |
| 62 | ** |
| 63 | ** |
| 64 | ** |
| 65 | * |
| 66 | * |
| 69 | ** |
| 70 | *** |
| 71 | *** |
| 72 | * |
| 73 | *** |
| 74 | ** |
| 75 | ** |
| 78 | ** |
| 79 | ** |
| 80 | * |
| 81 | ** |
| 82 | ** |
| 83 | ** |
| 84 | ** |
| 85 | ** |
| 86 | ** |
| 87 | ** |
| 88 | ** |
| 89 | ** |
| 90 | ** |
| 91 | ** |
| 107 | ** |
| 108 | * |
| 109 | ** |
| 110 | ** |
| 111 | *** |
| 112 | *** |
| 113 | *** |

II.2. Cellular Assay for TDO2 Activity Determination

The compounds according to certain embodiments of the present invention inhibit the activity of human TDO2 in cells. The assay was performed in 96-well flat bottom plates seeded with murine mastocytoma P815 cells overexpressing hTDO2 (prepared as described in Pilotte et al., PNAS, 2012, 109(7), 2497-2502), at a concentration of $5 \times 10^4$ cells/well in a final volume of 200 μL. To determine TDO or IDO activity, the cells were incubated overnight at 37° C. at 5% $CO_2$ in IMDM (Invitrogen) supplemented with 2% FBS and 2% penicillin/streptomycin in the presence of the compounds of the present invention, at different concentrations.

The plates were then centrifuged 5 min at 1000 rpm, and 100 μL of the supernatant were collected in a conical plate, 30 uL of TCA 30% were added and a further centrifugated at 3000×g for 10 minutes. 100 μL of the supernatant were collected in a flat bottomed plate and 100 μL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism software (GraphPad Software, Inc.).

The biological activity of representative Examples is summarized in the following table (*: 10 μM<IC$_{50}$<100 μM; : 1 μM<IC$_{50}$<10 μM; *: IC$_{50}$<1 μM):

| Example number | IC$_{50}$ |
|---|---|
| 2 | *** |
| 6 | *** |
| 7 | *** |
| 19 | *** |
| 20 | ** |
| 22 | ** |
| 24 | ** |
| 25 | *** |
| 26 | *** |
| 27 | *** |
| 29 | *** |
| 31 | *** |
| 35 | *** |
| 36 | *** |
| 38 | ** |
| 39 | ** |
| 40 | ** |
| 43 | *** |
| 44 | *** |
| 46 | *** |
| 47 | ** |
| 48 | *** |
| 51 | *** |
| 52 | *** |
| 53 | *** |
| 54 | ** |
| 58 | ** |
| 59 | ** |
| 60 | ** |
| 61 | *** |
| 62 | ** |
| 69 | ** |
| 70 | *** |
| 71 | *** |
| 73 | *** |
| 74 | *** |
| 75 | *** |
| 78 | *** |
| 85 | ** |
| 89 | *** |
| 91 | *** |
| 107 | *** |
| 109 | *** |
| 110 | ** |
| 111 | *** |
| 112 | *** |
| 113 | *** |

What is claimed is:

1. A compound of Formula I:

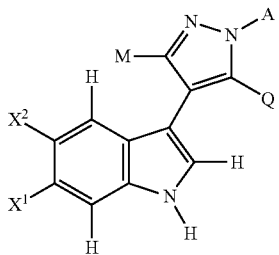

or a pharmaceutically acceptable enantiomer or salt thereof wherein:

$X^1$ and $X^2$ represent each independently H, halogen or haloalkyl;

M and Q represent each independently H, halogen, hydroxyl, or C1-C6 alkyl optionally substituted by one or more substituents selected from the group comprising halogen, hydroxyl, $CONR^1R^2$, or $NR^1COR^2$ wherein $R^1$ and $R^2$ represent each independently a group, optionally substituted, selected from C1-C6 alkyl, aryl, arylalkyl, alkylaryl, heteroaryl, heteroarylalkyl, or alkylheteroaryl;

A represents:

heteroaryl, optionally substituted with halogen, hydroxyl, nitro, amido, carboxy, amino, cyano, haloalkoxy, haloalkyl, or alkyl;

heterocyclyl; optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, or $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, or $SO_2Me$;

C1-C3 alkyl-heterocyclyl; wherein both the C1-C3 alkyl and the heterocyclyl are optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, or $SOR^1$, wherein $R^1$ and $R^2$ represent each independently a hydrogen atom or a group, optionally substituted, selected from C1-C6 alkyl, cycloalkyl, alkene, aryl, heteroaryl and amino, optionally substituted by one or more groups selected from halogen, hydroxyl, alkoxy, COOH, amino, or $SO_2Me$;

cycloalkyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1R^2$, $SO_2R^1$, $SO_2NR^1R^2$, $NR^1SO_2R^2$, or $SOR^1$, wherein $R^1$ and $R^2$ represent each independently a hydrogen atom or a group selected from C1-C6 alkyl, cycloalkyl, alkene, aryl, heteroaryl and amino, optionally substituted by one or more groups selected from halogen, hydroxyl, alkoxy, COOH, amino, or $SO_2Me$; or C1-C3 alkyl-cycloalkyl, optionally substituted with up to three substituents selected from the group comprising alkyl, the alkyl group being optionally substituted by one or more groups selected from halogen, hydroxyl or COOH; cycloalkyl, halogen, hydroxyl, oxo, alkoxy, $COOR^1$, $COR^1$, $CONR^1R^2$, $NR^1COR^2$, $NR^1R^2$, $SO_2R^1$, $SO_2NR^1R^2$, $NR^1SO_2R^2$, or $SOR^1$, wherein $R^1$ and $R^2$ represent each independently a group selected from C1-C6 alkyl, cycloalkyl, alkene, aryl, heteroaryl and amino, optionally substituted by one or more groups selected from halogen, hydroxyl, alkoxy, COOH, amino, or $SO_2Me$.

2. The compound according to claim 1, having Formula Ia:

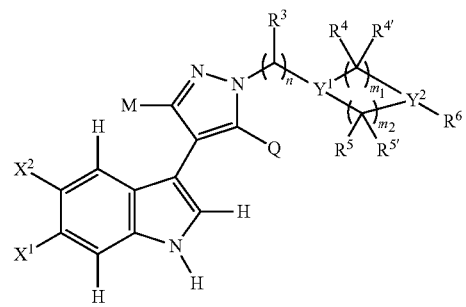

or a pharmaceutically acceptable enantiomer or salt thereof, wherein:

$X^1$ and $X^2$ represent each independently H, halogen or haloalkyl;

M and Q represent each independently H, halogen, hydroxyl, or C1-C6 alkyl optionally substituted by one or more substituents selected from the group comprising halogen, hydroxyl, $CONR^1R^2$, or $NR^1COR^2$, wherein $R^1$ and $R^2$ represent each independently a group, optionally substituted, selected from C1-C6 alkyl, aryl, arylalkyl, alkylaryl, heteroaryl, heteroarylalkyl, or alkylheteroaryl;

n represents an integer equal to 0, 1, 2 or 3;

$m_1$ and $m_2$ represent each independently an integer equal to 1 or 2;

$Y^1$ and $Y^2$ represent each independently $CR^7$, N, O, or $SO_2$, wherein $R^7$ represents H or hydroxyl;

$R^3$ represents H or alkyl;

$R^4$, $R^{4'}$, $R^5$ and $R^{5'}$ represent each independently H, hydroxyl, alkyl, alkoxy, or haloalkyl or $R^4$ and $R^{4'}$ form together an oxo moiety or $R^5$ and $R^{5'}$ form together an oxo moiety;

$R^6$ is absent or represents H or alkyl, the alkyl group being optionally substituted by one or more groups selected from halogen, hydroxyl or COOH; cycloalkyl, halogen, hydroxyl, oxo, $COR^1$, $COOR^1$, $CONR^1R^2$, $NR^1COR^2$, $NR^1R^2$, $SO_2R^1$, $SO_2NR^1R^2$, $NR^1SO_2R^2$, or $SOR^1$, wherein $R^1$ and $R^2$ represent each independently a hydrogen atom or a group selected from C1-C6 alkyl, cycloalkyl, alkene, aryl, heteroaryl or amino, optionally substituted by one or more groups selected from halogen, hydroxyl, alkoxy, COOH, amino, or $SO_2Me$.

3. The compound according to claim 1 or claim 2, having Formula Ia-1:

139

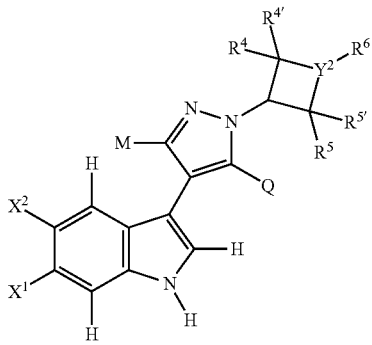

or a pharmaceutically acceptable enantiomer or salt thereof, wherein:

$X^1$ and $X^2$ represent each independently H or F;

M and Q represent each independently H or C1-C6 alkyl optionally substituted by one or more halogen;

$Y^2$ represents N or CH;

$R^4$, $R^{4'}$, $R^5$ and $R^{5'}$ represent each independently H, hydroxyl, alkyl, alkoxy, or haloalkyl, or $R^4$ and $R^{4'}$ form together an oxo moiety, or $R^5$ and $R^{5'}$ form together an oxo moiety;

$R^6$ represents H or alkyl, the alkyl group being optionally substituted by one or more groups selected from halogen, hydroxyl or COOH; cycloalkyl, halogen, hydroxyl, oxo, $COOR^1$, $COR^1$, $CONR^1R^2$, $NR^1COR^2$, $NR^1R^2$, $SO_2R^1$, $SO_2NR^1R^2$, $NR^1SO_2R^2$, or $SOR^1$, wherein $R^1$ and $R^2$ represent each independently a hydrogen atom or a group selected from C1-C6 alkyl, cycloalkyl, alkene, aryl, heteroaryl or amino, optionally substituted by one or more groups selected from halogen, hydroxyl, alkoxy, COOH, amino, or $SO_2Me$.

4. The compound according to claim 1 or claim 2, having Formula Ia-2:

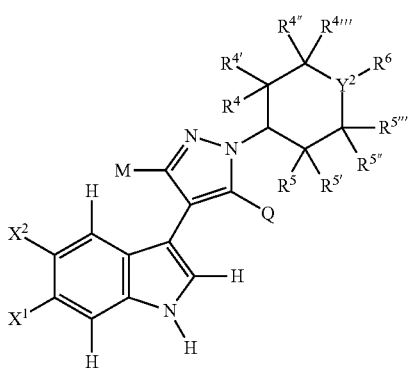

or a pharmaceutically acceptable enantiomer or salt thereof, wherein:

$X^1$ and $X^2$ represent each independently H or F;

M and Q represent each independently H or C1-C6 alkyl optionally substituted one or more halogen;

$Y^2$ represents N or CH;

$R^4$, $R^{4'}$, $R^{4''}$, $R^{4'''}$, $R^5$, $R^{5'}$, $R^{5''}$ and $R^{5'''}$ represent each independently H, hydroxyl, alkyl, alkoxy, or haloalkyl, or $R^4$ and $R^{4'}$ form together an oxo moiety, or $R^{4''}$ and $R^{4'''}$ form together an oxo moiety, or $R^5$ and $R^{5'}$ form together an oxo moiety, or $R^{5''}$ and $R^{5'''}$ form together an oxo moiety;

140

$R^6$ represents
H;
alkyl, the alkyl group being optionally substituted by one or more groups selected from halogen, hydroxyl or COOH;
cycloalkyl;
halogen;
hydroxyl;
oxo;
$COR^1$ or $SO_2R^1$, wherein $R^1$ represents a group selected from C1-C6 alkyl or cycloalkyl, wherein $R^1$ groups are optionally substituted by one or more groups selected from halogen, hydroxyl, alkoxy, COOH, amino, or $SO_2Me$.

5. The compound according to claim 1 or claim 2, having Formula Ia-3:

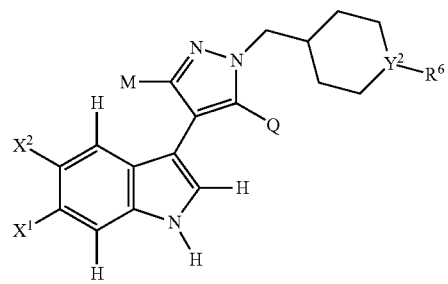

or a pharmaceutically acceptable enantiomer or salt thereof, wherein:

$X^1$ and $X^2$ represent each independently H or F;

M and Q represent each independently H or C1-C6 alkyl optionally substituted one or more halogen;

$Y^2$ represents N or CH;

$R^6$ represents
H;
alkyl, the alkyl group being optionally substituted by one or more groups selected from halogen, hydroxyl or COOH;
cycloalkyl; or
$COR^1$ or $SO_2R^1$, wherein $R^1$ represents a group selected from C1-C6 cycloalkyl, alkene, amino, wherein $R^1$ groups are optionally substituted by one or more groups selected from halogen, hydroxyl, alkoxy, COOH, amino, or $SO_2Me$.

6. The compound according to claim 1, having Formula Ic:

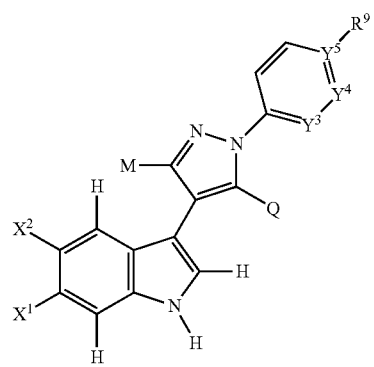

or pharmaceutically acceptable enantiomer or salt thereof, wherein:

$X^1$ and $X^2$ represent each independently H, halogen or haloalkyl;

M and Q represent each independently H, halogen, hydroxyl, or C1-C6 alkyl optionally substituted one or more substituents selected from the group comprising halogen, hydroxyl, CONR$^1$R$^1$, or NR$^1$COR$^2$, wherein R$^1$ and R$^2$ represent each independently a group, optionally substituted, selected from C1-C6 alkyl, aryl, arylalkyl, alkylaryl, heteroaryl, heteroarylalkyl, or alkylheteroaryl;

Y$^3$, Y$^4$, Y$^5$ represent each independently N or CH; and at least one of Y$^3$, Y$^4$, Y$^5$ represents N;

R$^9$ is absent or represents H, halogen, or amino.

7. The compound according to claim 1, selected from the group consisting of:
- 3-(4-(6-fluoro-1H-indol-3-yl)-1H-pyrazol-1-yl)azetidin-2-one,
- 3-(1-(azetidin-3-yl)-1H-pyrazol-4-yl)-6-fluoro-1H-indole,
- 1-(3-(4-(6-fluoro-1H-indol-3-yl)-1H-pyrazol-1-yl)azetidin-1-yl)ethanone,
- 3-(4-(6-fluoro-1H-indol-3-yl)-1H-pyrazol-1-yl)azetidine-1-carboxamide,
- 3-(4-(6-fluoro-1H-indol-3-yl)-1H-pyrazol-1-yl)-N-methylazetidine-1-carboxamide,
- 3-(1-(azetidin-3-ylmethyl)-1H-pyrazol-4-yl)-6-fluoro-1H-indole,
- 1-(2-(4-(6-fluoro-1H-indol-3-yl)-1H-pyrazol-1-yl)ethyl)imidazolidin-2-one,
- 6-fluoro-3-(1-(2-(4-methylpiperazin-1-yl)ethyl)-1H-pyrazol-4-yl)-1H-indole,
- 4-(2-(4-(6-fluoro-1H-indol-3-yl)-1H-pyrazol-1-yl)ethyl)morpholine,
- 6-fluoro-3-(1-(2-(piperazin-1-yl)ethyl)-1H-pyrazol-4-yl)-1H-indole,
- 1-(4-(2-(4-(6-fluoro-1H-indol-3-yl)-1H-pyrazol-1-yl)ethyl)piperazin-1-yl)ethanone,
- 6-fluoro-3-(1-(2-(pyrrolidin-1-yl)ethyl)-1H-pyrazol-4-yl)-1H-indole,
- 1-(2-(4-(6-fluoro-1H-indol-3-yl)-1H-pyrazol-1-yl)ethyl)pyrrolidin-2-one,
- 6-fluoro-3-(1-(piperidin-4-ylmethyl)-1H-pyrazol-4-yl)-1H-indole,
- 5,6-difluoro-3-(1-(piperidin-4-ylmethyl)-1H-pyrazol-4-yl)-1H-indole,
- 6-fluoro-3-(1-((1-(2,2,2-trifluoroethyl)piperidin-4-yl)methyl)-1H-pyrazol-4-yl)-1H-indole,
- 6-fluoro-3-(1-((1-(2-fluoroethyl)piperidin-4-yl)methyl)-1H-pyrazol-4-yl)-1H-indole,
- 2-(4-((4-(6-fluoro-1H-indol-3-yl)-1H-pyrazol-1-yl)methyl)piperidin-1-yl)ethanol,
- 1,1,1-trifluoro-3-(4-((4-(6-fluoro-1H-indol-3-yl)-1H-pyrazol-1-yl)methyl)piperidin-1-yl)propan-2-ol,
- 2-(4-((4-(6-fluoro-1H-indol-3-yl)-1H-pyrazol-1-yl)methyl)piperidin-1-yl)acetic acid,
- 4-(4-((4-(6-fluoro-1H-indol-3-yl)-1H-pyrazol-1-yl)methyl)piperidin-1-yl)-4-oxobutanoic acid,
- 1-(4-((4-(6-fluoro-1H-indol-3-yl)-1H-pyrazol-1-yl)methyl)piperidin-1-yl)ethanone,
- 3-(1-((1-cyclopropylpiperidin-4-yl)methyl)-1H-pyrazol-4-yl)-6-fluoro-1H-indole,
- 6-fluoro-3-(1-((1-methylpiperidin-4-yl)methyl)-1H-pyrazol-4-yl)-1H-indole,
- 6-fluoro-3-(1-((1-(methylsulfonyl)piperidin-4-yl)methyl)-1H-pyrazol-4-yl)-1H-indole,
- 3-(3,5-dimethyl-1-(piperidin-4-ylmethyl)-1H-pyrazol-4-yl)-6-fluoro-1H-indole,
- 6-fluoro-3-(3-methyl-1-(piperidin-4-ylmethyl)-1H-pyrazol-4-yl)-1H-indole,
- 6-fluoro-3-(5-methyl-1-(piperidin-4-ylmethyl)-1H-pyrazol-4-yl)-1H-indole,
- 6-fluoro-3-(1-((tetrahydro-2H-pyran-4-yl)methyl)-1H-pyrazol-4-yl)-1H-indole,
- 4-((4-(6-fluoro-1H-indol-3-yl)-1H-pyrazol-1-yl)methyl)tetrahydro-2H-pyran-4-ol,
- 4-((4-(6-fluoro-1H-indol-3-yl)-1H-pyrazol-1-yl)methyl)tetrahydro-2H-thiopyran 1,1-dioxide,
- (1S,3S)-3-(4-(6-fluoro-1H-indol-3-yl)-1H-pyrazol-1-yl)cyclobutanecarboxamide,
- (1R,3R)-3-(4-(6-fluoro-1H-indol-3-yl)-1H-pyrazol-1-yl)cyclobutanecarboxamide,
- (1S,3S)-3-(4-(6-fluoro-1H-indol-3-yl)-1H-pyrazol-1-yl)-N-methylcyclobutanecarboxamide,
- (1R,3R)-3-(4-(6-fluoro-1H-indol-3-yl)-1H-pyrazol-1-yl)-N-methylcyclobutanecarboxamide,
- (1S,3S)-3-(4-(6-fluoro-1H-indol-3-yl)-1H-pyrazol-1-yl)cyclobutanecarboxylic acid,
- (1R,3R)-3-(4-(6-fluoro-1H-indol-3-yl)-1H-pyrazol-1-yl)cyclobutanecarboxylic acid,
- (1R,4R)-4-(4-(6-fluoro-1H-indol-3-yl)-1H-pyrazol-1-yl)cyclohexanecarboxamide
- (1R,4R)-4-(4-(6-fluoro-1H-indol-3-yl)-1H-pyrazol-1-yl)cyclohexanol,
- (1R,4R)-4-(4-(6-fluoro-1H-indol-3-yl)-1H-pyrazol-1-yl)cyclohexanol,
- 6-fluoro-3-(1-(piperidin-4-yl)-1H-pyrazol-4-yl)-1H-indole,
- 2-(4-(4-(6-fluoro-1H-indol-3-yl)-1H-pyrazol-1-yl)piperidin-1-yl)ethanol,
- 4-(4-(4-(6-fluoro-1H-indol-3-yl)-1H-pyrazol-1-yl)piperidin-1-yl)-4-oxobutanoic acid,
- 1-(4-(4-(6-fluoro-1H-indol-3-yl)-1H-pyrazol-1-yl)piperidin-1-yl)-3-methoxypropan-1-one,
- 1-(4-(4-(6-fluoro-1H-indol-3-yl)-1H-pyrazol-1-yl)piperidin-1-yl)propan-1-one,
- 2-(dimethylamino)-1-(4-(4-(6-fluoro-1H-indol-3-yl)-1H-pyrazol-1-yl)piperidin-1-yl)ethanone,
- 1-(4-(4-(6-fluoro-1H-indol-3-yl)-1H-pyrazol-1-yl)piperidin-1-yl)-2-hydroxyethanone,
- 1-(4-(4-(6-fluoro-1H-indol-3-yl)-1H-pyrazol-1-yl)piperidin-1-yl)-2-methoxyethanone,
- 1-(4-(4-(6-fluoro-1H-indol-3-yl)-1H-pyrazol-1-yl)piperidin-1-yl)-2-methylpropan-1-one,
- 1-(4-(4-(6-fluoro-1H-indol-3-yl)-1H-pyrazol-1-yl)piperidin-1-yl)-2,2-dimethylpropan-1-one,
- cyclopropyl(4-(4-(6-fluoro-1H-indol-3-yl)-1H-pyrazol-1-yl)piperidin-1-yl)methanone,
- 1-(4-(4-(6-fluoro-1H-indol-3-yl)-1H-pyrazol-1-yl)piperidin-1-yl)ethanone,
- 4-(4-(6-fluoro-1H-indol-3-yl)-1H-pyrazol-1-yl)-N,N-dimethylpiperidine-1-carboxamide,
- 6-fluoro-3-(1-(1-methylpiperidin-4-yl)-1H-pyrazol-4-yl)-1H-indole,
- 6-fluoro-3-(1-(1-((trifluoromethyl)sulfonyl)piperidin-4-yl)-1H-pyrazol-4-yl)-1H-indole,
- 1-(4-(4-(1H-indol-3-yl)-5-(trifluoromethyl)-1H-pyrazol-1-yl)piperidin-1-yl)ethanone,
- 1-(4-(4-(6-fluoro-1H-indol-3-yl)-3-methyl-1H-pyrazol-1-yl)piperidin-1-yl)ethanone,
- 1-(4-(4-(6-fluoro-1H-indol-3-yl)-5-methyl-1H-pyrazol-1-yl)piperidin-1-yl)ethanone,
- 6-fluoro-3-(1-(1-((2-methoxyethyl)sulfonyl)piperidin-4-yl)-1H-pyrazol-4-yl)-1H-indole,
- 3-(1-(1-(cyclopropylsulfonyl)piperidin-4-yl)-1H-pyrazol-4-yl)-6-fluoro-1H-indole, 3-(1-(1-(ethylsulfonyl)piperidin-4-yl)-1H-pyrazol-4-yl)-6-fluoro-1H-indole,
6-fluoro-3-(1-(1-(isopropylsulfonyl)piperidin-4-yl)-1H-pyrazol-4-yl)-1H-indole,
4-(4-(6-fluoro-1H-indol-3-yl)-1H-pyrazol-1-yl)piperidin-2-one,
4-(4-(6-fluoro-1H-indol-3-yl)-1H-pyrazol-1-yl)-1-methylpiperidin-2-one,
1-(4-(4-(6-fluoro-1H-indol-3-yl)-1H-pyrazol-1-yl)piperidin-1-yl)prop-2-en-1-one,
1-(4-(4-(6-fluoro-1H-indol-3-yl)-1H-pyrazol-1-yl)piperidin-1-yl)-4-(methylsulfonyl)butan-1-one,
1-(4-(4-(6-fluoro-1H-indol-3-yl)-1H-pyrazol-1-yl)piperidin-1-yl)-3-hydroxypropan-1-one,
1-(4-(4-(6-fluoro-1H-indol-3-yl)-1H-pyrazol-1-yl)piperidin-1-yl)-3-(methylsulfonyl)propan-1-one,
6-fluoro-3-(1-(1-(methylsulfonyl)piperidin-4-yl)-1H-pyrazol-4-yl)-1H-indole,
6-fluoro-3-(1-(pyridazin-3-yl)-1H-pyrazol-4-yl)-1H-indole,
3-(1-(6-chloropyridazin-3-yl)-1H-pyrazol-4-yl)-6-fluoro-1H-indole,
6-(4-(6-fluoro-1H-indol-3-yl)-1H-pyrazol-1-yl)pyridazin-3-amine,
6-fluoro-3-(1-(pyridazin-4-yl)-1H-pyrazol-4-yl)-1H-indole,
6-fluoro-3-(1-(pyridin-2-yl)-1H-pyrazol-4-yl)-1H-indole,
6-fluoro-3-(1-(pyridin-3-yl)-1H-pyrazol-4-yl)-1H-indole,
6-fluoro-3-(1-(pyridin-4-yl)-1H-pyrazol-4-yl)-1H-indole,
or a pharmaceutically acceptable enantiomer or salt thereof.

8. A pharmaceutical composition comprising the compound claim 1, or a pharmaceutically acceptable enantiomer or salt thereof, and at least one or more of a pharmaceutically acceptable carrier, diluent, excipient and adjuvant.

9. A medicament comprising the compound of claim 1, or a pharmaceutically acceptable enantiomer or salt thereof.

10. A method of inhibiting tryptophan-2,3-dioxygenase (TDO1), comprising contacting TDO2 with the compound of claim 1 or a pharmaceutically acceptable enantiomer or salt thereof.

11. A process for manufacturing a compound of Formula I according to claim 1 or a pharmaceutically acceptable enantiomer or salt thereof, comprising deprotecting the indole amine of compound of Formula IV:

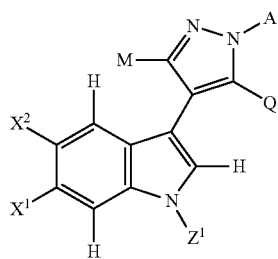

wherein
$X^1$, $X^2$, M, Q and A are as previously defined; and
$Z^1$ represents an amino-protecting group selected from an arylsulphonyl, a tert-butoxy carbonyl, a methoxymethyl, a para-methoxy benzyl and a benzyl;
to afford compound of Formula I.

12. The process of claim 11, further comprising a preliminary step of reacting a compound of Formula II,

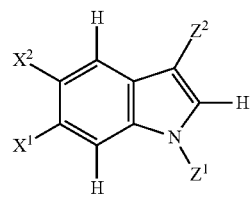

wherein
$X^1$ and $X^2$ are as previously defined;
$Z^1$ represents an amino-protecting group selected from an arylsulphonyl, a tert-butoxy carbonyl, a methoxymethyl, a para-methoxy benzyl and a benzyl;
$Z^2$ represents an halogen, an alkylsulfonyloxy having 1-6 carbon atoms or arylsulfonyloxy having 6-10 carbon atoms;
with a compound of Formula III

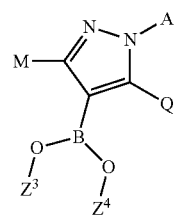

wherein
M, Q and A are as previously defined;
$Z^3$ and $Z^4$ represent alkyl groups, with the possibility for $Z^3$ and $Z^4$ to form together a ring;
so as to obtain a compound of Formula IV,

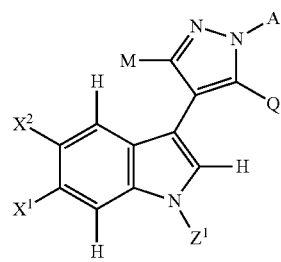

wherein $X^1$, $X^2$, M, Q, A and $Z^1$ are defined as above.

13. The process of claim 11, further comprising a preliminary step of reacting a compound of Formula V,

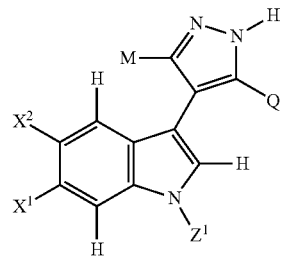

wherein
$X^1$, $X^2$, M and Q are as previously defined; and
$Z^1$ represents an amino-protecting group such as for example an arylsulphonyl, a tert-butoxy carbonyl, a methoxymethyl, a para-methoxy benzyl and a benzyl;

with a compound of Formula VI
Z⁵-A
wherein
A is as previously defined; and
Z⁵ represents a leaving group such as for example an halogen, alkylsulfonyloxy having 1-6 carbon atoms and arylsulfonyloxy having 6-10 carbon atoms;
so as to obtain a compound of Formula IV,
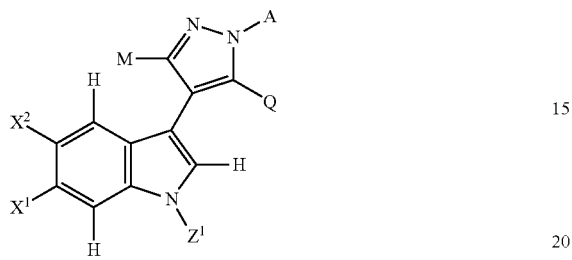
wherein $X^1$, $X^2$, M, Q, A and $Z^1$ are defined as above.
* * * * *